United States Patent
Xiang et al.

(10) Patent No.: US 12,234,226 B2
(45) Date of Patent: *Feb. 25, 2025

(54) COMPOUNDS AS NUCLEAR TRANSPORT MODULATORS AND USES THEREOF

(71) Applicant: XWPHARMA LTD., Grand Cayman (KY)

(72) Inventors: Jia-Ning Xiang, Fremont, CA (US); Zude Qi, Wuhan (CN); Xianbo Liu, Wuhan (CN); Dezheng Ning, Wuhan (CN)

(73) Assignee: XWPHARMA LTD., Grand Cayman (KY)

( * ) Notice: Subject to any disclaimer, the term of this patent is extended or adjusted under 35 U.S.C. 154(b) by 0 days.

This patent is subject to a terminal disclaimer.

(21) Appl. No.: 18/199,275

(22) Filed: May 18, 2023

(65) Prior Publication Data

US 2023/0303530 A1    Sep. 28, 2023

Related U.S. Application Data

(63) Continuation of application No. 17/112,922, filed on Dec. 4, 2020, now Pat. No. 11,767,313, which is a continuation of application No. PCT/CN2019/090189, filed on Jun. 5, 2019.

(30) Foreign Application Priority Data

Jun. 6, 2018  (WO) ................ PCT/CN2018/090151

(51) Int. Cl.
| | | |
|---|---|---|
| C07D 249/00 | (2006.01) |
| A61K 9/00 | (2006.01) |
| A61K 31/4196 | (2006.01) |
| A61K 31/454 | (2006.01) |
| A61K 31/497 | (2006.01) |
| A61P 35/00 | (2006.01) |
| C07D 233/00 | (2006.01) |
| C07D 249/02 | (2006.01) |
| C07D 249/08 | (2006.01) |
| C07D 257/04 | (2006.01) |
| C07D 271/00 | (2006.01) |
| C07D 271/02 | (2006.01) |
| C07D 401/12 | (2006.01) |
| C07D 403/12 | (2006.01) |
| C07D 419/12 | (2006.01) |

(52) U.S. Cl.
CPC .......... *C07D 403/12* (2013.01); *A61K 9/0053* (2013.01); *C07D 249/08* (2013.01); *C07D 401/12* (2013.01); *C07D 419/12* (2013.01)

(58) Field of Classification Search
CPC .. C07D 249/00; C07D 249/02; C07D 249/08; C07D 257/04; C07D 233/00; C07D 247/00; C07D 271/02; A61K 31/497; A61K 31/4196; A61K 31/454; A61P 35/00

See application file for complete search history.

(56) References Cited

FOREIGN PATENT DOCUMENTS

| | | |
|---|---|---|
| CN | 106831731 | 6/2017 |
| JP | 2014-502641 | 2/2014 |
| JP | 2014-521652 | 8/2014 |
| JP | 2017-527549 | 9/2017 |
| WO | 2011/109799 | 9/2011 |
| WO | 2013/019548 | 2/2013 |
| WO | 2013/019561 | 2/2013 |
| WO | 2013/170068 | 11/2013 |
| WO | 2012/036278 | 2/2014 |
| WO | 2014/144772 | 9/2014 |
| WO | 2014/152263 | 9/2014 |
| WO | 2014/205389 | 12/2014 |
| WO | 2014/205393 | 12/2014 |
| WO | 2017/117529 | 7/2017 |
| WO | 2017/118940 | 7/2017 |
| WO | 2018/098472 | 5/2018 |
| WO | 2018/129227 | 7/2018 |
| WO | 2019/232724 | 12/2019 |

OTHER PUBLICATIONS

International Search Report and Written Opinion for Application No. PCT/CN2019/090189, mailed on Sep. 18, 2019, 16 pages.
International Search Report and Written Opinion for Application No. PCT/CN2018/090151, mailed on Feb. 20, 2019, 14 pages.
Brekhov et al., "Cynomethyltetrazoles. 2. Reactions involving the methylene fragment", Journal of Organic Chemistry, 1992, vol. 28, No. 9, pp. 1921-1925.
Cognitive Vitality, "KPT-350 Cognitive Vitality for Researchers", Retrieved on Nov. 17, 2021, from URL: https://www.alzdiscovery.org/uploads/cognitive_vitality_media/KPT-350-Cognitive-Vitality-For-Researchers.pdf, originally published Sep. 24, 2019, 12 pages.

*Primary Examiner* — Bruck Kifle

(57) ABSTRACT

Nuclear transport modulators are disclosed. The compounds can inhibit nuclear transporters such as the exportin-1 transporter. The compounds and pharmaceutical compositions comprising the compounds can be used to treat neurological diseases and cancer.

14 Claims, 13 Drawing Sheets

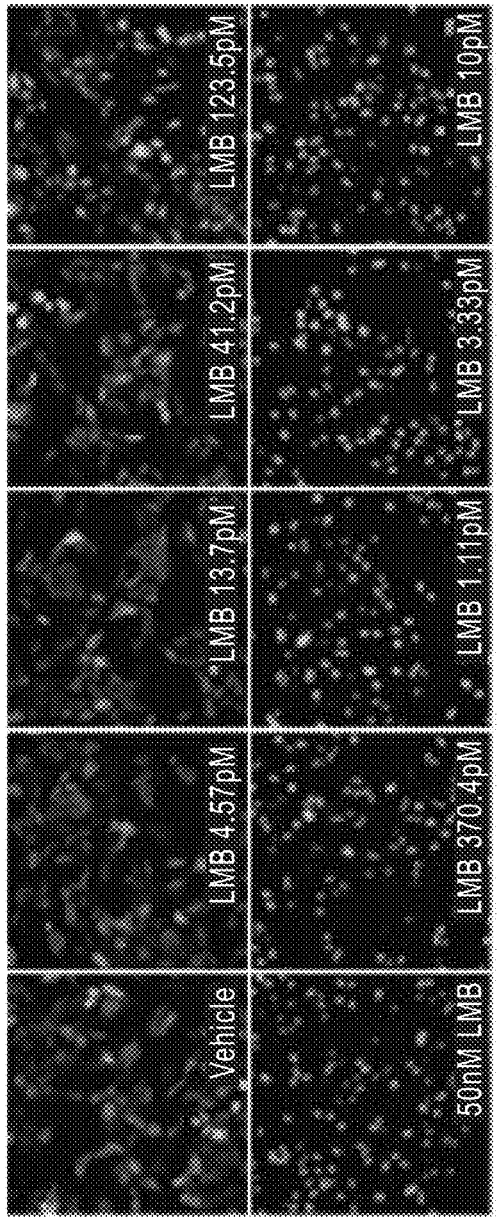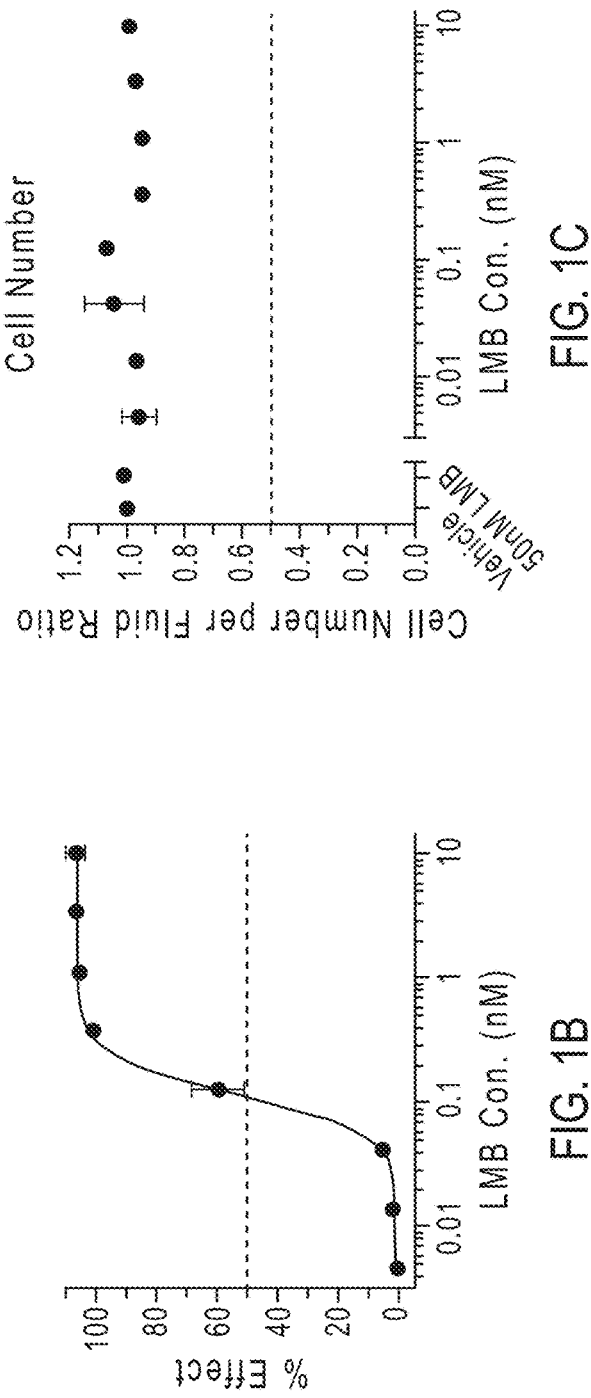
FIG. 1A
FIG. 1B
FIG. 1C

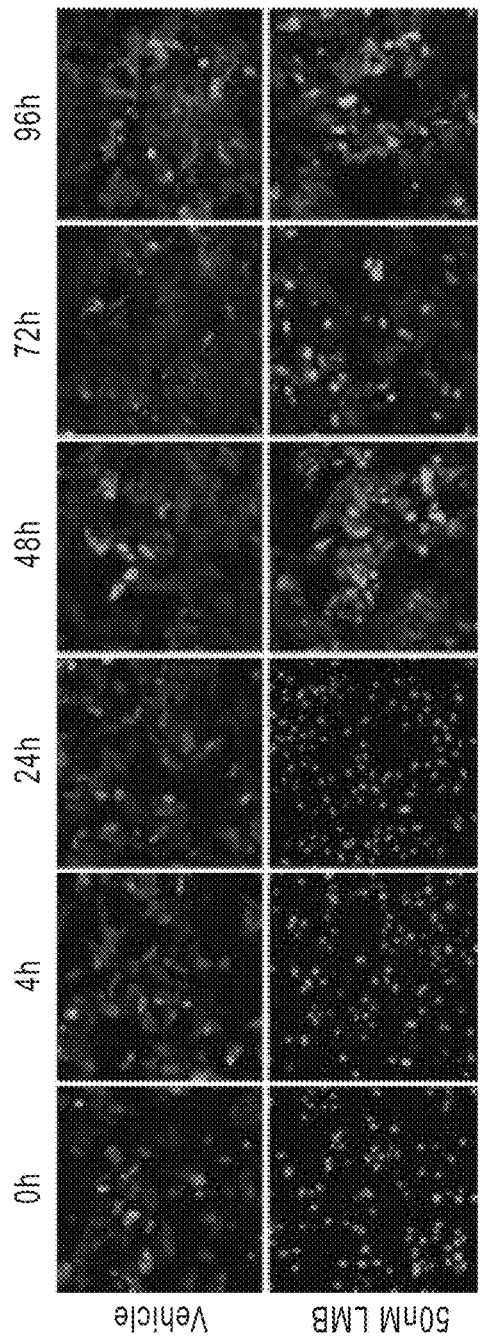
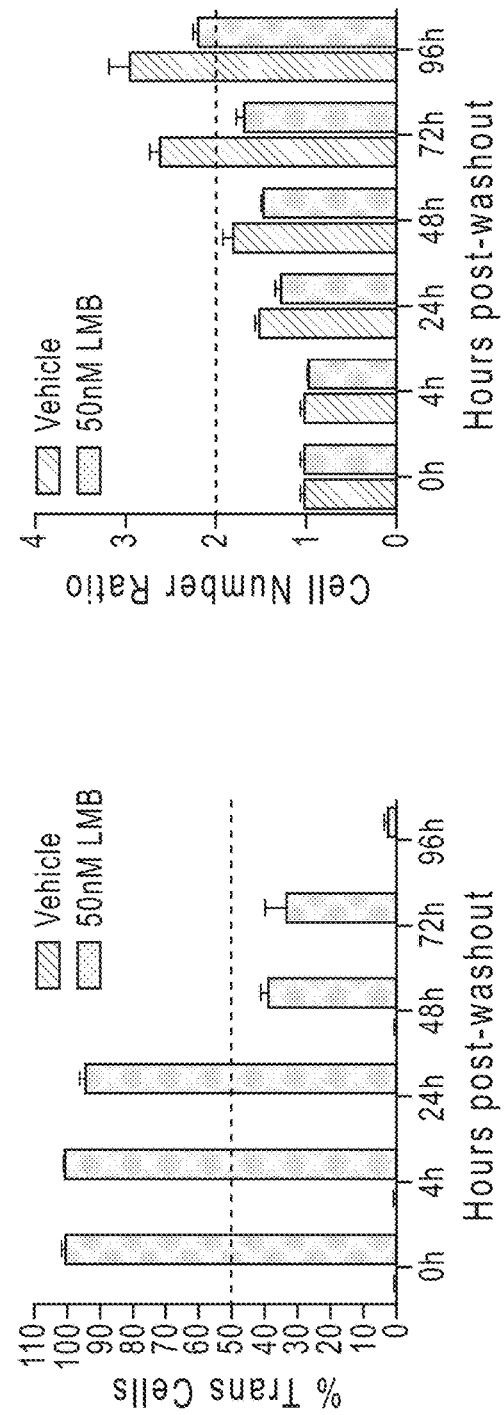
FIG. 3A
FIG. 3B
FIG. 3C

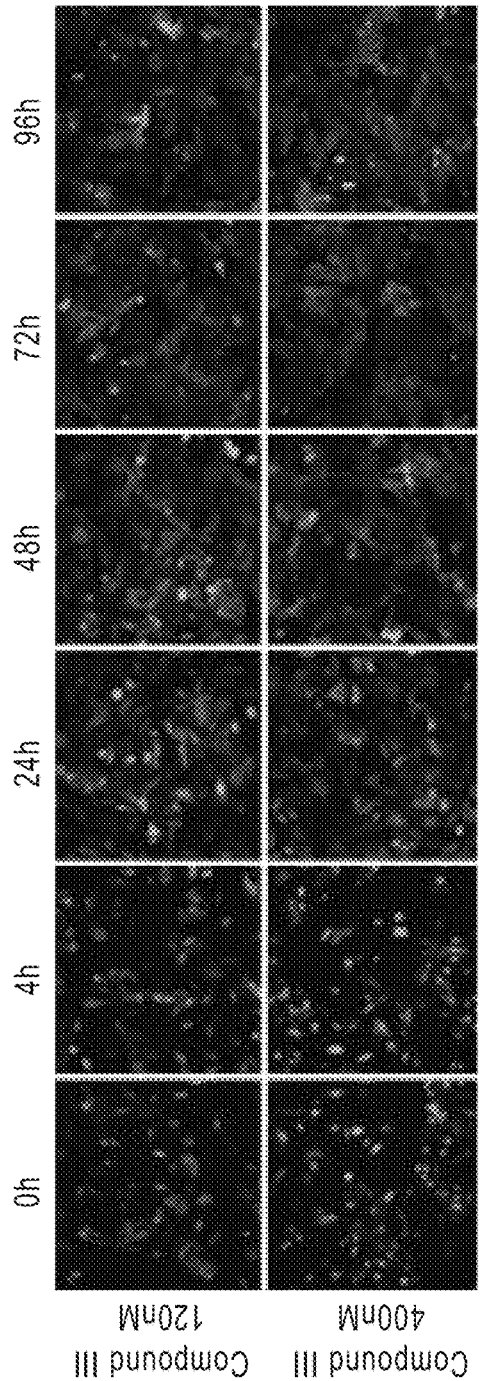
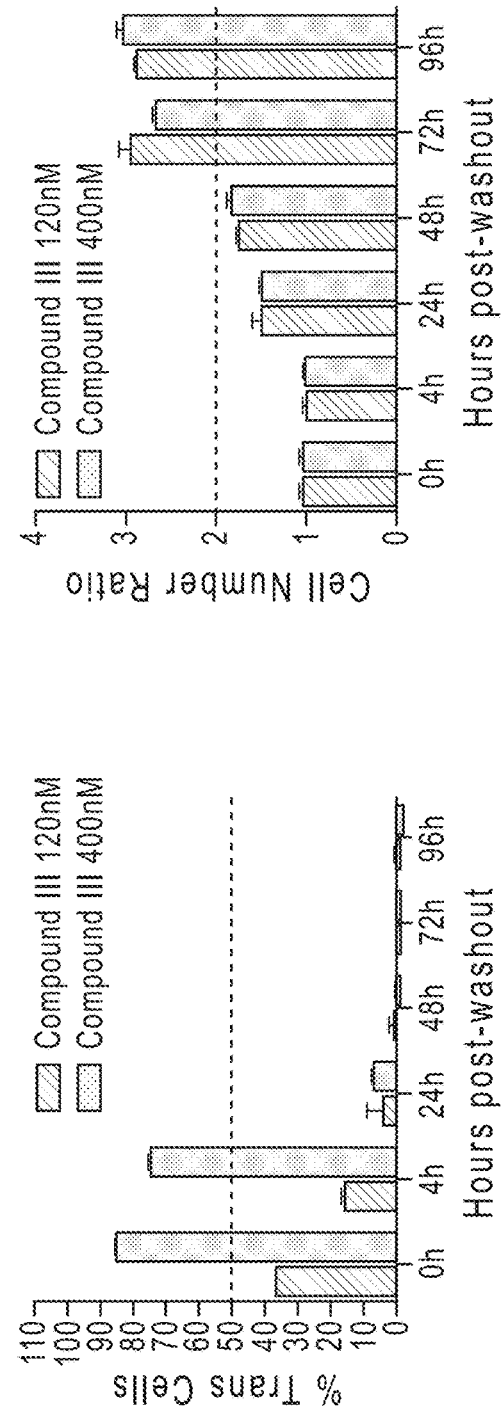

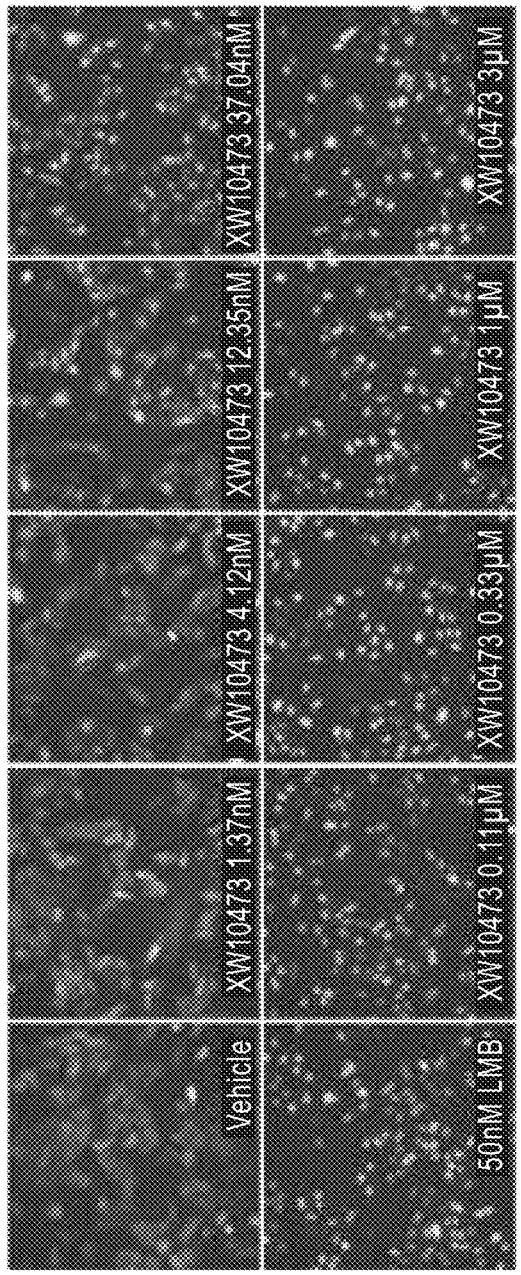
FIG. 13A
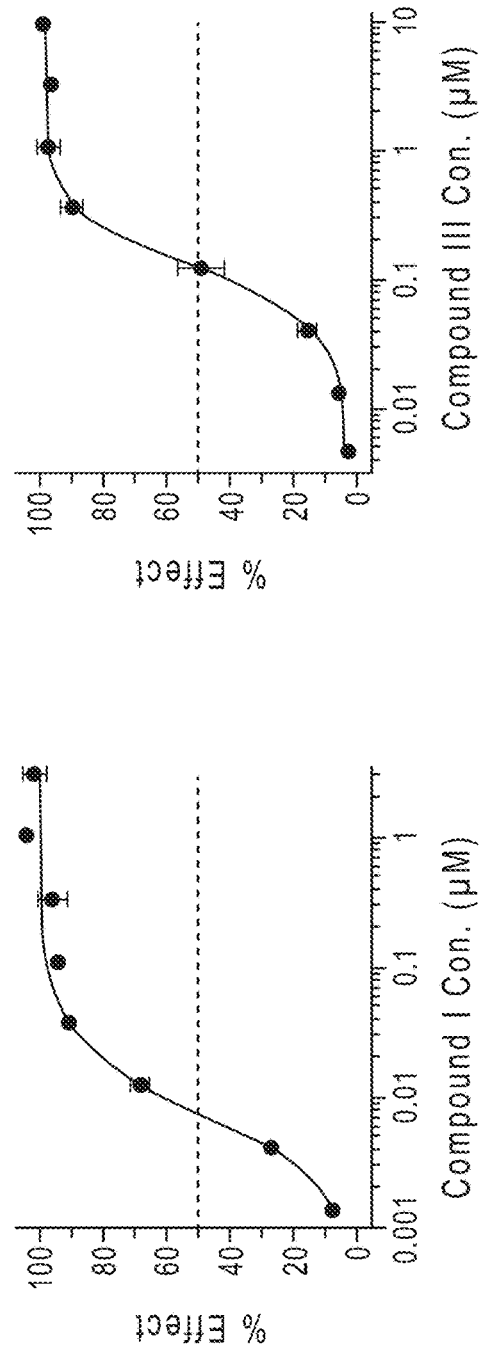
FIG. 13B
FIG. 13C

COMPOUNDS AS NUCLEAR TRANSPORT MODULATORS AND USES THEREOF

This application is a continuation of U.S. application Ser. No. 17/112,922, filed on Dec. 4, 2020, now allowed, which is a continuation of PCT International Application No. PCT/CN2019/090189, filed on Jun. 5, 2019, which claims priority to PCT International Application No. PCT/CN2018/090151, filed on Jun. 6, 2018, each of which is incorporated by reference in its entirety.

FIELD

The present invention relates to the field of medicinal technology, in particular, to certain compounds, their preparation and uses, as well as pharmaceutical compositions comprising such compounds. As exemplified, the present invention relates to certain compounds as nuclear transport modulators, their preparation, and the corresponding pharmaceutical compositions. The compounds and/or pharmaceutical compositions of the present invention can be potentially used in the manufacture of a medicament for preventing, treating, or ameliorating certain disorder or a disease in a patient, which includes, inter alia, a neurological disorder or cancer. It is believed that the compounds and/or pharmaceutical compositions of the present invention exert their therapeutic benefits by, among other things, acting to modulate exportin-1 (XPO1) activities.

BACKGROUND

Since its initial functionality was published 10 years ago, exportin-1 (as known as CRM-1 and XPO-1, has emerged as a key 'carrier' protein for transporting some crucial growth regulatory proteins and tumor suppressors from the nucleus to the cytoplasm of eukaryotic cells. When exportin-1's efflux becomes abnormally high (e.g., due to over-expressed XPO-1 production), depletion of these nuclear regulators can trigger a wide variety of diseases (e.g., for some extensive listings: WO 2017/117529 A1 and WO 2017/117535 A1).

For example, XPO1 is the sole nuclear exporter transporting the tumor suppressors, e.g., p53, p27, FOXO1, IkB and it is overexpressed in various sold tumors and hematological malignancies, such as GBM, ovarian, pancreatic, and cervical cancers, AML, MM, CLL, and NHL. Here, the main key point of XPO1 for cancer is overexpression of XPO1 protein in multiple types of cancer cells, and its association with proliferated cell cycle, depleting tumor suppressor proteins (e.g., p53, p27, FOXO1, IkB) in the nucleus, which allows cancer cells to grow (e.g., M. L. Crochiere, et. al., *Oncotarget* v.7, pp. 1863-1877 (2015). Selective inhibitors of nuclear exportin-1 (e.g., KPT-330, (Z)-3-(3-(3,5-bis(trifluoromethyl)phenyl)-1H-1,2,4-triazol-1-yl)-N'-(pyrazin-2-yl)acrylohydrazide, a Karyopharm's SINE drug candidate) have begun clinical trials and have shown promising clinical Phase 2 efficacy to treat some of these cancers.

In general, Selective Inhibitor of Nuclear Export (SINE) compounds are a family of small-molecules that inhibit nuclear export of cargo proteins through covalent binding to cysteine 528 (Cys528) in the cargo-binding pocket of Exportin 1 (XPO1, also called CRM1, chromosome maintenance protein 1) and exert anti-proliferative effects. The interaction between XPO1 and the activated small G-protein Ran (Ran-GTP) in the nucleus facilitates the binding to cargo proteins containing a short amino acid sequence of hydrophobic residues called a nuclear export signal (NES).

Based on pre-clinical results, a similar pathology is also implicated in many inflammatory, neurodegenerative and autoimmune diseases. As a consequence, for example, glucocorticoids are widely used anti-inflammatory and immunomodulatory drugs whose mechanism of efficacy/action is mainly based on restoring enough steroid activated glucocorticoid receptor (GR) to interfere against the excessive activities of transcription factors such as NF-κB in the nucleus. As revealed by its positive efficacy in animal models, KPT-350 ((Z)-3-(3-(3,5-bis(trifluoromethyl)phenyl)-1H-1,2,4-triazol-1-yl)-N'-pivaloylacrylohydrazide) may have the potential to treat amyotrophic lateral sclerosis, multiple sclerosis, traumatic brain injury, epilepsy, systemic lupus erythematosus and rheumatoid arthritis.

While drugs inhibiting diseases caused by excessive XPO-1 efflux remain to be proven as clinically efficacious by the US FDA today, many diseases still urgently need novel drug treatments. For an example, US FDA has not yet approved sales of any drug to specifically treat traumatic brain injury (e.g., concussions) which annually afflicts at least 1.7 million Americans. As a second urgent need, ~30% of epileptic patients are/become unfortunately resistant to FDA currently approved drugs. As a third example, patients afflicted with rare glioblastoma (up to ~3.7 per 100,000 age adjusted incidence rate in surveyed European countries have very poor prognosis (e.g., relative 5-year survival rates reach up to 4.4% by the same survey).

SUMMARY

The following is only an overview of some aspects of the present invention but is not limited thereto. All references of this specification are incorporated herein by reference in their entirety. When the disclosure of this specification is different with citations, the disclosure of this specification shall prevail. The present invention provides compounds and pharmaceutical compositions which modulate exportin-1 activities, their preparation, and the corresponding pharmaceutical compositions. The compounds and/or pharmaceutical compositions of the present invention can be potentially used in the manufacture of a medicament for preventing, treating, ameliorating certain disorder or a disease in a patient associated with exportin-1 activities, which includes, inter alia, certain neurological disorders or cancer.

One aspect of the present invention is the provision of a compound having the structure of Formula (I'), Formula (II') or Formula (III'):

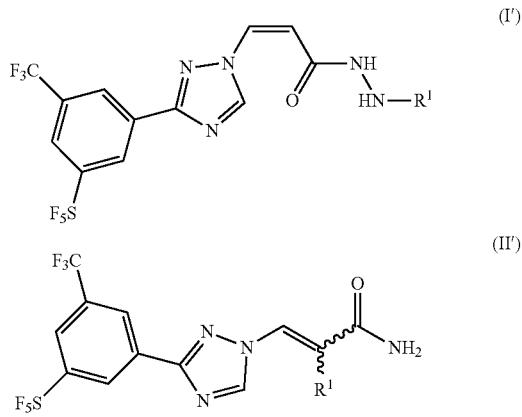

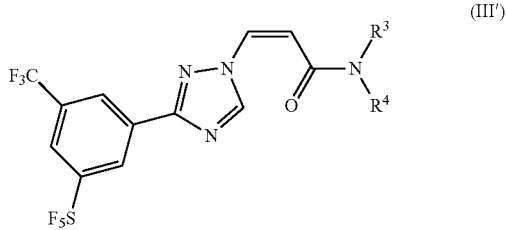

a stereoisomer, an N-oxide, a solvate, a metabolite, a pharmaceutically acceptable salt or a prodrug thereof, wherein, $R^1$ is independently selected from —C(=O)—$R^2$, $C_{3-6}$ heterocycloalkyl, $C_{5-10}$ heteroaryl; any heterocycloalkyl or heteroaryl of $R^1$ is optionally independently substituted with one, or more substituents selected from the group consisting of deuterium, —OH, —SH, —NO$_2$, halogen, amino, cyano, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy and $C_{1-12}$ alkylsulfanyl; and $R^2$ is independently selected from $C_{1-6}$ alkyl, $C_{3-6}$ cycloalkyl, $C_{3-6}$ heterocycloalkyl; any alkyl, cycloalkyl, heterocycloalkyl of $R^2$ is optionally and independently substituted with one or more substituents selected from the group consisting of halogen, amino, cyano, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy and $C_{1-12}$ alkylsulfanyl; and $R^3$, $R^4$ are independently selected from $C_{1-6}$ alkyl, substituted $C_{1-6}$ alkyl, or $R^3$ and $R^4$ together with N which they are attached form a substituted or unsubstituted $C_{4-10}$ cycloalkylamino; any alkyl or cycloalkylamino of $R^3$ and $R^4$ is optionally and independently substituted with one or more substituents selected from the group consisting of halogen, amino, cyano, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy and $C_{1-12}$ alkylsulfanyl.

In a further aspect, the invention relates to pharmaceutical compositions each comprising an effective amount of at least one compound of Formula (I'-III') or a pharmaceutically acceptable salt of a compound of Formula (I'-III'). Pharmaceutical compositions according to the invention may further comprise at least one pharmaceutically acceptable excipient, carrier, adjuvant, solvent, support or a combination thereof.

In another aspect, the invention is directed to a method of treating a subject suffering from a disorder or a disease, which includes, inter alia, certain neurological disorders or cancer, by modulating exportin-1 activities, comprising administering to the subject in need of such treatment an effective amount of at least one compound of Formula (I'-III') or a pharmaceutically acceptable salt of a compound of Formula (I'-III'), or comprising administering to the subject in need of such treatment an effective amount of a pharmaceutical composition comprising an effective amount of at least one compound of Formula (I'-III') or a pharmaceutically acceptable salt of a compound of Formula (I'-III').

In yet another aspect, the invention is directed to a method of treating a subject suffering from certain neurological disorders or diseases, which disorders or diseases comprise amyotrophic lateral sclerosis, epilepsy, traumatic brain injuries, Huntington's disease, Parkinson's disease, rheumatoid arthritis, systemic lupus erythematosus.

In still another aspect, the invention is directed to a method of treating a subject suffering from a cancer, which comprises lymphoma, liposarcoma, multiple myeloma, myelodysplastic syndrome, prostate cancer, colorectal cancer, endometrial cancer, pancreatic cancer, gastric cancer, diffuse large B-cell lymphoma, non-small cell lung cancer, ovarian carcinoma, breast cancer, acute myeloid leukemia, thymoma, esophageal cancer, glioblastoma, and other solid tumors.

An aspect of the present invention concerns the use of compound of Formula (I'-III') for the preparation of a medicament used in the treatment, prevention, inhibition or elimination of certain neurological disorders or cancer, which medicament further comprises adjunctive therapies, such as radiation, or therapeutically effective amounts of one or more, optional, adjunctive active ingredients, which adjunctive active ingredients comprise a chemotherapeutic agent, a TK or RTK inhibitor, a BCL2 inhibitor, a FLT3 inhibitor, a EGFR inhibitor, a pro-apoptotic drug, an antibody-drug conjugate (ADC), an immune checkpoint inhibitor, CAR-T, a personalized cancer vaccine, and a chemokine/cytokine.

In yet another aspect of the present invention, the compounds of Formula (I'-III') and pharmaceutically acceptable salts thereof are useful as modulators of XPO1 activities. Thus, the invention is directed to a method for modulating XPO1 activities in a subject, comprising exposing the subject to an effective amount of at least one compound of Formula (I'-III') or a pharmaceutically acceptable salt of a compound of Formula (I'-III').

In yet another aspect, the present invention is directed to methods of making compounds of Formula (I'-III') and pharmaceutically acceptable salts thereof.

In certain embodiments of the compounds, pharmaceutical compositions, and methods of the invention, the compound of Formula (I'-III') is a compound selected from those species described or exemplified in the detailed description below or is a pharmaceutically acceptable salt of such a compound.

Another preferred embodiment, the present invention is directed to methods of preparing pharmaceutical compositions each comprising an effective amount of at least one compound of Formula (I'-III') or a pharmaceutically acceptable salt of a compound of Formula (I'-III'). Pharmaceutical compositions according to the invention may further comprise at least one pharmaceutically acceptable excipient, carrier, adjuvant, solvent, support or a combination thereof.

If formulated as a fixed dose, such combination products employ the compounds of this invention within the dosage range described herein (or as known to those skilled in the art) and the other pharmaceutically active agents or treatments within its dosage range. For example, the CDC2 inhibitor olomucine has been found to act synergistically with known cytotoxic agents in inducing apoptosis (*J. Cell Sci.*, (1995) 108, 2897). The compounds of the invention may also be administered sequentially with known anticancer or cytotoxic agents when a combination formulation is inappropriate. In any combination treatment, the invention is not limited in the sequence of administration; compounds of Formula (I'-III') may be administered either prior to or after administration of the known anticancer or cytotoxic agent. For example, the cytotoxic activity of the cyclin-dependent kinase inhibitor flavopiridol is affected by the sequence of administration with anticancer agents (*Cancer Research*, (1997) 57, 3375). Such techniques are within the skills of persons skilled in the art as well as attending physicians.

Any of the aforementioned methods may be augmented by administration of fluids (such as water), loop diuretics, one or more of a chemotherapeutic or antineoplastic agent, such as leucovorin and fluorouracil, and an adjunctive chemotherapeutic agent (such as filgrastim and erythropoietin), or any combination of the foregoing.

Yet another embodiment is a method for administering a compound of the instant invention to a subject (e.g., a human) in need thereof by administering to the subject the pharmaceutical formulation of the present invention.

Yet another embodiment is a method of preparing a pharmaceutical formulation of the present invention by mixing at least one pharmaceutically acceptable compound of the present invention, and, optionally, one or more pharmaceutically acceptable additives or excipients.

For preparing pharmaceutical compositions from the compounds described by this invention, inert, pharmaceutically acceptable carriers can be either solid or liquid. Solid form preparations include powders, tablets, dispersible granules, capsules, beads, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences,* 18th Edition, (1990), Mack Publishing Co., Easton, Pa.

Liquid form preparations include solutions, suspensions and emulsions. As an example, may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 500 mg, more preferably from about 1 mg to about 250 mg, still more preferably from about 1 mg to about 200 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 200 mg/day, in one to two divided doses.

Any embodiment disclosed herein can be combined with other embodiments as long as they are not contradictory to one another, even though the embodiments are described under different aspects of the invention. In addition, any technical feature in one embodiment can be applied to the corresponding technical feature in other embodiments as long as they are not contradictory to one another, even though the embodiments are described under different aspects of the invention.

The foregoing merely summarizes certain aspects disclosed herein and is not intended to be limiting in nature. These aspects and other aspects and additional embodiments, features, and advantages of the invention will be apparent from the following detailed description and through practice of the invention.

BRIEF DESCRIPTION OF THE DRAWINGS

These and other aspects and advantages of embodiments of the present disclosure will become apparent and more readily appreciated from the following descriptions made with reference the accompanying schemes and drawings, in which:

FIGS. 1A-1C show the EC50 of XPO1 inhibition by Compound III in REV-GFP U2OS assay.

FIGS. 3A-3C show sustained XPO1 inhibition by LMB in washout study.

FIGS. 4A-4C show Compound III exhibited XPO1 inhibition and the inhibition was abrogated 24 hours post washout in REV-GFP U2OS assay.

FIGS. 13A-13C show the EC50 of XPO1 inhibition by Compound I and Compound III in the REV-GFP U2OS assay.

DETAILED DESCRIPTION

Figure 2A:
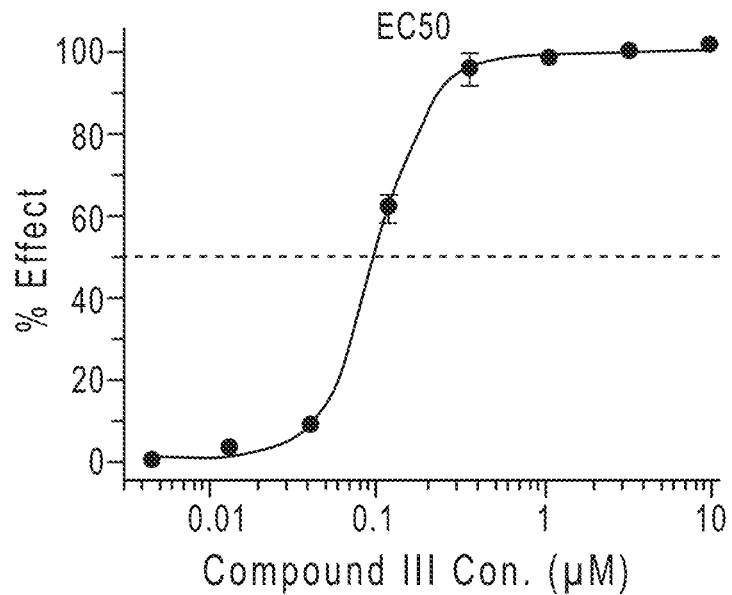
FIGS. 2A-2B show EC50 in REV cargo inhibition, and it did not affect cell viability.

For the sake of brevity, the disclosures of the publications cited in this specification, including patents and patent applications, are herein incorporated by reference in their entirety.

Most chemical names were generated using IUPAC nomenclature herein. Some chemical names were generated using different nomenclatures or alternative or commercial names known in the art. In the case of conflict between names and structures, the structures prevail.

Reference will now be made in detail to certain embodiments of the invention, examples of which are illustrated in the accompanying structures and formulas. The invention is intended to cover all alternatives, modifications and equivalents which may be included within the scope of the present invention as defined by the claims. One skilled in the art will recognize many methods and materials similar or equivalent to those described herein, which could be used in the practice of the present invention. The present invention is in no way limited to the methods and materials described herein. In the event that one or more of the incorporated literatures, patents, and similar materials differs from or contradicts this application, including but not limited to defined terms, term usage, described techniques, or the like, this application controls.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

Unless defined otherwise, all technical and scientific terms used herein have the same meaning as are commonly understood by one skilled in the art to which this invention belongs. All patents and publications referred to herein are incorporated by reference in their entirety.

As used herein, the following definitions shall apply unless otherwise indicated. For purposes of this invention, the chemical elements are identified in accordance with the Periodic Table of the Elements, CAS version, and the *Handbook of Chemistry and Physics*, 75th Ed. 1994. Additionally, general principles of organic chemistry are described in *Organic Chemistry*, Thomas Sorrell, University Science Books, Sausalito, 1999, and *March's Advanced Organic Chemistry* by Michael B. Smith and Jerry March, John Wiley & Sons, New York, 2007.

As used above, and throughout this disclosure, the following terms, unless otherwise indicated, shall be understood to have the following meanings. If a definition is missing, the conventional definition as known to one skilled in the art controls. If a definition provided herein conflicts or is different from a definition provided in any cited publication, the definition provided herein controls.

As used herein, the terms "including", "containing", and "comprising" are used in their open, non-limiting sense.

As used herein, the singular forms "a", "an", and "the" include plural referents unless the context clearly dictates otherwise.

To provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

As used herein, "alkyl" refers to a saturated, straight- or branched-chain hydrocarbon group having from 1 to 12 carbon atoms. Representative alkyl groups include, but are not limited to, methyl, ethyl, n-propyl, isopropyl, 2-methyl-1-propyl, 2-methyl-2-propyl, 2-methyl-1-butyl, 3-methyl-1-butyl, methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl, and the like, and longer alkyl groups, such as heptyl, octyl, and the like. As used herein, "lower alkyl" means an alkyl having from 1 to 6 carbon atoms.

The term "alkylamino" as used herein denotes an amino group as defined herein wherein one hydrogen atom of the amino group is replaced by an alkyl group as defined herein. Aminoalkyl groups can be defined by the following general formula —NH-alkyl. This general formula includes groups of the following general formula: —NH—$C_1$-$C_{10}$ alkyl and —NH—$C_1$-$C_6$ alkyl. Examples of aminoalkyl groups include, but are not limited to aminomethyl, aminoethyl, aminopropyl, aminobutyl.

The term "dialkylamino" as used herein denotes an amino group as defined herein wherein two hydrogen atoms of the amino group are replaced by alkyl groups as defined herein. Diaminoalkyl groups can be defined by the following general formula —N(alkyl)$_2$, wherein the alkyl groups can be the same or can be different and can be selected from alkyls as defined herein, for example $C_1$-$C_{10}$ alkyl or $C_1$-$C_6$ alkyl.

The term "alkoxy" as used herein includes —O-(alkyl), wherein alkyl is defined above.

As used herein, "alkoxyalkyl" means -(alkylenyl)-O-(alkyl), wherein each "alkyl" is independently an alkyl group defined above.

The term "amino" as used herein refers to an —NH$_2$ group.

"Aryl" means a mono-, bi-, or tricyclic aromatic group, wherein all rings of the group are aromatic. For bi- or tricyclic systems, the individual aromatic rings are fused to one another. Exemplary aryl groups include, but are not limited to, phenyl, naphthalene, and anthracene.

"Aryloxy" as used herein refers to an —O-(aryl) group, wherein aryl is defined as above.

"Arylalkyl" as used herein refers to an -(alkylenyl)-(aryl) group, wherein alkylenyl and aryl are as defined above. Non-limiting examples of arylalkyls comprise a lower alkyl group. Non-limiting examples of suitable arylalkyl groups include benzyl, 2-phenethyl, and naphthalenylmethyl.

"Arylalkoxy" as used herein refers to an —O-(alkylenyl)-aryl group wherein alkylenyl and aryl are as defined above.

The term "cyano" as used herein means a substituent having a carbon atom joined to a nitrogen atom by a triple bond.

The term "cyanoalkyl" denotes an alkyl group as defined above wherein a hydrogen atom of the alkyl group is replaced by a cyano (—CN) group. The alkyl portion of the cyanoalkyl group provides the connection point to the remainder of the molecule.

The term "deuterium" as used herein means a stable isotope of hydrogen having one proton and one neutron.

The term "halogen" as used herein refers to fluorine, chlorine, bromine, or iodine. The term "halo" represents chloro, fluoro, bromo, or iodo.

The term "haloalkyl" denotes an alkyl group as defined above wherein one or more, for example one, two, or three of the hydrogen atoms of the alkyl group are replaced by a halogen atom, for example fluoro, bromo, or chloro, in particular fluoro. Examples of haloalkyl include, but are not limited to, monofluoro-, difluoro-, or trifluoro-methyl, -ethyl or -propyl, for example, 3,3,3-trifluoropropyl, 2-fluoroethyl, 2,2,2-trifluoroethyl, fluoromethyl, difluoromethyl, or trifluoromethyl, or bromoethyl or chloroethyl. Similarly, the term "fluoroalkyl" refers to an alkyl group as defined above substituted with one or more, for example one, two, or three fluorine atoms.

The term "haloalkoxy" as used herein refers to an —O-(haloalkyl) group wherein haloalkyl is defined as above. Exemplary haloalkoxy groups are bromoethoxy, chloroethoxy, trifluoromethoxy and 2,2,2-trifluoroethoxy.

The term "hydroxy" means an —OH group.

The term "hydroxyalkyl" denotes an alkyl group that is substituted by at least one hydroxy group, for example, one, two or three hydroxy group(s). The alkyl portion of the hydroxyalkyl group provides the connection point to the remainder of a molecule. Examples of hydroxyalkyl groups include, but are not limited to, hydroxymethyl, hydroxyethyl, 1-hydroxypropyl, 2-hydroxyisopropyl, 1,4-dihydroxybutyl, and the like.

The term "oxo" means an =O group and may be attached to a carbon atom or a sulfur atom. The term "N-oxide" refers to the oxidized form of a nitrogen atom.

As used herein, the term "cycloalkyl" refers to a saturated or partially saturated, monocyclic, fused polycyclic, bridged polycyclic, or spiro polycyclic carbocycle having from 3 to 12 ring carbon atoms. A non-limiting category of cycloalkyl groups are saturated or partially saturated, monocyclic carbocycles having from 3 to 6 carbon atoms. Illustrative examples of cycloalkyl groups include, but are not limited to, the following moieties:

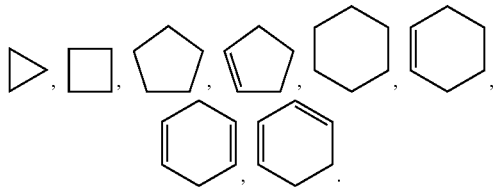

The term "cycloalkoxy" refers to a —O-(cycloalkyl) group.

As used herein, the term "heteroaryl" refers to a monocyclic, or fused polycyclic, aromatic heterocycle having from 3 to 15 ring atoms that are selected from carbon, oxygen, nitrogen, selenium and sulfur. Suitable heteroaryl groups do not include ring systems that must be charged to be aromatic, such as pyrylium. Some suitable 5-membered heteroaryl rings (as a monocyclic heteroaryl or as part of a polycyclic heteroaryl) have one oxygen, sulfur, or nitrogen atom, or one nitrogen plus one oxygen or sulfur, or 2, 3, or 4 nitrogen atoms. Some suitable 6-membered heteroaryl rings (as a monocyclic heteroaryl or as part of a polycyclic heteroaryl) have 1, 2, or 3 nitrogen atoms. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The term "bicyclic heteroaryl" refers to a heteroaryl as defined above, having two constituent aromatic rings, wherein the two rings are fused to one another and at least one of the rings is a heteroaryl as defined above. Bicyclic heteroaryls include bicyclic heteroaryl groups comprising 1, 2, 3, or 4 heteroatom ring members and are unsubstituted or substituted with one or more substituents selected from the group consisting of amino and halo; and wherein one or more N ring members of said heteroaryl is optionally an N-oxide.

Those skilled in the art will recognize that the species of heteroaryl, and cycloalkyl groups listed or illustrated above are not exhaustive, and that additional species within the scope of these defined terms may also be selected.

As described herein, compounds disclosed herein may optionally be substituted with one or more substituents, or as exemplified by particular classes, subclasses, and species of the invention.

As used herein, the term "substituted" means that the specified group or moiety bears one or more suitable substituents. As used herein, the term "unsubstituted" means that the specified group bears no substituents. As used herein, the term "optionally substituted" means that the specified group is unsubstituted or substituted by the specified number of substituents. Where the term "substituted" is used to describe a structural system, the substitution is meant to occur at any valency-allowed position on the system. "Substituted" refers to a group in which one or more hydrogen atoms are independently replaced with the same or different substituent(s). Each substituent can be independently selected from deuterio, halogen, —OH, —CN, —CF$_3$, —OCF$_3$, =O, —NO$_2$, C$_{1-6}$ alkoxy, C$_{1-6}$ alkyl, —COOR, —NR$_2$, and —CONR$_2$; wherein each R is independently selected from hydrogen and C$_{1-6}$ alkyl. Each substituent can be independently selected from deuterio, halogen, —NH$_2$, —OH, C$_{1-3}$ alkoxy, and C$_{1-3}$ alkyl, trifluoromethoxy, and trifluoromethyl. Each substituent can be independently selected from deuterio, —OH, methyl, ethyl, trifluoromethyl, methoxy, ethoxy, and trifluoromethoxy. Each substituent can be selected from deuterio, C$_{1-3}$ alkyl, =O, C$_{1-3}$ alkyl, C$_{1-3}$ alkoxy, and phenyl. Each substituent can be selected from deuterio, —OH, —NH$_2$, C$_{1-3}$ alkyl, and C$_{1-3}$ alkoxy.

As used herein, the expression "one or more substituents" denotes one to maximum possible number of substitution(s) that can occur at any valency-allowed position on the system. In a certain embodiment, one or more substituent means 1, 2, 3, 4, or 5 substituents. In another embodiment, one or more substituent means 1, 2, or 3 substituents.

As used herein, the double bond in Formula II' bearing its substituents attached with "⟋⟍" bonds represents either an E or Z configuration.

Any atom that is represented herein with an unsatisfied valence is assumed to have the sufficient number of hydrogen atoms to satisfy the atom's valence.

When any variable (e.g., alkyl, alkylenyl, heteroaryl, $R^1$, $R^2$) appears in more than one place in any formula or description provided herein, the definition of that variable on each occurrence is independent of its definition at every other occurrence.

Numerical ranges, as used herein, are intended to include sequential whole numbers. For example, a range expressed as "from 0 to 4" or "0-4" includes 0, 1, 2, 3 and 4, while a range expressed as "10-20%" includes 10%, 11%, 12%, 13%, 14%, 15%, 16%, 17%, 18%, 19% and 20%. Similarly, numerical ranges are also intended to include sequential fractional integers. For example, a range expressed as "1-2%" would include 1.0%, 1.1%, 1.2%, 1.3%, 1.4%, 1.5%, 1.6%, 1.7%, 1.8%, 1.9% and 2.0%.

When a multifunctional moiety is shown, the point of attachment to the core is indicated by a line or hyphen. For example, aryloxy—refers to a moiety in which an oxygen atom is the point of attachment to the core molecule while aryl is attached to the oxygen atom.

As used herein, the term "subject" encompasses mammals and non-mammals. Examples of mammals include, but are not limited to, any member of the Mammalian class: humans; non-human primates such as chimpanzees, and other apes and monkey species; farm animals such as cattle, horses, sheep, goats, swine; domestic animals such as rabbits, dogs, and cats; and laboratory animals including rodents, such as rats, mice and guinea pigs, and the like. Examples of non-mammals include, but are not limited to, birds, fish and the like. In one embodiment of the present invention, the mammal is a human.

"Patient" includes both human and animals.

The term "inhibitor" refers to a molecule such as a compound, a drug, an enzyme activator, or a hormone that blocks or otherwise interferes with a particular biologic activity.

The term "modulator" refers to a molecule, such as a compound of the present invention, that increases or decreases, or otherwise affects the activity of a given protein, receptor and/or ion channels.

The terms "effective amount" or "therapeutically effective amount" refer to a sufficient amount of the agent to provide the desired biological result. That result can be reduction and/or alleviation of the signs, symptoms, or causes of a disease or medical condition, or any other desired alteration of a biological system. For example, an "effective amount" for therapeutic use is the amount of a compound, or of a composition comprising the compound, that is required to provide a clinically relevant change in a disease state, symptom, or medical condition. An appropriate "effective" amount in any individual case may be determined by one of ordinary skill in the art using routine experimentation. Thus, the expression "effective amount" generally refers to the quantity for which the active substance has a therapeutically desired effect.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

As used herein, the terms "administration of" and "administering a" compound should be understood to mean providing a compound of the invention, pharmaceutical composition comprising a compound or a prodrug of a compound of the invention to an individual in need thereof. It is recognized that one skilled in the non-limiting art can treat a patient presently afflicted with neurological and psychiatric disorders or by prophylactically treat a patient afflicted with the disorders with an effective amount of the compound of the present invention.

The term "composition" as used herein is intended to encompass a product comprising the specified ingredients in the specified amounts, as well as any product which results, directly or indirectly, from combinations of the specified ingredients in the specified amounts. Such term in relation to pharmaceutical composition, is intended to encompass a product comprising the active ingredient(s) and the inert ingredient(s) that make up the carrier, as well as any product which results, directly or indirectly, from a combination, complexation or aggregation of any two or more of the ingredients, or from the other types of reactions or interactions such as to cause the dissociation of one or more of the ingredients. Accordingly, the pharmaceutical compositions of the present invention encompass any composition made by mixing a compound of the present invention and a pharmaceutically acceptable carrier.

Any formula given herein is intended to represent compounds having structures depicted by the structural formula as well as certain variations or forms. For example, compounds of any formula given herein may have asymmetric or chiral centers and therefore exist in different stereoisomeric forms. All stereoisomers, including optical isomers, enantiomers, and diastereomers, of the compounds of the general formula, and mixtures thereof, are considered to fall within the scope of the formula. Furthermore, certain structures may exist as geometric isomers (i.e., cis and trans isomers), as tautomers, or as atropisomers. All such isomeric forms, and mixtures thereof, are contemplated herein as part of the present invention. Thus, any formula given herein is intended to represent a racemate, one or more enantiomeric forms, one or more diastereomeric forms, one or more tautomeric or atropisomeric forms, and mixtures thereof.

"Stereoisomer" refers to compounds which have identical chemical constitution but differ with regard to the arrangement of the atoms or groups in space. Stereoisomers include enantiomer, diastereomers, conformer (rotamer), geometric (cis/trans) isomer, atropisomer etc.

"Chiral" refers to molecules which have the property of non-superimposability of the mirror image partner, while the term "achiral" refers to molecules which are superimposable on their mirror image partner.

"Enantiomers" refers to two stereoisomers of a compound which are non-superimposable mirror images of one another.

"Diastereomer" refers to a stereoisomer with two or more centers of chirality and whose molecules are not mirror images of one another. Diastereomers have different physical properties, e.g., melting points, boiling points, spectral properties or biological activities. A mixture of diastereomers may be separated under high resolution analytical procedures such as electrophoresis and chromatography such as HPLC.

Stereochemical definitions and conventions used herein generally follow S. P. Parker, Ed., McGraw-Hill *Dictionary of Chemical Terms* (1984) McGraw-Hill Book Company, New York; and Eliel, E. and Wilen, S., *Stereochemistry of Organic Compounds*, John Wiley & Sons, Inc., New York, 1994.

Many organic compounds exist in optically active forms, i.e., they have the ability to rotate the plane of polarized light. In describing an optically active compound, the prefixes D and L, or R and S, are used to denote the absolute configuration of the molecule about its chiral center(s). The prefixes d and/or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Any asymmetric atom (e.g., carbon or the like) of the compound(s) disclosed herein can be in racemic or enantiomerically enriched, for example the (R)-, (S)- or (R, S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents or resolved using conventional techniques. If the compound contains a double bond, the substituent may be E or Z configuration. If the compound contains a disubstituted cycloalkyl, a cycloalkyl substituent may have a cis- or trans-configuration relative to another substituent of the same cycloalkyl frame.

Any resulting mixtures of stereoisomers can be separated on the basis of the physicochemical differences of the constituents, into the pure or substantially pure geometric isomers, enantiomers, diastereomers, for example, by chromatography and/or fractional crystallization. Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., *Enantiomers, Racemates and Resolutions* (Wiley Interscience, New York, 1981); *Principles of Asymmetric Synthesis* (2nd Ed. Robert E. Gawley, Jeffrey Aubé, Elsevier, Oxford, U K, 2012); Eliel, E. L., *Stereochemistry of Carbon Compounds* (McGraw-Hill, N Y, 1962); Wilen, S. H., *Tables of Resolving Agents and Optical Resolutions* p. 268 (E. L. Eliel, Ed., Univ. of Notre Dame Press, Notre Dame, IN 1972); *Chiral Separation Techniques: A Practical Approach* (Subramanian, G. Ed., Wiley-VCH Verlag GmbH & Co. KGaA, Weinheim, Germany, 2007).

Diastereomeric mixtures may be separated into their individual diastereomers on the basis of their physical chemical differences by methods well known to those skilled in the art, such as, for example, by chromatography and/or fractional crystallization. Enantiomers may be separated by converting the enantiomeric mixture into a diastereomeric mixture by reaction with an appropriate optically active compound (e.g., chiral auxiliary such as a chiral alcohol or Mosher's acid chloride, or formation of a mixture of diastereomeric salts), separating the diastereomers and converting (e.g., hydrolyzing or de-salting) the individual diastereomers to the corresponding pure enantiomers. Enantiomers may also be separated by use of chiral HPLC column.

The compounds of the invention can form pharmaceutically acceptable salts, which are also within the scope of this invention. A "pharmaceutically acceptable salt" refers to a salt of a free acid or base of a compound of Formula (I') that is non-toxic, is physiologically tolerable, is compatible with the pharmaceutical composition in which it is formulated, and is otherwise suitable for formulation and/or administration to a subject. Reference to a compound herein is understood to include reference to a pharmaceutically acceptable salt of said compound unless otherwise indicated.

Compound salts include acidic salts formed with inorganic and/or organic acids, as well as basic salts formed with inorganic and/or organic bases. In addition, where a given compound contains both a basic moiety, such as, but not limited to, a pyridine or imidazole, and an acidic moiety, such as, but not limited to, a carboxylic acid, one of skill in the art will recognize that the compound may exist as a zwitterion ("inner salt"); such salts are included within the term "salt" as used herein. Salts of the compounds of the invention may be prepared, for example, by reacting a compound with an amount of a suitable acid or base, such as an equivalent amount, in a medium such as one in which the salt precipitates or in an aqueous medium followed by lyophilization.

Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate ("mesylate"), ethanesulfonate, benzenesulfonate, p-toluenesulfonate, and pamoate (i.e., 1,1'-methylene-bis(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counterions. Hence, a pharmaceutically acceptable salt can have one or more charged atoms and/or one or more counter ion.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, tert-butyl amines, and salts with amino acids such as arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

Additionally, acids and bases which are generally considered suitable for the formation of pharmaceutically useful salts from pharmaceutical compounds are discussed, for example, by P. Stahl et al, Camille G. (eds.) *Handbook of Pharmaceutical Salts. Properties, Selection and Use*, (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, MD, available from FDA). These disclosures are incorporated herein by reference thereto.

Additionally, any compound described herein is intended to refer also to any unsolvated form, or a hydrate, solvate, or polymorph of such a compound, and mixtures thereof, even if such forms are not listed explicitly. "Solvate" means a physical association of a compound of the invention with one or more solvent molecules. This physical association involves varying degrees of ionic and covalent bonding, including hydrogen bonding. In certain instance the solvate will be capable of isolation, for example when one or more solvent molecules are incorporated in the crystal lattice of a crystalline solid. "Solvate" encompasses both solution-phase and isolatable solvates. Suitable solvates include those formed with pharmaceutically acceptable solvents such as water, ethanol, and the like. In some embodiments, the solvent is water and the solvates are hydrates.

One or more compounds of the invention may optionally be converted to a solvate. Methods for the preparation of solvates are generally known. Thus, for example, M. Caira et al., *J. Pharmaceutical Sci.*, 93(3), 601-611 (2004), describes the preparation of the solvates of the antifungal fluconazole in ethyl acetate as well as from water. Similar preparations of solvates, hemisolvate, hydrates, and the like are described by E. C. van Tonder et al, *AAPS PharmSciTech.*, 5(1), article 12 (2004); and A. L. Bingham et al, *Chem. Commun.*, 603-604 (2001). A typical, non-limiting process involves dissolving the compound of the invention in a suitable amount of the solvent (organic solvent or water or a mixture thereof) at a higher than ambient temperature and cooling the solution at a rate sufficient to form crystals which are then isolated by standard methods. Analytical techniques such as, for example, infrared spectroscopy, show the presence of the solvent (or water) in the crystals as a solvate (or hydrate).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^{2}H$, $^{3}H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labelled compounds are useful in metabolic studies (for example with $^{14}C$), reaction kinetic studies (with, for example $^{2}H$ or $^{3}H$), detection or imaging techniques [such as positron emission tomography (PET) or single-photon emission computed tomography (SPECT) including drug or substrate tissue distribution assays, or in radioactive treatment of patients. In particular, an $^{18}F$ or $^{11}C$ labeled compound may be particularly suitable for PET or SPECT studies. Further, substitution with heavier isotopes such as deuterium (i.e., $^{2}H$) may afford certain therapeutic advantages resulting from greater metabolic stability, for example increased in vivo half-life or reduced dosage requirements. Isotopically labeled compounds of this invention can generally be prepared by carrying out the procedures disclosed in the schemes or in the examples and preparations described below by substituting a readily available isotopically labeled reagent for a non-isotopically labeled reagent.

The use of the terms "salt," "solvate," "polymorph," and the like, with respect to the compounds described herein is intended to apply equally to the salt, solvate, and polymorph forms of enantiomers, stereoisomers, rotamers, tautomers, atropisomers, and racemates of the compounds of the invention.

The chemical nomenclature tool is the software of ChemDraw Professional 16.0.

The present invention relates to particular molecules and pharmaceutically acceptable salts or isomers thereof. The invention further relates to molecules which are useful in modulating dysfunctional XPO1 activities and pharmaceutically acceptable salts, solvates, esters, or isomers thereof.

The invention is directed to compounds as described herein and pharmaceutically acceptable salts, solvates, esters, or isomers thereof, and pharmaceutical compositions comprising one or more compounds as described herein and pharmaceutically acceptable salts or isomers thereof.

One aspect of this invention is the provision of compounds, compositions, kits, and antidotes for modulating XPO1 activities in mammals having a compound a compound having the structure of Formula (I'), Formula (II') or Formula (III'):

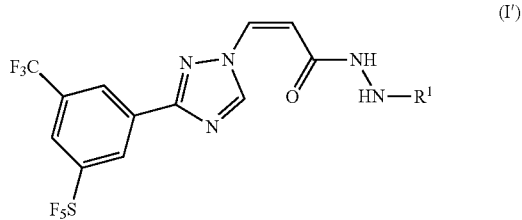

(I')

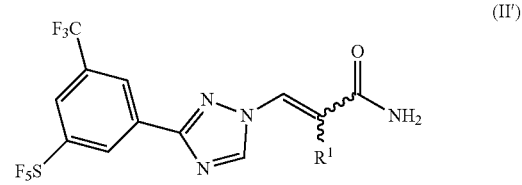

(II')

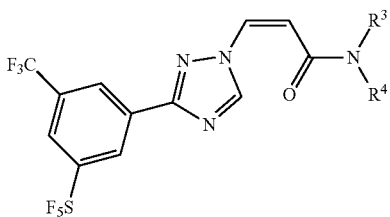

(III')

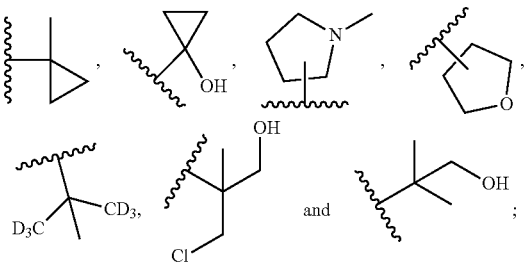

a stereoisomer, an N-oxide, a solvate, a metabolite, a pharmaceutically acceptable salt or a prodrug thereof, wherein, $R^1$ is independently selected from —C(=O)—$R^2$, $C_{3-6}$ heterocycloalkyl, $C_{5-10}$ heteroaryl; any heterocycloalkyl or heteroaryl of $R^1$ is optionally independently substituted with one, or more substituents selected from the group consisting of deuterium, —OH, —SH, —NO$_2$, halogen, amino, cyano, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy and $C_{1-12}$ alkylsulfanyl; and $R^2$ is independently selected from $C_{1-6}$ alkyl, $C_{3-6}$ cycloalkyl, $C_{3-6}$ heterocycloalkyl; any alkyl, cycloalkyl, heterocycloalkyl of $R^2$ is optionally and independently substituted with one or more substituents selected from the group consisting of halogen, amino, cyano, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy and $C_{1-12}$ alkylsulfanyl; and $R^3$, $R^4$ are independently selected from $C_{1-6}$ alkyl, substituted $C_{1-6}$ alkyl, or $R^3$ and $R^4$ together with N which they are attached form a substituted or unsubstituted $C_{4-10}$ cycloalkylamino; any alky or cycloalkylamino of $R^3$ and $R^4$ is optionally and independently substituted with one or more substituents selected from the group consisting of halogen, amino, cyano, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy and $C_{1-12}$ alkylsulfanyl.

In one embodiment of the invention, the compound has the structure of Formula (I').

In another embodiment of the invention, the compound has the structure of Formula (II'), and the configuration of the double bond bearing $R^1$ is either E or Z.

In still another embodiment of the invention, the compound has the structure of Formula (III').

In still another embodiment, the compound has the structure of Formula (I'); and $R^1$ is —C(=O)—$R^2$.

In yet another embodiment, $R^2$ is $C_{1-6}$ alkyl.

In yet another embodiment, $R^2$ is $C_{3-6}$ cycloalkyl.

In yet another embodiment, $R^2$ is substituted $C_{1-6}$ alkyl; and the substituent group is selected from methyl, hydroxyl, and halogen.

In yet another embodiment, $R^2$ is substituted $C_{3-6}$ cycloalkyl; and the substituent group is selected from methyl, hydroxyl, and halogen.

In still another embodiment, $R^2$ is selected from the group consisting of methyl, ethyl, n-propyl, isopropyl, cyclopropyl, n-butyl, t-butyl, cyclobutyl, isobutyl, 4-methyl-2-pentyl, 2,2-dimethyl-1-butyl, 3,3-dimethyl-1-butyl, 2-ethyl-1-butyl, cyclopentenyl, and tetrahydrofuran, more preferably, $R^2$ is selected from the group consisting of isopropyl, cyclopropyl, cyclobutyl, 4-methyl-2-pentyl, t-butyl, 2,2-dimethyl-1-butyl, 3,3-dimethyl-1-butyl, 2-ethyl-1-butyl,

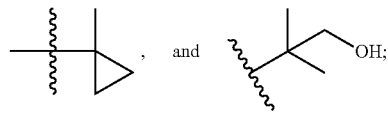

most preferably, $R^2$ is selected from the group consisting of t-butyl, 2,2-dimethyl-1-butyl,

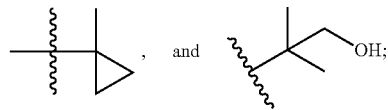

optionally, $R^2$ is selected from the group consisting of 2-methyloxiranyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, n-pentyl, isopentyl, neopentyl, 2,2-dimethylbutanyl, and

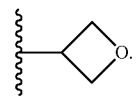

In still another embodiment, $R^1$ is $C_{3-6}$ heterocycloalkyl, of which one or two of the carbon atoms is substituted with a nitrogen atom.

In some embodiments, $R^1$ is $C_{5-6}$ heteroaryl, of which one or two of the carbon atoms is substituted with a nitrogen, or a sulfur atom.

In some embodiments, $R^1$ is $C_6$ heteroaryl, of which one or two of the carbon atoms is substituted with a nitrogen atom; and the one or more substituent groups is selected from —NH$_2$, —OH, halogen and —CN.

In some embodiments, $R^1$ is selected from the group consisting of unsubstituted or substituted

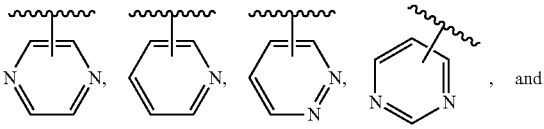

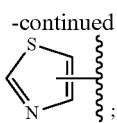

more preferably, $R^1$ is selected from the group consisting of unsubstituted or substituted

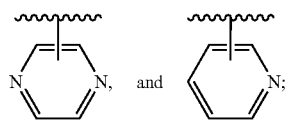

optionally, $R^1$ is selected from the group consisting of unsubstituted or substituted furyl, pyrrolyl, imdazolyl, triazolyl, tetrazolyl, oxazolyl, oxadiazolyl, 1,3,5-triazinyl, thiazolyl, and thienyl.

In some embodiments, $R^1$ is substituted $C_{3-6}$ heterocycloalkyl, of which one or two of the carbon atoms is substituted with a nitrogen atom; and the one or more substituent groups is selected from halogen and —CN.

In some embodiments, $R^1$ is unsubstituted or substituted $C_{5-10}$ heteroaryl, of which one or two of the carbon atoms is substituted with a nitrogen atom; and the one or more substituent groups is selected from halogen and —CN.

In some embodiments, $R^1$ is selected from the group consisting of unsubstituted or substituted

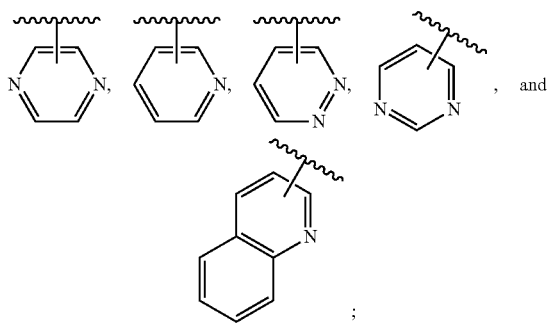

more preferably, $R^1$ is unsubstituted or substituted

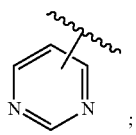

optionally, $R^1$ is selected from unsubstituted or substituted phenyl, naphthyl, furyl, benzofuryl, pyrrolyl, imdazolyl, benzimdazolyl, triazolyl, tetrazolyl, oxazolyl, oxadiazolyl, 1,3,5-triazinyl, thiazolyl, thienyl, benzothienyl, indolyl, purinyl, quinolyl, isoquinolyl and phenoxathiinyl In some embodiments, the compound is a compound of Formula (I'); and $R^1$ is —C(=O)—$R^2$.

In some embodiments, the compound is a compound of Formula (I'); and $R^1$ is $C_6$ heteroaryl wherein one or two carbon atoms and the associated hydrogen atom is replaced with a nitrogen atom.

In some embodiments, $R^3$ and $R^4$ are independently $C_{1-4}$ alkyl, or $R^3$ and $R^4$ together with N which they are attached from $C_{4-10}$ cycloalkylamino ring.

In some embodiments, $R^3$ and $R^4$ together with N which they are attached to form a substituted $C_{4-10}$ cycloalkylamino; and the substituent group is selected from the group consisting of methyl, ethyl, hydroxyl, and halogen.

In some embodiments, $R^3$ and $R^4$ are joined together to form a cycloalkylamino, wherein $C_{4-10}$ cycloalkylamino is selected from the group consisting of

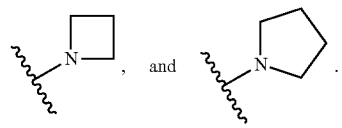 [SMILES: *N1CCC1 ; *N1CCCC1]

In some embodiments, the compound is a compound of Formula (III'); $R^3$ and $R^4$ together with N which they are attached form a substituted cycloalkylamino, and the substituent group is selected from methyl, hydroxyl, and a halogen; and the one or more substituent groups is halogen.

In some embodiments, the compound is selected from a compound of Formula (I'), Formula (II'), and Formula (III').

In the following, the chemical nomenclature is based on ChemDraw Professional 16.0.

In some embodiments, the compound is (Z)-3-(3-(3-(pentafluoro-sulfaneyl)-5-(trifluoromethyl)phenyl)-1H-1,2,4-triazol-1-yl)-N'-(pyrazin-2-yl)acrylohydrazide.

In some embodiments, the compound is (Z)-3-(3-(3-(pentafluoro-sulfaneyl)-5-(trifluoromethyl)phenyl)-1H-1,2,4-triazol-1-yl)-N'-(pyridin-2-yl)acrylohydrazide.

In some embodiments, the compound is (Z)-3-(3-(3-(pentafluoro-sulfaneyl)-5-(trifluoromethyl)phenyl)-1H-1,2,4-triazol-1-yl)-N'-pivaloylacrylohydrazide.

In some embodiments, the compound is (E)-3-(3-(3-(pentafluoro-sulfaneyl)-5-(trifluoromethyl)phenyl)-1H-1,2,4-triazol-1-yl)-2-(pyrimidin-5-yl)acrylamide.

In some embodiments, the compound is (Z)-3-(3-(3-(pentafluoro-sulfaneyl)-5-(trifluoromethyl)phenyl)-1H-1,2,4-triazol-1-yl)-2-(pyrimidin-5-yl)acrylamide.

In some embodiments, the compound is (Z)-3-(3-(3-(pentafluoro-sulfaneyl)-5-(trifluoromethyl)phenyl)-1H-1,2,4-triazol-1-yl)-N'-(thiazol-2-yl)acrylohydrazide.

In some embodiments, the compound is (Z)-N'-(3-(3-(3-(pentafluoro-sulfaneyl)-5-(trifluoromethyl)phenyl)-1H-1,2,4-triazol-1-yl)acryloyl)cyclopropanecarbohydrazide.

In some embodiments, the compound is (Z)-N'-isobutyryl-3-(3-(3-(pentafluoro-sulfaneyl)-5-(trifluoromethyl)phenyl)-1H-1,2,4-triazol-1-yl)acrylohydrazide.

In some embodiments, the compound is (Z)-N'-(3-(3-(3-(pentafluoro-sulfaneyl)-5-(trifluoromethyl)phenyl)-1H-1,2,4-triazol-1-yl)acryloyl)butyrohydrazide.

In some embodiments, the compound is (Z)-N'-(3-(3-(3-(pentafluoro-sulfaneyl)-5-(trifluoromethyl)phenyl)-1H-1,2,4-triazol-1-yl)acryloyl)cyclobutanecarbohydrazide.

In some embodiments, the compound is (Z)-1-methyl-N'-(3-(3-(3-(pentafluoro-sulfaneyl)-5-(trifluoromethyl)phenyl)-1H-1,2,4-triazol-1-yl)acryloyl)cyclopropane-1-carbohydrazide.

In some embodiments, the compound is (Z)-N'-(3-chloro-2-(hydroxymethyl)-2-methylpropanoyl)-3-(3-(3-(pentafluoro-sulfaneyl)-5-(trifluoromethyl)phenyl)-1H-1,2,4-triazol-1-yl)acrylohydrazide.

In some embodiments, the compound is (Z)-3-methyl-N'-(3-(3-(3-(pentafluoro-sulfaneyl)-5-(trifluoromethyl)phenyl)-1H-1,2,4-triazol-1-yl)acryloyl)butanehydrazide.

In some embodiments, the compound is (Z)-N'-acetyl-3-(3-(3-(pentafluoro-sulfaneyl)-5-(trifluoromethyl)phenyl)-1H-1,2,4-triazol-1-yl)acrylohydrazide.

In some embodiments, the compound is (Z)-3-(3-(3-(pentafluoro-sulfaneyl)-5-(trifluoromethyl)phenyl)-1H-1,2,4-triazol-1-yl)-N'-propionylacrylohydrazide.

In some embodiments, the compound is (Z)-N'-(3-(3-(3-(pentafluoro-sulfaneyl)-5-(trifluoromethyl)phenyl)-1H-1,2,4-triazol-1-yl)acryloyl)cyclopentanecarbohydrazide.

In some embodiments, the compound is (Z)-N'-(2-methyl-2-(methyl-d3)propanoyl-3,3,3-d3)-3-(3-(3-(pentafluoro-sulfaneyl)-5-(trifluoromethyl)phenyl)-1H-1,2,4-triazol-1-yl)acrylohydrazide.

In some embodiments, the compound is (Z)-3-(3-(3-(difluoromethyl)-5-(pentafluoro-sulfaneyl)phenyl)-1H-1,2,4-triazol-1-yl)-N'-(pyrazin-2-yl)acrylohydrazide.

In some embodiments, the compound is (Z)-3-(3-(3-(difluoromethyl)-5-(pentafluoro-sulfaneyl)phenyl)-1H-1,2,4-triazol-1-yl)-N'-(pyridin-2-yl)acrylohydrazide.

In some embodiments, the compound is (Z)-3-(3-(3-(difluoromethyl)-5-(pentafluoro-sulfaneyl)phenyl)-1H-1,2,4-triazol-1-yl)-N'-pivaloylacrylohydrazide.

In some embodiments, the compound is (Z)-3-(3-(3-(pentafluoro-sulfaneyl)-5-(trifluoromethyl)phenyl)-1H-1,2,4-triazol-1-yl)-N'-(pyridazin-3-yl)acrylohydrazide.

In some embodiments, the compound is (Z)-N'-(2-hydroxy-2-methylpropanoyl)-3-(3-(3-(pentafluoro-sulfaneyl)-5-(trifluoromethyl)phenyl)-1H-1,2,4-triazol-1-yl)acrylohydrazide.

In some embodiments, the compound is (Z)-N'-(2-fluoro-2-methylpropanoyl)-3-(3-(3-(pentafluoro-sulfaneyl)-5-(trifluoromethyl)phenyl)-1H-1,2,4-triazol-1-yl)acrylohydrazide.

In some embodiments, the compound is (Z)-1-hydroxy-N'-(3-(3-(3-(pentafluoro-sulfaneyl)-5-(trifluoromethyl)phenyl)-1H-1,2,4-triazol-1-yl)acryloyl)cyclopropane-1-carbohydrazide.

In some embodiments, the compound is (Z)-N'-(3-(3-(3-(pentafluoro-sulfaneyl)-5-(trifluoromethyl)phenyl)-1H-1,2,4-triazol-1-yl)acryloyl)tetrahydrofuran-3-carbohydrazide.

In some embodiments, the compound is (Z)-N'-(3-(3-(3-(pentafluoro-sulfaneyl)-5-(trifluoromethyl)phenyl)-1H-1,2,4-triazol-1-yl)acryloyl)tetrahydrofuran-2-carbohydrazide.

In some embodiments, the compound is (Z)-3-methyl-N'-(3-(3-(3-(pentafluoro-sulfaneyl)-5-(trifluoromethyl)phenyl)-1H-1,2,4-triazol-1-yl)acryloyl)oxetane-3-carbohydrazide.

In some embodiments, the compound is (Z)-1-methyl-N'-(3-(3-(3-(pentafluoro-sulfaneyl)-5-(trifluoromethyl)phenyl)-1H-1,2,4-triazol-1-yl)acryloyl)pyrrolidine-3-carbohydrazide.

In some embodiments, the compound is (E)-2-(2-fluoropyrimidin-5-yl)-3-(3-(3-(pentafluoro-sulfaneyl)-5-(trifluoromethyl)phenyl)-1H-1,2,4-triazol-1-yl)acrylamide.

In some embodiments, the compound is (E)-2-(2-fluoropyridin-4-yl)-3-(3-(3-(pentafluoro-sulfaneyl)-5-(trifluoromethyl)phenyl)-1H-1,2,4-triazol-1-yl)acrylamide.

In some embodiments, the compound is (E)-2-(5-cyanopyridin-3-yl)-3-(3-(3-(pentafluoro-sulfaneyl)-5-(trifluoromethyl)phenyl)-1H-1,2,4-triazol-1-yl)acrylamide.

In some embodiments, the compound is (E)-3-(3-(3-(pentafluoro-sulfaneyl)-5-(trifluoromethyl)phenyl)-1H-1,2,4-triazol-1-yl)-2-(quinolin-3-yl)acrylamide.

Still another aspect of this invention is the provision of compounds, compositions, kits, and antidotes for modulating XPO1 activities in mammals, wherein such a compound is selected from the group consisting of:

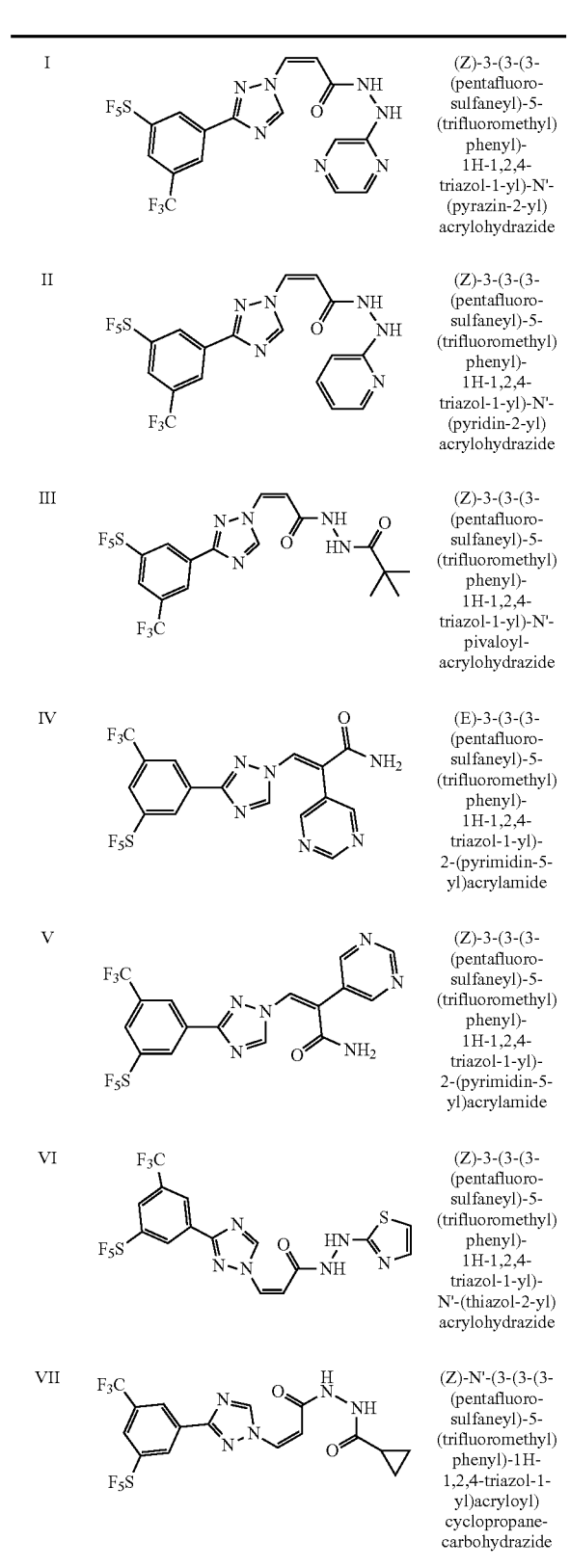

| | | |
|---|---|---|
| I | | (Z)-3-(3-(3-(pentafluoro-sulfaneyl)-5-(trifluoromethyl)phenyl)-1H-1,2,4-triazol-1-yl)-N'-(pyrazin-2-yl)acrylohydrazide |
| II | | (Z)-3-(3-(3-(pentafluoro-sulfaneyl)-5-(trifluoromethyl)phenyl)-1H-1,2,4-triazol-1-yl)-N'-(pyridin-2-yl)acrylohydrazide |
| III | | (Z)-3-(3-(3-(pentafluoro-sulfaneyl)-5-(trifluoromethyl)phenyl)-1H-1,2,4-triazol-1-yl)-N'-pivaloylacrylohydrazide |
| IV | | (E)-3-(3-(3-(pentafluoro-sulfaneyl)-5-(trifluoromethyl)phenyl)-1H-1,2,4-triazol-1-yl)-2-(pyrimidin-5-yl)acrylamide |
| V | | (Z)-3-(3-(3-(pentafluoro-sulfaneyl)-5-(trifluoromethyl)phenyl)-1H-1,2,4-triazol-1-yl)-2-(pyrimidin-5-yl)acrylamide |
| VI | | (Z)-3-(3-(3-(pentafluoro-sulfaneyl)-5-(trifluoromethyl)phenyl)-1H-1,2,4-triazol-1-yl)-N'-(thiazol-2-yl)acrylohydrazide |
| VII | | (Z)-N'-(3-(3-(3-(pentafluoro-sulfaneyl)-5-(trifluoromethyl)phenyl)-1H-1,2,4-triazol-1-yl)acryloyl)cyclopropane-carbohydrazide |

| | | |
|---|---|---|
| VIII | | (Z)-N'-isobutyryl-3-(3-(3-(pentafluorosulfaneyl)-5-(trifluoromethyl)phenyl)-1H-1,2,4-triazol-1-yl)acrylohydrazide |
| IX | | (Z)-N'-(3-(3-(3-(pentafluorosulfaneyl)-5-(trifluoromethyl)phenyl)-1H-1,2,4-triazol-1-yl)acryloyl)butyrohydrazide |
| X | | (Z)-N'-(3-(3-(3-(pentafluorosulfaneyl)-5-(trifluoromethyl)phenyl)-1H-1,2,4-triazol-1-yl)acryloyl)cyclobutanecarbohydrazide |
| XI | | (Z)-1-methyl-N-(3-(3-(3-(pentafluorosulfaneyl)-5-(trifluoromethyl)phenyl)-1H-1,2,4-triazol-1-yl)acryloyl)cyclopropane-1-carbohydrazide |
| XII | | (Z)-N'-(3-chloro-2-(hydroxymethyl)-2-methyl-propanoyl)-3-(3-(3-(pentafluorosulfaneyl)-5-(trifluoromethyl)phenyl)-1H-1,2,4-triazol-1-yl)acrylohydrazide |
| XIII | | (Z)-3-methyl-N'-(3-(3-(3-(pentafluorosulfaneyl)-5-(trifluoromethyl)phenyl)-1H-1,2,4-triazol-1-yl)acryloyl)butanehydrazide |
| XIV | | (Z)-N'-acetyl-3-(3-(3-(pentafluorosulfaneyl)-5-(trifluoromethyl)phenyl)-1H-1,2,4-triazol-1-yl)acrylohydrazide |
| XV | | (Z)-3-(3-(3-(pentafluorosulfaneyl)-5-(trifluoromethyl)phenyl)-1H-1,2,4-triazol-1-yl)-N'-propionyl-acrylohydrazide |
| XVI | | (Z)-N'-(3-(3-(3-(pentafluorosulfaneyl)-5-(trifluoromethyl)phenyl)-1H-1,2,4-triazol-1-yl)acryloyl)cyclopentane-carbohydrazide |
| XVII | | (Z)-N'-(2-methyl-2-(methyl-d3)propanoyl-3,3,3-d3)-3-(3-(3-(pentafluorosulfaneyl)-5-(trifluoromethyl)phenyl)-1H-1,2,4-triazol-1-yl)acrylohydrazide |
| XVIII | | (Z)-3-(3-(3-(difluoromethyl)-5-4-(pentafluorosulfaneyl)phenyl)-1H-1,2,4-triazol-1-yl)-N'-(pyrazin-2-yl)acrylohydrazide |
| XIV | | (Z)-3-(3-(3-(difluoromethyl)-5-(pentafluorosulfaneyl)phenyl)-1H-1,2,4-triazol-1-yl)-N'-(pyridin-2-yl)acrylohydrazide |
| XV | | (Z)-3-(3-(3-(difluoromethyl)-5-4-(pentafluorosulfaneyl)phenyl)-1H-1,2,4-triazol-1-yl)-N'-pivaloyl-acrylohydrazide |
| XVI | | (Z)-3-(3-(3-(pentafluorosulfaneyl)-5-(trifluoromethyl)phenyl)-1H-1,2,4-triazol-1-yl)-N'-(pyridazin-3-yl)acrylohydrazide |

| | | |
|---|---|---|
| XVII | (structure) | (Z)-N'-(2-hydroxy-2-methylpropanoyl)-3-(3-(3-(pentafluoro-sulfaneyl)-5-(trifluoromethyl)phenyl)-1H-1,2,4-triazol-1-yl)acrylohydrazide |
| XVIII | (structure) | (Z)-N'-(2-fluoro-2-methyl-propanoyl)-3-(3-(3-(pentafluoro-sulfaneyl)-5-(trifluoromethyl)phenyl)-1H-1,2,4-triazol-1-yl)acrylohydrazide |
| XIX | (structure) | (Z)-1-hydroxy-N'-(3-(3-(3-(pentafluoro-sulfaneyl)-5-(trifluoromethyl)phenyl)-1H-1,2,4-triazol-1-yl)acryloyl)cyclopropane-1-carbohydrazide |
| XX | (structure) | (Z)-N'-(3-(3-(3-(pentafluoro-sulfaneyl)-5-(trifluoromethyl)phenyl)-1H-1,2,4-triazol-1-yl)acryloyl)tetrahydrofuran-3-carbohydrazide |
| XXI | (structure) | (Z)-N'-(3-(3-(3-(pentafluoro-sulfaneyl)-5-(trifluoromethyl)phenyl)-1H-1,2,4-triazol-1-yl)acryloyl)tetrahydrofuran-2-carbohydrazide |
| XXII | (structure) | (Z)-3-methyl-N'-(3-(3-(3-(pentafluoro-sulfaneyl)-5-(trifluoromethyl)phenyl)-1H-1,2,4-triazol-1-yl)acryloyl)oxetane-3-carbohydrazide |
| XXIII | (structure) | (Z)-1-methyl-N'-(3-(3-(3-(pentafluoro-sulfaneyl)-5-(trifluoromethyl)phenyl)-1H-1,2,4-triazol-1-yl)acryloyl)pyrrolidine-3-carbohydrazide |
| XXIV | (structure) | (E)-2-(2-fluoropyrimidin-5-yl)-3-(3-(3-(pentafluoro-sulfaneyl)-5-(trifluoromethyl)phenyl)-1H-1,2,4-triazol-1-yl)acrylamide |
| XXV | (structure) | (E)-2-(2-fluoropyridin-4-yl)-3-(3-(3-(pentafluoro-sulfaneyl)-5-(trifluoromethyl)phenyl)-1H-1,2,4-triazol-1-yl)acrylamide |
| XXVI | (structure) | (E)-2-(5-cyanopyridin-3-yl)-3-(3-(3-(pentafluoro-sulfaneyl)-5-(trifluoromethyl)phenyl)-1H-1,2,4-triazol-1-yl)acrylamide |
| XXVII | (structure) | (E)-3-(3-(3-(pentafluoro-sulfaneyl)-5-(trifluoromethyl)phenyl)-1H-1,2,4-triazol-1-yl)-2-(quinolin-3-yl)acrylamide |

A compound provided by the present disclosure can have the structure of Formula (I'):

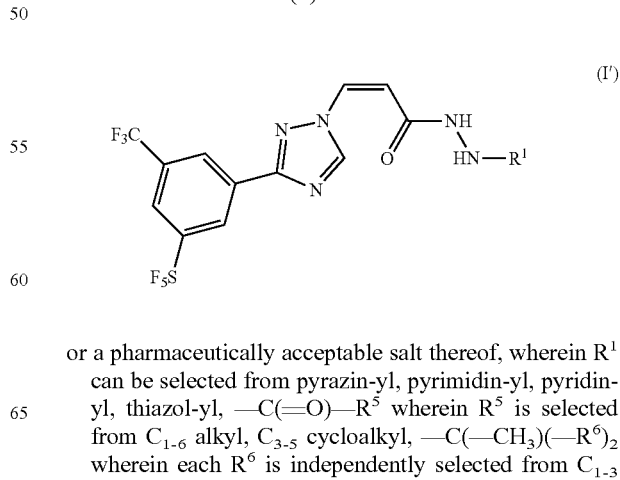

or a pharmaceutically acceptable salt thereof, wherein $R^1$ can be selected from pyrazin-yl, pyrimidin-yl, pyridin-yl, thiazol-yl, —C(=O)—$R^5$ wherein $R^5$ is selected from $C_{1-6}$ alkyl, $C_{3-5}$ cycloalkyl, —C(—$CH_3$)(—$R^6$)$_2$ wherein each $R^6$ is independently selected from $C_{1-3}$ alkyl and substituted $C_{1-3}$ alkyl, or each $R^6$ together with the geminal carbon atom form a $C_{3-6}$ cycloalkyl ring.

In a compound of Formula (I'), each substituent is independently selected from, for example, —OH, —Cl, and $C_{1-4}$ alkyl.

In a compound of Formula (I'), $R^1$ can be pyrazin-yl,
In a compound of Formula (I'), $R^1$ can be pyrazin-2-yl.
In a compound of Formula (I'), $R^1$ can be pyrimidin-yl.
In a compound of Formula (I'), $R^1$ can be selected from pyrimidin-2-yl, pyrimidin-4-yl, and pyrimidin-5-yl.
In a compound of Formula (I'), $R^1$ can be pyridin-yl.
In a compound of Formula (I'), $R^1$ is selected from pyridin-2-yl, pyridin-3-yl, and pyridin-4-yl.
In a compound of Formula (I'), $R^1$ is thiazol-yl.
In a compound of Formula (I'), $R^1$ is thiazol-2-yl.
In a compound of Formula (I'), $R^1$ can be —C(=O)—$R^5$.
In a compound of Formula (I'), $R^5$ can be $C_{1-6}$ alkyl.
In a compound of Formula (I'), $R^5$ can be selected from methyl, ethyl, n-propyl, iso-propyl, n-butyl, iso-butyl, sec-butyl, and tert-butyl.
In a compound of Formula (I'), $R^5$ can be $C_{3-5}$ alkyl.
In a compound of Formula (I'), $R^5$ can be selected from cyclopropyl, cyclobutyl, cyclopentyl, and cyclohexyl.
In a compound of Formula (I'), $R^1$ can be —C(—$CH_3$)(—$R^6$)$_2$ wherein each $R^6$ can be independently selected from $C_{1-3}$ alkyl and substituted $C_{1-3}$ alkyl.
In a compound of Formula (I'), each $R^6$ can be independently selected from —$CH_2$—$R^7$.
In a compound of Formula (I'), each $R^7$ can be independently selected from, for example, —OH, —Cl, and $C_{1-4}$ alkyl.
In a compound of Formula (I'), each $R^6$ together with the geminal carbon atom can form a $C_{3-6}$ cycloalkyl ring.
In a compound of Formula (I'), each $R^6$ together with the geminal carbon atom can form a cyclopropyl ring, a cyclobutyl ring, a cyclopentyl ring, or a cyclohexyl ring.

A compound provided by the present disclosure can have the structure of Formula (II'):

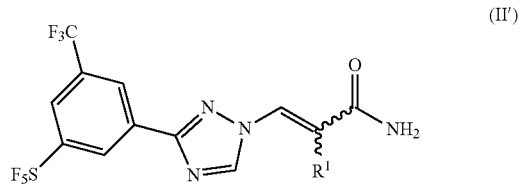

(II')

or a pharmaceutically acceptable salt thereof, wherein $R^1$ can be selected from pyrazin-yl, pyrimidin-yl, and pyridin-yl.

In a compound of Formula (II'), $R^1$ can be pyrazin-2-yl.
In a compound of Formula (II'), $R^1$ can be selected from pyrimidin-2-yl, pyrimidin-4-yl, and pyrimidin-5-yl.
In a compound of Formula (II'), $R^1$ can be selected from pyridin-2-yl, pyridin-3-yl, and pyridin-4-yl.
In a compound of Formula (II'), the double bond to which $R^1$ is bonded is in the E configuration.
In a compound of Formula (II'), the double bond to which $R^1$ is bonded is in the Z configuration.

A compound provided by the present disclosure can be (Z)-3-(3-(3,5-bis(trifluoromethyl)phenyl)-1H-1,2,4-triazol-1-yl)-2-(pyrimidin-5-yl)acrylamide (XXIV) having the structure:

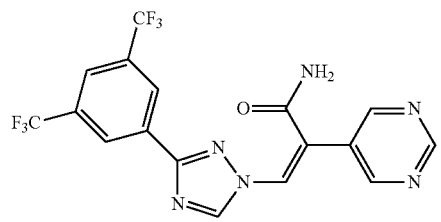 [SMILES: NC(=O)/C(=C\n1cnc(-c2cc(C(F)(F)F)cc(C(F)(F)F)c2)n1)c1cncnc1]

An aspect of the present invention concerns compounds disclosed herein.

An aspect of the present invention concerns the preparation methods for compounds disclosed herein.

In some embodiments, there provides a preparation method for certain compounds having the general Formula (I'-III') or certain compounds (I-XXVII) shown above, which comprises the steps of:

(a) providing a compound of Formula A:

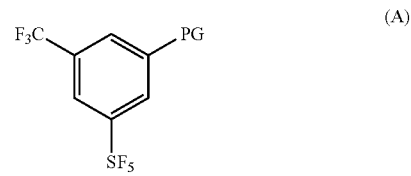

(A)

wherein PG is halogen (Cl, Br, I), CN, $N_3$, $NH_2$, —COO—$C_{1-6}$ alkyl, $C_{2-6}$ alkene, $C_{2-6}$ alkene-aryl.

(b) reacting said compound of formula A with an appropriate reagent or reagents to form a compound of Formula B:

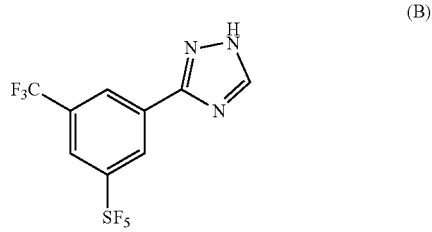

(B)

(c) reacting the reaction product according to Step (b) with a compound of Formula C to form a compound of Formula D:

(C)

(D)

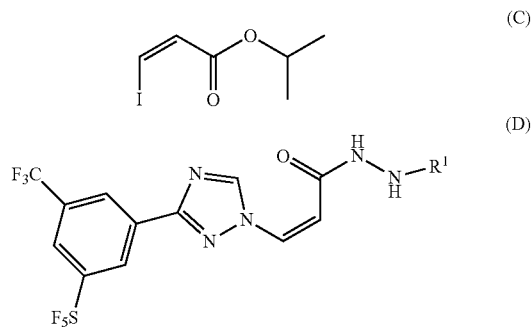

wherein, $R^1$ is defined above for the compound of Formula (I'), (II') or (III').

In some embodiments, there provides a preparation method for preparing the compound of Formula A, which comprises the steps of:
(a) providing a compound of Formula M:

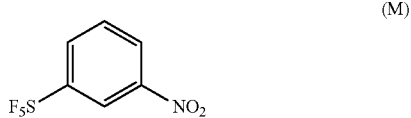

(M)

(b) reacting said compound of formula M with suitable reagents to form a compound of Formula N:

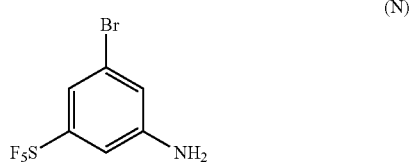

(N)

(c) reacting the reaction product according to Step (b) with suitable reagents to form a compound of Formula J:

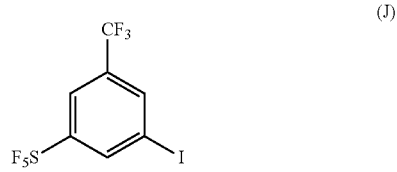

(J)

(d) reacting the reaction product according to Step (c) with suitable reagents to form a compound of Formula K.

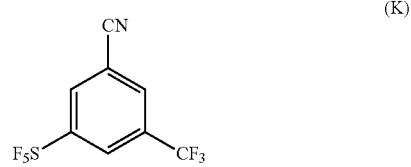

(K)

An aspect of the present invention concerns compounds which are or can be modulators of dysfunctional XPO1 activities.

An aspect of the present invention concerns the use of a modulator of dysfunctional XPO1 activities for the preparation of a medicament used in the treatment, prevention, inhibition or elimination of tumors.

An aspect of the present invention concerns the use of a modulator of dysfunctional XPO1 activities for the preparation of a medicament used in the treatment, prevention, inhibition or elimination of a disorder or disease or medical condition in a patient by modulating dysfunctional XPO1 activities in said patient.

The present invention also describes one or more methods of synthesizing the compounds of the present invention.

The invention also describes one or more uses of the compounds of the present invention.

The invention also describes one or more uses of the compounds of the present invention with an adjunctive agent such as use with tumor necrosis factor (TNF), granulocyte colony-stimulating factor (GCSF) or other chemotherapeutic agents.

The present invention also describes one or more methods of preparing various pharmaceutical compositions comprising the compounds of the present invention.

The invention also describes one or more uses of the various pharmaceutical compositions of the present invention for the preparation of a medicament used in the treatment, prevention, inhibition or elimination of a disorder or disease or medical condition in a patient by modulating dysfunctional XPO1 activities in said patient.

The present invention provides a pharmaceutical composition comprising compounds of the present invention, e.g., example compounds. According to the specific examples of the present invention, the pharmaceutical composition can further comprise pharmaceutically acceptable excipient, carrier, adjuvant, solvent and a combination thereof.

The present invention provides a method of treating, preventing or ameliorating a disease or disorder, comprising administrating a safe and effective amount of a combination of drugs containing compounds of the invention and one or more therapeutic active agents. Among them, the combination of drugs comprises one or more additional drugs for treatment of a cancer.

The amount of the compound of the pharmaceutical composition disclosed herein refers to an amount which can be effectively detected to modulate dysfunctional XPO1 activities of biology samples and in a patient. The active ingredient may be administered to subjects in need of such treatment in dosage that will provide optimal pharmaceutical efficacy, which is not limited to the desired therapeutic effects, on the route of administration, and on the duration of the treatment. The dosage will vary from patient to patient depending upon the nature and severity of disease, the patient's weight, special diet then being followed by a patient, concurrent medication, and other factors which those skilled in the art will recognize. The quantity of active compound in a unit dose of preparation may be varied or adjusted from about 1 mg to about 1000 mg, preferably from about 1 mg to about 500 mg, more preferably from about 1 mg to about 250 mg, still more preferably from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required. The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 200 mg/day, preferably 10 mg/day to 100 mg/day, which may be administered in single or multiple doses. In yet another embodiment about 1 mg to 50 mg per patient per day.

It will also be appreciated that certain of the compounds of the present invention can exist in free form for treatment, or where appropriate, as a pharmaceutically acceptable derivative or a prodrug thereof. A pharmaceutically acceptable derivative includes pharmaceutically acceptable salts, esters, salts of such esters, or any other adduct or derivative which upon administration to a patient in need thereof provide, directly or indirectly, a compound as otherwise described herein, or an therapeutically effective metabolite or residue thereof.

The pharmaceutical compositions of the invention may be prepared and packaged in bulk form wherein a safe and effective amount of a compound of Formula (I-V) disclosed herein can be extracted and then given to the patient, such as with powders or syrups. Generally, dosage levels of between 0.0001 to 10 mg/kg of body weight daily are administered to the patient to obtain effective modulation of dysfunctional XPO1 activities. Alternatively, the pharmaceutical compositions of the invention may be prepared and packaged in unit dosage form wherein each physically discrete unit contains a safe and effective amount of a compound of Formula (XPO1 activities) disclosed herein. When prepared in unit dosage form, the pharmaceutical compositions of the invention commonly contain from about 0.5 mg to 1 g, or 1 mg to 700 mg, or 5 mg to 100 mg, or more preferably, 25 mg to 60 mg of the compound of the invention.

When the pharmaceutical compositions of the present invention also contain one or more other active ingredients, in addition to a compound of the present invention, the weight ratio of the compound of the present invention to the second active ingredient may be varied and depend upon the effective dose of each ingredient. Thus, for example, when a compound of the present invention is combined with another agent, the weight ratio of the compound of the present invention to the other agent will generally range from about 1000:1 to about 1:1000, such as about 200:1 to 1:200. Combinations of a compound of the present invention and other active ingredients will generally also be within the aforementioned range, but in each case, an effective dose of each active ingredient in the combination should be used.

"Pharmaceutically acceptable excipient" as used herein means a pharmaceutically acceptable material, composition or vehicle involved in giving form or consistency to the pharmaceutical composition. Each excipient must be compatible with the other ingredients of the pharmaceutical composition when commingled, such that interactions which would substantially reduce the efficacy of the compound of the invention when administered to a patient and would result in pharmaceutically unacceptable compositions. In addition, each excipient must of course be of sufficiently high purity to render it pharmaceutically acceptable.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound of the present invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are resources that are available to the skilled artisan that describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

In Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

The pharmaceutical compositions of the invention are prepared using techniques and methods known to those skilled in the art. Some of the methods commonly used in the art are described in *Remington's Pharmaceutical Sciences* (Mack Publishing Company).

Therefore, another aspect of the present invention is related to a method for preparing a pharmaceutical composition. The pharmaceutical composition contains the compound disclosed herein and pharmaceutically acceptable excipient, carrier, adjuvant, vehicle or a combination thereof, the method comprises mixing various ingredients. The pharmaceutical composition containing the compound disclosed herein can be prepared for example at normal ambient temperature and pressure.

The compound of the invention will typically be formulated into a dosage form adapted for administration to the patient by the desired route of administration. For example, dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols, solutions, and dry powders; and (6) topical administration such as creams, ointments, lotions, solutions, pastes, sprays, foams, and gels.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric coatings include, but are not limited to, fatty acids, fats, phenylsalicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and ascorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl)acetal of a lower alkyl aldehyde, e.g., acetaldehyde diethyl acetal; and a water-miscible solvent having one or more hydroxy groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient (s) provided herein, and a dialkylated mono- or polyalkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfate, sodium metabisulfite, thiodipropionic acid and its esters, and dithiocarbamates.

Where appropriate, dosage unit formulations for oral administration can be microencapsulated. The formulation can also be prepared to prolong or sustain the release as for example by coating or embedding particulate material in polymers, wax, or the like.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all above dosage forms.

The compounds disclosed herein can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, polyepsilon-caprolactone, polyhydroxybutyric acid, polyorthoesters, polyacetals, polydihydroxypyrans, polycyanoacrylates and crosslinked or amphipathic block copolymers of hydrogels.

The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

The pharmaceutical compositions provided herein may be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, Remington: The Science and Practice of Pharmacy, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfate and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80 and triethanolamine oleate. Suitable sequestering or chelating agents include, but are not limited to, EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a sterile vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

In other aspect, the pharmaceutical composition of the invention is prepared to a dosage form adapted for administration to a patient by inhalation, for example as a dry powder, an aerosol, a suspension, or a solution composition. In one embodiment, the invention is directed to a dosage form adapted for administration to a patient by inhalation as a dry powder. In one embodiment, the invention is directed to a dosage form adapted for administration to a patient by inhalation as a dry powder. Dry powder compositions for delivery to the lung by inhalation typically comprise a compound disclosed herein or a pharmaceutically acceptable salt thereof as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides. The finely divided powder may be prepared by, for example, micronization and milling. Generally, the size-reduced (e.g., micronized) compound can be defined by a $D_{50}$ value of about 1 to about 10 microns (for example as measured using laser diffraction).

Aerosols may be formed by suspending or dissolving a compound disclosed herein or a pharmaceutically acceptable salt thereof in a liquified propellant. Suitable propellants include halocarbons, hydrocarbons, and other liquefied gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of formula (A) or a pharmaceutically acceptable salt thereof will typically be administered to a patient via a metered dose inhaler (MDI). Such devices are known to those skilled in the art.

The aerosol may contain additional pharmaceutically acceptable excipients typically used with MDIs such as surfactants, lubricants, cosolvents and other excipients to improve the physical stability of the formulation, to improve valve performance, to improve solubility, or to improve taste.

Pharmaceutical compositions adapted for transdermal administration may be presented as discrete patches intended to remain in intimate contact with the epidermis of the patient for a prolonged period of time. For example, the active ingredient may be delivered from the patch by iontophoresis as generally described in *Pharmaceutical Research,* 3(6), 318 (1986).

Pharmaceutical compositions adapted for topical administration may be formulated as ointments, creams, suspensions, lotions, powders, solutions, pastes, gels, sprays, aerosols or oils. Ointments, creams and gels, may, for example, be formulated with an aqueous or oily base with the addition of suitable thickening and/or gelling agent and/or solvents. Such bases may thus, for example, include water and/or an oil such as liquid paraffin or a vegetable oil such as *arachis* oil or castor oil, or a solvent such as polyethylene glycol. Thickening agents and gelling agents which may be used according to the nature of the base include soft paraffin, aluminum stearate, cetostearyl alcohol, polyethylene glycols, wool fat, beeswax, carboxypolymethylene and cellulose derivatives, and/or glyceryl monostearate and/or nonionic emulsifying agents.

Lotions may be formulated with an aqueous or oily base and will in general also contain one or more emulsifying agents, stabilizing agents, dispersing agents, suspending agents or thickening agents.

Powders for external application may be formed with the aid of any suitable powder base, for example, talc, lactose or starch. Drops may be formulated with an aqueous or nonaqueous base also comprising one or more dispersing agents, solubilizing agents, suspending agents or preservatives.

Topical preparations may be administered via one or more applications per day to the affected area; over skin areas occlusive dressings may advantageously be used. Continuous or prolonged delivery may be achieved via an adhesive reservoir system.

Compounds or pharmaceutical compositions of the invention disclosed herein can be used in the manufacture of a medicament for treating, preventing, ameliorating or mitigating a disorder or disease or a cancer in a subject, as well as other medicaments for modulating (e.g., blocking) dysfunctional XPO1 activities, and the compounds of this invention have superior pharmacokinetic and pharmacodynamic properties, fewer toxic side-effect.

Specifically, the amount of the compound of compositions of the present invention can effectively and detectably modulate dysfunctional XPO1 activities. The compounds or pharmaceutical compositions of the invention may be used for preventing, treating or alleviating diseases relating to dysfunctional XPO1 activities.

A compound provided by the present disclosure can be used to treat a neurological disease or disorder such as, for example, amyotrophic lateral sclerosis, epilepsy, traumatic brain injuries, Huntington's disease, Parkinson's disease, rheumatoid arthritis, systemic lupus erythematosus.

A compound provided by the present disclosure can be used to treat cancer such as, for example, lymphoma, liposarcoma, multiple myeloma, myelodysplastic syndrome, prostate cancer, colorectal cancer, endometrial cancer, pancreatic cancer, gastric cancer, diffuse large B-cell lymphoma, non-small cell lung cancer, ovarian carcinoma, breast cancer, acute myeloid leukemia, thymoma, esophageal cancer, glioblastoma, and other solid tumors.

A compound provided by the present disclosure can be used to treat acute lymphoblastic leukemia, acute myelogenous leukemia, acute myeloid leukemia, advanced thymic epithelial tumor, breast cancer, cervical carcinoma, chronic myeloid leukemia, colorectal neoplasm, coronavirus infection, cutaneous T-cell lymphoma, diffuse large B-cell lymphoma, endometrial carcinoma, gastric cancer, glioblastoma, glioma, hematological malignancies, leukemia, liposarcoma, melanoma, multiple myeloma, myelodysplastic syndrome, neuroendocrine carcinoma, non-small cell lung cancer, ovarian carcinoma, peripheral T-cell lymphoma, prostate cancer, solid tumors, squamous cell carcinoma, or thymoma.

In one embodiment, the therapies disclosed herein comprise administrating a safe and effective amount of the compound of the invention or the pharmaceutical composition containing the compound of the invention to patients in need. Each example disclosed herein comprises the method of treating the diseases above comprising administrating a safe and effective amount of the compound of the invention or the pharmaceutical composition containing the compound of the invention to patients in need.

In one embodiment, the compound of the invention or the pharmaceutical composition thereof may be administered by any suitable route of administration, including both systemic administration and topical administration. Systemic administration includes oral administration, parenteral administration, transdermal administration and rectal administration. Parenteral administration refers to routes of administration other than enteral or transdermal and is typically by injection or infusion. Parenteral administration includes intravenous, intramuscular, and subcutaneous injection or infusion. Topical administration includes application to the skin as well as intraocular, intravaginal, inhaled and intranasal administration. In one embodiment, the compound of the invention or the pharmaceutical composition thereof may be administered orally. In another embodiment, the compound of the invention or the pharmaceutical composition thereof may be administered by inhalation. In a further embodiment, the compound of the invention or the pharmaceutical composition thereof may be administered intranasal.

In one embodiment, the compound of the invention or the pharmaceutical composition thereof may be administered once or according to a dosing regimen wherein multiple doses are administered at varying intervals of time for a given period of time. For example, doses may be administered one, two, three, or four times per day. In one embodiment, a dose is administered once per day. In a further embodiment, a dose is administered twice per day. Doses may be administered until the desired therapeutic effect is achieved or indefinitely to maintain the desired therapeutic effect. Suitable dosing regimens for the compound of the invention or the pharmaceutical composition thereof depend on the pharmacokinetic properties of that compound, such as its absorption, distribution, and half-lives of metabolism and elimination, which can be determined by the skilled artisan. In addition, suitable dosing regimens, including the duration such regimens are administered, for the compound of the invention or the pharmaceutical composition thereof depend on the disorder being treated, the severity of the disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's tolerance to the dosing regimen or over time as individual patient needs change.

The compounds of the present invention may be administered either simultaneously with, or before or after, one or more other therapeutic agents. The compounds of the present invention may be administered separately, by the same or different route of administration, or together in the same pharmaceutical composition as the other agents.

The pharmaceutical composition or combination of the present invention can be in unit dosage of about 1-1000 mg of active ingredients for a subject of about 50-70 kg, preferably about 1-500 mg or about 1-250 mg or about 1-150 mg or about 0.5-100 mg or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties can be correlated with in vitro and in vivo tests using advantageously mammals, e.g., mice, rats, dogs, non-human primates, such as monkeys or isolated organs, tissues and preparations thereof. The compounds of the present invention can be applied in vitro in the form of solutions, e.g., preferably aqueous solutions, and in vivo via topically, inhalation, enterally or parenterally, advantageously intravenously, e.g., as a suspension or in aqueous solution.

In one embodiment, a therapeutically effective dosage of the compound disclosed herein from about 0.1 mg to about 1,000 mg per day. The pharmaceutical compositions should provide a dosage of from about 0.1 mg to about 1,000 mg of the compound. In a special embodiment, pharmaceutical dosage unit forms are prepared to provide from about 1 mg to about 1,000 mg, about 10 mg to about 500 mg, about 20 mg to about 200 mg, about 25 mg to about 100 mg, or about 30 mg to about 60 mg of the active ingredient or a combination of essential ingredients per dosage unit form. In a special embodiment, pharmaceutical dosage unit forms are prepared to provide about 1 mg, 5 mg, 10 mg, 20 mg, 25 mg, 50 mg, 100 mg, 250 mg, 500 mg, 1000 mg of the active ingredient.

The following examples are provided so that the invention might be more fully understood. However, it should be understood that these embodiments merely provide a method of practicing the present invention, and the present invention is not limited to these embodiments.

Generally, the compounds disclosed herein may be prepared by methods described herein, wherein the substituents are as defined for Formula (I'-III') above, except where further noted. The following non-limiting schemes and examples are presented to further exemplify the invention.

Professionals skilled in the art will recognize that the chemical reactions described may be readily adapted to prepare a number of other compounds disclosed herein, and alternative methods for preparing the compounds disclosed herein are deemed to be within the scope disclosed herein. Those having skill in the art will recognize that the starting materials may be varied and additional steps employed to produce compounds encompassed by the present inventions, as demonstrated by the following examples. In some cases, protection of certain reactive functionalities may be necessary to achieve some of the above transformations. In general, such need for protecting groups, as well as the conditions necessary to attach and remove such groups, will be apparent to those skilled in the art of organic synthesis. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, the known reaction conditions or the reaction disclosed in the present invention will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated.

Preparation of Compounds

Compounds of the present invention, including salts, esters, hydrates, or solvates thereof, can be prepared using any known organic synthesis techniques and can be synthesized according to any of numerous possible synthetic routes.

The reactions for preparing compounds of the present invention can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by a skilled artisan.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) (*Preparative LC-MS Purification: Improved Compound Specific Method Optimization* Karl F. Blom, Brian Glass, Richard Sparks, Andrew P. Combs, *J. Combi. Chem.* 2004, 6(6), 874-883, which is incorporated herein by reference in its entirety) and normal phase silica chromatography.

Compounds of the present invention can be synthesized using the methods described below, together with synthetic methods known in the art of synthetic organic chemistry, or variations thereon as appreciated by those skilled in the art. Preferred methods include but are not limited to those methods described below. Specifically, the compounds of the present invention of Formula (A) can be synthesized by following the steps outlined in the exemplary general synthetic schemes listed below, and the abbreviations for the reactants or for the chemical groups of the reactants included in the synthetic schemes are defined in the Examples.

Scheme 1: The following reaction sequence is used to synthesize compounds of structure A1

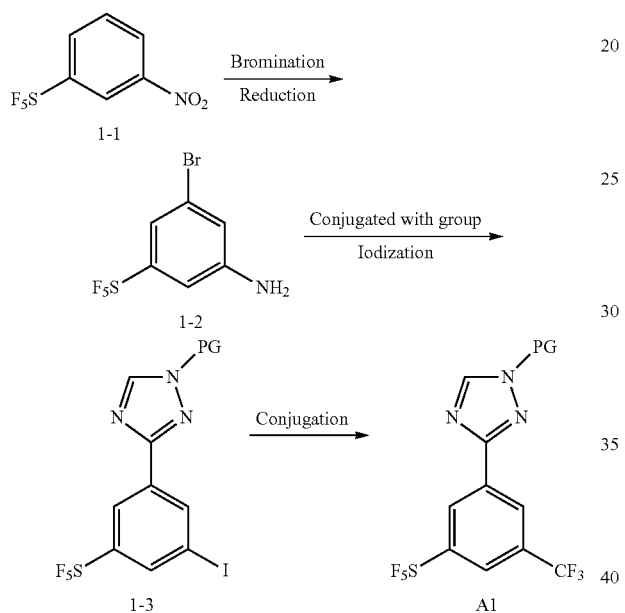

The synthesis towards structure A1 can be conducted according to the relevant procedures disclosed in references (1, *Chemistry—A European Journal*, 2012, 18, 10234-10238; 2, WO2013/19548; 3, *Bioorganic & Medicinal Chemistry*, 2008, 16, 9487-9497; 4, *Organic Letter*, 2014, 16, 4268-4271), but is not limited to these disclosed procedures. Wherein, PG is independently selected from halogen (Cl, Br, I), CN, $N_3$, $NH_2$, —COO—$C_{1-6}$ alkyl, $C_{2-6}$ alkene, $C_{2-6}$ alkene-aryl. Nitro compound 1-1 was brominated with NBS, and then reduced with ferrum to get intermediate 1-2, which was further cyanided and iodinated to get compound 1-3. Then trifluoromethyl group was added onto the aryl ring to get the important intermediate compound A1.

Scheme 2: The following reaction sequence is used to synthesize compounds of structure A2

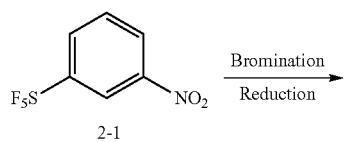

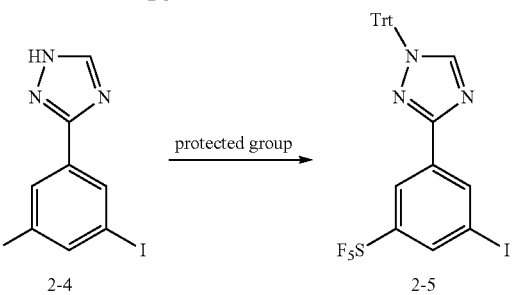

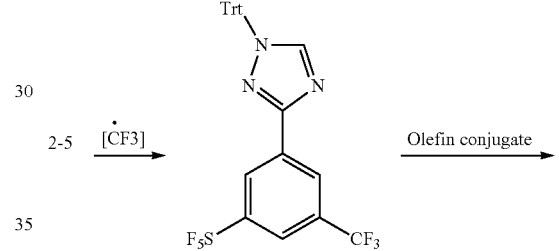

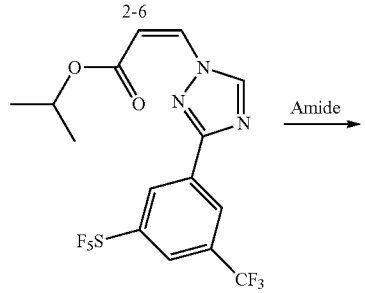

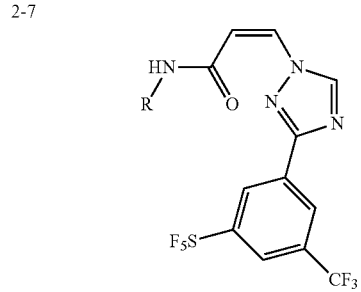

There is an alternative method to synthesize the compound A2. The synthesis towards structure A2 can be conducted according to the relevant procedures disclosed in references (1, *Chemistry—A European Journal*, 2012, 18, 10234-10238; 2, WO2013/19548; 3, *Bioorganic & Medicinal Chemistry*, 2008, 16, 9487-9497; 4, *Organic Letter*, 2014, 16, 4268-4271), but is not limited to these disclosed procedures. Nitro compound 2-1 was brominated with NBS, and then reduced with ferrum to get intermediate 2-2, which was further cyanided and iodinated get compound 2-3. Compound 3 was cyclized under acid condition to form triazole compound 2-4, triphenylmethyl chloride (TACO was used to protect the triazole amine group to form a stable compound 2-5. Copper-catalyzed trifluoromethylation method was used to the introduction of the trifluoromethyl group into compound 2-6. After that, compound 2-6 was conjugated with olefin and amine or derivatives to get the final product A2.

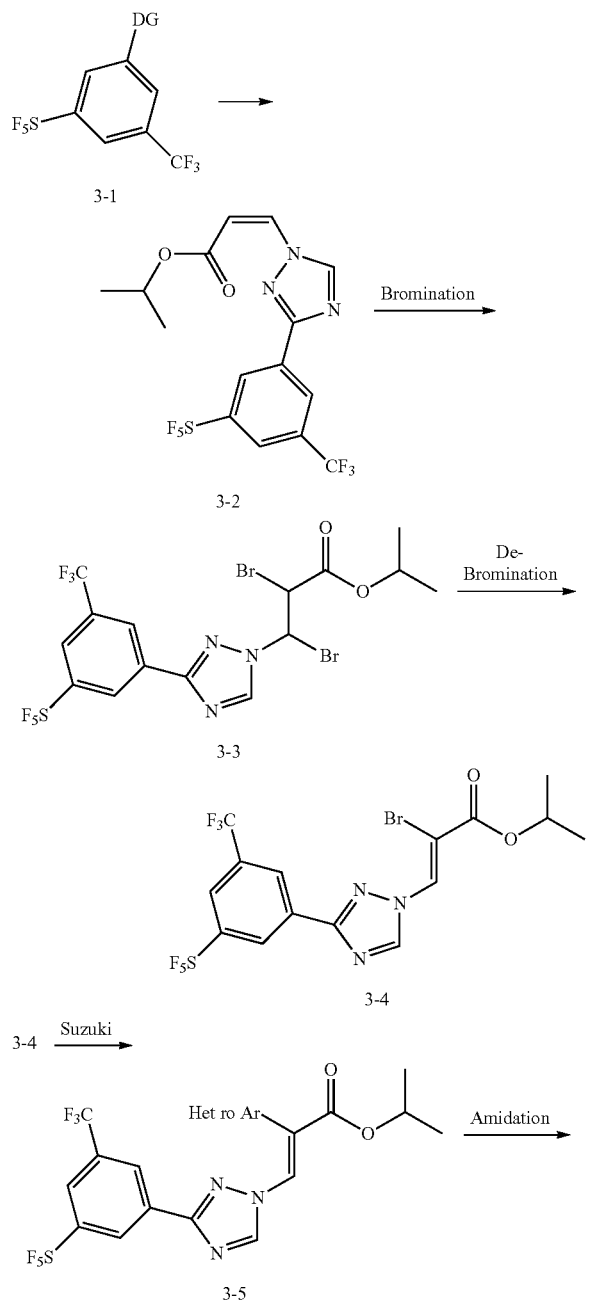

Scheme 3: The following reaction sequence is used to synthesize compounds of structure A3

The synthesis towards structure A3 can be conducted according to the relevant procedures disclosed in references (1, WO2014205393; 2, *Chemistry—A European Journal*, 2012, 18, 1914-1917; 3, *Journal of Medicinal Chemistry*, 1995, 38, 3287-3296), but is not limited to these disclosed procedures. Compound 3-1 was synthesized from scheme 1, following series of steps to get dibromide compound 3-2, and then remove one bromine to obtain olefin compound 3-3. Under Suzuki reaction condition, varies of compound can be synthesized and amidated to get the final product A3.

Preparation and Characterization of Exemplary Compounds

Compounds encompassed in the present disclosure may be prepared via different schemes. Detailed preparation processes of 10 exemplary compounds via various schemes are described below and the characterization results are listed as well.

Unless stated otherwise, all reagents were purchased from commercial suppliers without further purification. Solvent drying by standard methods was employed when necessary. The plates used for thin-layer chromatography (TLC) were E. Merck silica gel 60F254 (0.24 nm thickness) precoated on aluminum plates, and then visualized under UV light (365 nm and 254 nm) or through staining with a 5% of dodecamolybdophosphoric acid in ethanol and subsequent heating. Column chromatography was performed using silica gel (200-400 mesh) from commercial suppliers. $^1$H NMR spectra were recorded on an Agilent 400-MR NMR spectrometer (400.00 MHz for 1 H) at room temperature. Solvent signal was used as reference for $^1$H NMR (CDCl$_3$, 7.26 ppm; CD$_3$OD, 3.31 ppm; DMSO-d$_6$, 2.50 ppm; D$_2$O, 4.79 ppm). The following abbreviations were used to explain the multiplicities: s=singlet, d=doublet, t=triplet, q=quartet, br. s.=broad singlet, dd=double doublet, td=triple doublet, dt=double triplet, dq=double quartet, m=multiplet. Other abbreviations used in the experimental details are as follows: δ=chemical shift in parts per million downfield from tetramethylsilane, Ar=aryl, Ac=acyl, Boc=tert-butyloxy carbonyl, Bn=Benzyl, DCM=dichloromethane, DMF=N,N'-dimethylformamide, DIPEA=diisopropylethylamine, DMAP=4-(dimethylamino)pyridine, DMSO=dimethyl sulphoxide, EA=ethyl acetate, Et=ethyl, Me=methyl, Hz=hertz, HPLC=high performance liquid chromatography, J=coupling constant (in NMR), min=minute(s), h=hour(s), NMR=nuclear magnetic resonance, prep=preparative, t-Bu=tert-butyl, iPr=isopropyl, TBAF=tetrabutylammonium fluoride, tert=tertiary, TFA=trifluoroacetic acid, THF=tetrahydrofuran, TLC=thin-layer chromatography.

Aspects of the Invention

The invention is further defined by one or more of the following aspects.

Aspect 1. A compound having the structure of Formula (I'), Formula (II') or Formula (III'):

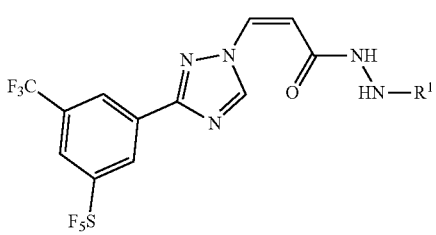
(I')

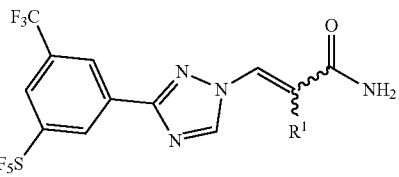
(II')

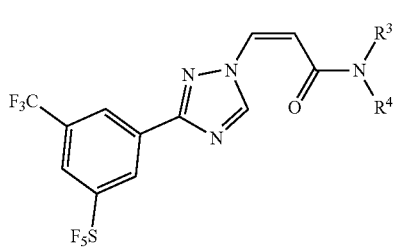
(III')

a stereoisomer, an N-oxide, a solvate, a metabolite, a pharmaceutically acceptable salt or a prodrug thereof, wherein, $R^1$ is selected from —C(=O)—$R^2$, $C_{3-6}$ heterocycloalkyl, $C_{5-10}$ heteroaryl; any heterocycloalkyl or heteroaryl of $R^1$ is optionally independently substituted with one, or more substituents selected from the group consisting of deuterium, —OH, —SH, —NO$_2$, halogen, amino, cyano, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy and $C_{1-12}$ alkylsulfanyl; and $R^2$ is selected from $C_{1-6}$ alkyl, $C_{3-6}$ cycloalkyl, $C_{3-6}$ heterocycloalkyl; any alkyl, cycloalkyl, heterocycloalkyl of $R^2$ is optionally and independently substituted with one or more substituents selected from the group consisting of halogen, amino, cyano, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy and $C_{1-12}$ alkylsulfanyl; and $R^3$, $R^4$ are independently selected from $C_{1-6}$ alkyl or $R^3$ and $R^4$ together with N which they are attached form a substituted or unsubstituted $C_{4-10}$ cycloalkylamino; any alkyl or cycloalkylamino of $R^3$ and $R^4$ is optionally and independently substituted with one or more substituents selected from the group consisting of halogen, amino, cyano, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy and $C_{1-12}$ alkylsulfanyl.

Aspect 2. The compound of aspect 1, wherein the compound has the structure of Formula (I').

Aspect 3. The compound of aspect 1, wherein the compound has the structure of Formula (II'), and the configuration of the double bond bearing $R^1$ is either E or Z.

Aspect 4. The compound of aspect 1, wherein the compound has the structure of Formula (III').

Aspect 5. The compound of aspect 1, wherein $R^1$ is —C(=O)—$R^2$.

Aspect 6. The compound of aspect 5, wherein $R^2$ is $C_{1-6}$ alkyl.

Aspect 7. The compound of aspect 5, wherein $R^2$ is $C_{3-6}$ cycloalkyl.

Aspect 8. The compound of aspect 5, wherein $R^2$ is substituted $C_{1-6}$ alkyl; and the substituent group is selected from methyl, hydroxyl, and a halogen.

Aspect 9. The compound of aspect 5, wherein $R^2$ is substituted $C_{3-6}$ cycloalkyl; and the substituent group is selected from methyl, hydroxyl, and a halogen.

Aspect 10. The compound of aspect 5, wherein $R^2$ is selected from the group consisting of methyl, ethyl, n-propyl, isopropyl, cyclopropyl, n-butyl, t-butyl, cyclobutyl, isobutyl, 4-methyl-2-pentyl, 2,2-dimethyl-1-butyl, 3,3-dimethyl-1-butyl, 2-ethyl-1-butyl, cyclopentenyl, and tetrahydrofuran,

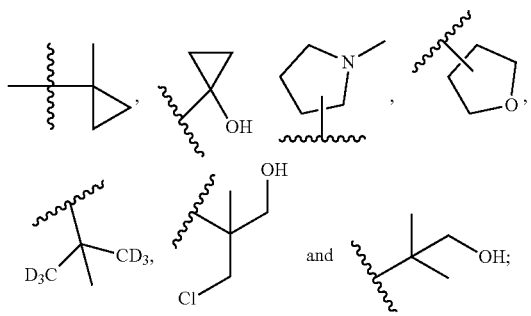

more preferably, $R^2$ is selected from the group consisting of isopropyl, cyclopropyl, cyclobutyl, 4-methyl-2-pentyl, t-butyl, 2,2-dimethyl-1-butyl, 3,3-dimethyl-1-butyl, 2-ethyl-1-butyl,

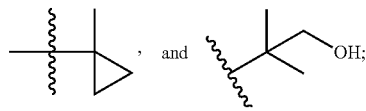

most preferably, $R^2$ is selected from the group consisting of t-butyl, 2,2-dimethyl-1-butyl,

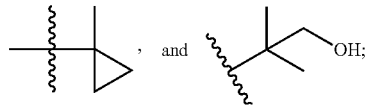

optionally, $R^2$ is selected from the group consisting of 2-methyloxiranyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, n-pentyl, isopentyl, neopentyl, 2,2-dimethylbutanyl, and

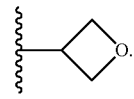

Aspect 11. The compound of aspect 2, wherein $R^1$ is $C_{3-6}$ heterocycloalkyl, of which one or two of the carbon atoms is substituted with a nitrogen atom.

Aspect 12. The compound of aspect 2, wherein $R^1$ is $C_{5-6}$ heteroaryl, of which one or two of the carbon atoms is substituted with a nitrogen, or a sulfur atom.

Aspect 13. The compound of aspect 2, wherein $R^1$ is $C_6$ heteroaryl, of which one or two of the carbon atoms is substituted with a nitrogen atom; and the one or more substituent groups is selected from —$NH_2$, —OH, halogen and —CN.

Aspect 14. The compound of aspect 2, wherein $R^1$ is selected from the group consisting of unsubstituted or substituted

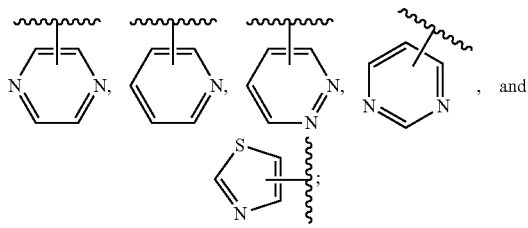

more preferably, $R^1$ is selected from the group consisting of unsubstituted or substituted

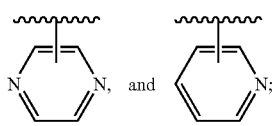

optionally, $R^1$ is selected from the group consisting of unsubstituted or substituted furyl, pyrrolyl, imdazolyl, triazolyl, tetrazolyl, oxazolyl, oxadiazolyl, 1,3,5-triazinyl, thiazolyl, and thienyl.

Aspect 15. The compound of aspect 2, wherein $R^1$ is substituted $C_{3-6}$ heterocycloalkyl, of which one or two of the carbon atoms is substituted with a nitrogen atom; and the one or more substituent groups is selected from halogen and —CN.

Aspect 16. The compound of aspect 3, wherein $R^1$ is unsubstituted or substituted $C_{5-10}$ heteroaryl, of which one or two of the carbon atoms is substituted with a nitrogen, or a sulfur atom; and the one or more substituent groups is selected from halogen and —CN.

Aspect 17. The compound of aspect 16, wherein $R^1$ is selected from the group consisting of unsubstituted or substituted

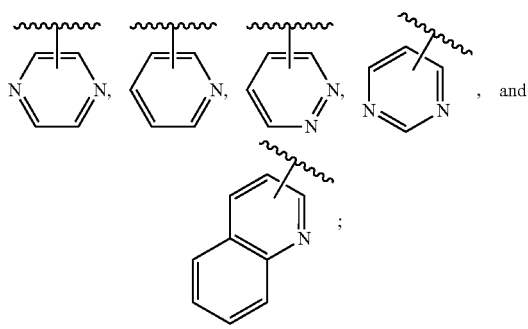

more preferably, $R^1$ is unsubstituted or substituted

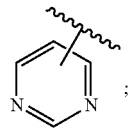

optionally, $R^1$ is selected from unsubstituted or substituted phenyl, naphthyl, furyl, benzofuryl, pyrrolyl, imdazolyl, benzimdazolyl, triazolyl, tetrazolyl, oxazolyl, oxadiazolyl, 1,3,5-triazinyl, thiazolyl, thienyl, benzothienyl, indolyl, purinyl, quinolyl, isoquinolyl and phenoxathiinyl.

Aspect 18. The compound of aspect 1, wherein the compound is a compound of Formula (I'); $R^1$ is —C(=O)—$R^2$.

Aspect 19. The compound of aspect 1, wherein the compound is a compound of Formula (I'); $R^1$ is $C_6$ heteroaryl wherein one or two carbon atoms and the associated hydrogen atom is replaced with a nitrogen atom.

Aspect 20. The compound of aspect 4, W and $R^4$ are independently $C_{1-4}$ alkyl, or $R^3$ and $R^4$ together with N which they are attached from $C_{4-10}$ cycloalkylamino ring.

Aspect 21. The compound of aspect 4, wherein $R^3$ and $R^4$ together with N which they are attached form a substituted $C_{4-10}$ cycloalkylamino; and the substituent group is selected from the group consisting of methyl, ethyl, hydroxyl, and halogen.

Aspect 22. The compound of aspect 4, wherein $R^3$ and $R^4$ are joined together to form a cycloalkylamino, wherein $C_{4-10}$ cycloalkylamino is selected from the group consisting of

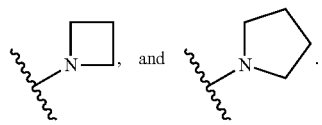 [SMILES: *N1CCC1 ; *N1CCCC1]

Aspect 23. The compound of aspect 1, wherein the compound is a compound of Formula (III'); $R^3$ and $R^4$ together with N which they are attached form a substituted cycloalkylamino, and the substituent group is selected from methyl, hydroxyl, and a halogen; and the one or more substituent groups is halogen.

Aspect 24. The compound of aspect 1, wherein the compound is selected from a compound of Formula (I'), Formula (II'), and Formula (III').

Aspect 25. A compound is selected from the group consisting of:

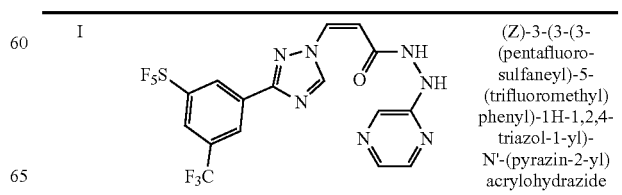

I (Z)-3-(3-(3-(pentafluorosulfaneyl)-5-(trifluoromethyl)phenyl)-1H-1,2,4-triazol-1-yl)-N'-(pyrazin-2-yl)acrylohydrazide

| | | |
|---|---|---|
| II | | (Z)-3-(3-(3-(pentafluoro-sulfaneyl)-5-(trifluoromethyl)phenyl)-1H-1,2,4-triazol-1-yl)-N'-(pyridin-2-yl)acrylohydrazide |
| III | | (Z)-3-(3-(3-(pentafluoro-sulfaneyl)-5-(trifluoromethyl)phenyl)-1H-1,2,4-triazol-1-yl)-N'-pivaloyl-acrylohydrazide |
| IV | | (E)-3-(3-(3-(pentafluoro-sulfaneyl)-5-(trifluoromethyl)phenyl)-1H-1,2,4-triazol-1-yl)-2-(pyrimidin-5-yl)acrylamide |
| V | | (Z)-3-(3-(3-(pentafluoro-sulfaneyl)-5-(trifluoromethyl)phenyl)-1H-1,2,4-triazol-1-yl)-2-(pyrimidin-5-yl)acrylamide |
| VI | | (Z)-3-(3-(3-(pentafluoro-sulfaneyl)-5-(trifluoromethyl)phenyl)-1H-1,2,4-triazol-1-yl)-N'-(thiazol-2-yl)acrylohydrazide |
| VII | | (Z)-N'-(3-(3-(3-(pentafluoro-sulfaneyl)-5-(trifluoromethyl)phenyl)-1H-1,2,4-triazol-1-yl)acryloyl)cyclopropane-carbohydrazide |
| VIII | | (Z)-N'-isobutyryl-3-(3-(3-(pentafluoro-sulfaneyl)-5-(trifluoromethyl)phenyl)-1H-1,2,4-triazol-1-yl)acrylohydrazide |
| IX | | (Z)-N'-(3-(3-(3-(pentafluoro-sulfaneyl)-5-(trifluoromethyl)phenyl)-1H-1,2,4-triazol-1-yl)acryloyl)butyrohydrazide |
| X | | (Z)-N'-(3-(3-(3-(pentafluoro-sulfaneyl)-5-(trifluoromethyl)phenyl)-1H-1,2,4-triazol-1-yl)acryloyl)cyclobutane-carbohydrazide |
| XI | | (Z)-1-methyl-N'-(3-(3-(3-(pentafluoro-sulfaneyl)-5-(trifluoromethyl)phenyl)-1H-1,2,4-triazol-1-yl)acryloyl)cyclopropane-1-carbohydrazide |
| XII | | (Z)-N'-(3-chloro-2-(hydroxymethyl)-2-methylpropanoyl)-3-(3-(3-(pentafluoro-sulfaneyl)-5-(trifluoromethyl)phenyl)-1H-1,2,4-triazol-1-yl)acrylohydrazide |
| XIII | | (Z)-3-methyl-N'-(3-(3-(3-(pentafluoro-sulfaneyl)-5-(trifluoromethyl)phenyl)-1H-1,2,4-triazol-1-yl)acryloyl)butanehydrazide |
| XIV | | (Z)-N'-acetyl-3-(3-(3-(pentafluoro-sulfaneyl)-5-(trifluoromethyl)phenyl)-1H-1,2,4-triazol-1-yl)acrylohydrazide |
| XV | | (Z)-3-(3-(3-(pentafluoro-sulfaneyl)-5-(trifluoromethyl)phenyl)-1H-1,2,4-triazol-1-yl)-N'-propionyl-acrylohydrazide |
| XVI | | (Z)-N'-(3-(3-(3-(pentafluoro-sulfaneyl)-5-(trifluoromethyl)phenyl)-1H-1,2,4-triazol-1-yl)acryloyl)cyclopentane-carbohydrazide |
| XVII | | (Z)-N'-(2-methyl-2-(methyl-d3)propanoyl-3,3,3-d3)-3-(3-(3-(pentafluoro-sulfaneyl)-5-(trifluoromethyl)phenyl)-1H-1,2,4-triazol-1-yl)acrylohydrazide |

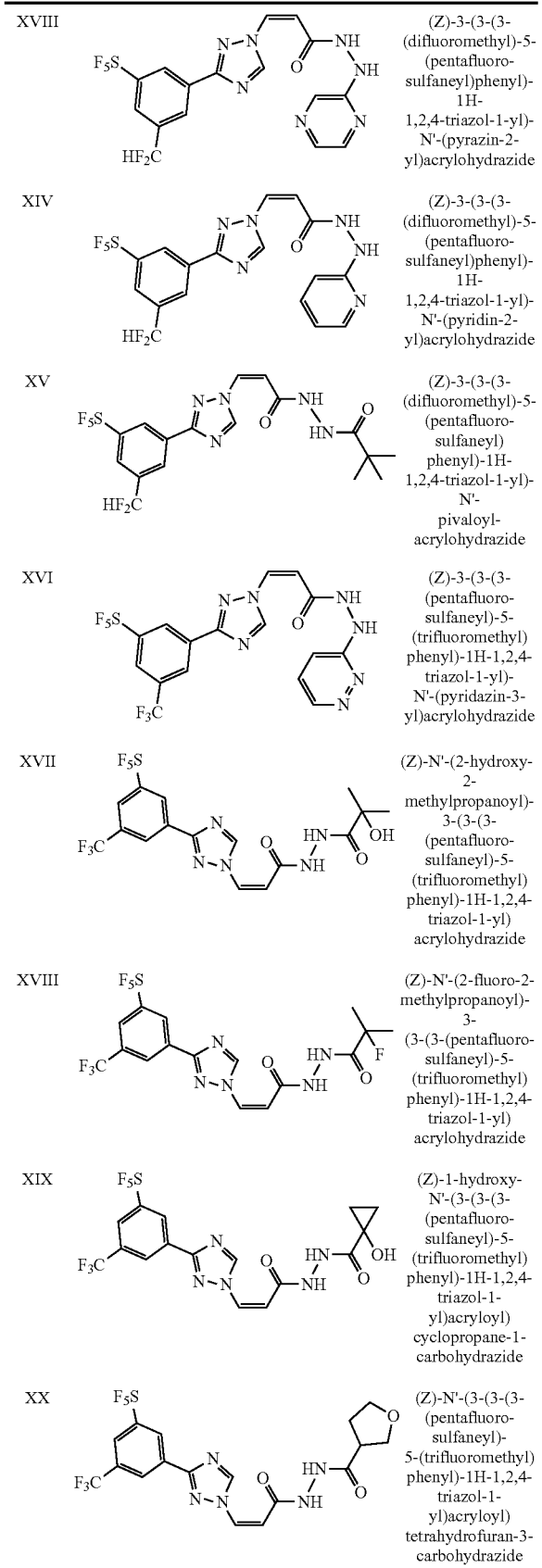
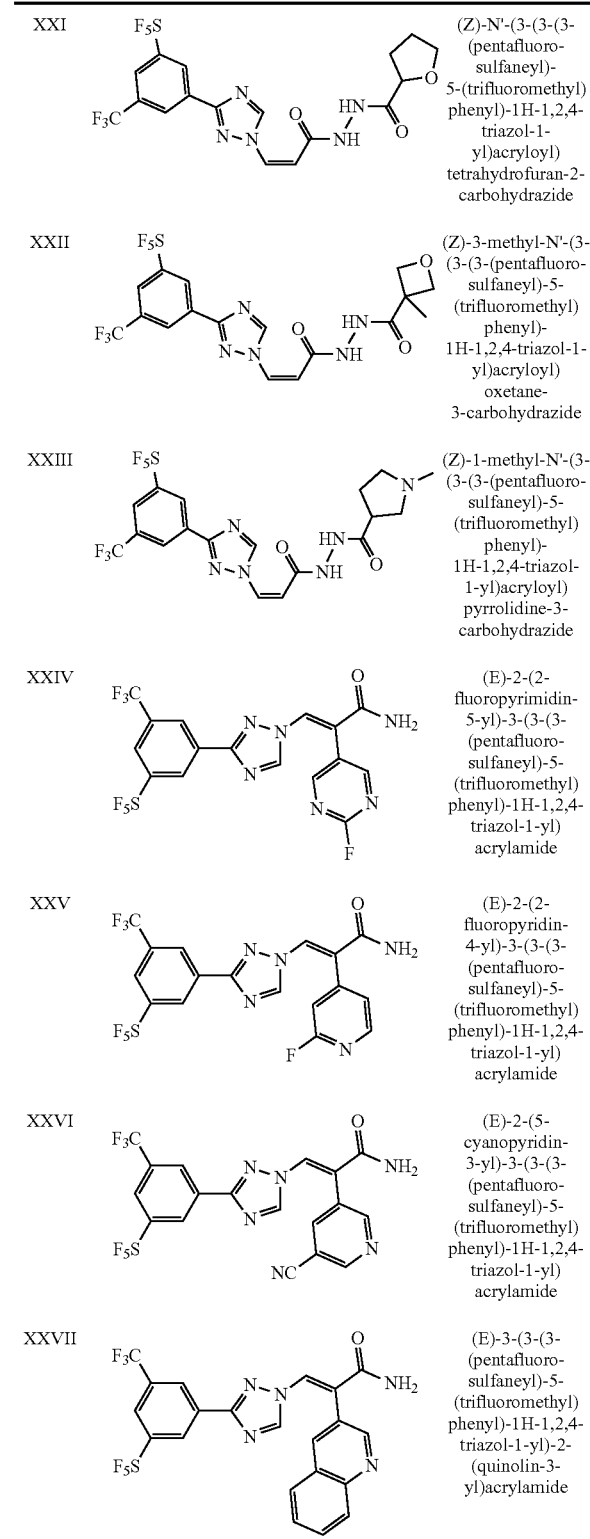

| | |
|---|---|
| XVIII | (Z)-3-(3-(3-(difluoromethyl)-5-(pentafluoro-sulfaneyl)phenyl)-1H-1,2,4-triazol-1-yl)-N'-(pyrazin-2-yl)acrylohydrazide |
| XIV | (Z)-3-(3-(3-(difluoromethyl)-5-(pentafluoro-sulfaneyl)phenyl)-1H-1,2,4-triazol-1-yl)-N'-(pyridin-2-yl)acrylohydrazide |
| XV | (Z)-3-(3-(3-(difluoromethyl)-5-(pentafluoro-sulfaneyl)phenyl)-1H-1,2,4-triazol-1-yl)-N'-pivaloyl-acrylohydrazide |
| XVI | (Z)-3-(3-(3-(pentafluoro-sulfaneyl)-5-(trifluoromethyl)phenyl)-1H-1,2,4-triazol-1-yl)-N'-(pyridazin-3-yl)acrylohydrazide |
| XVII | (Z)-N'-(2-hydroxy-2-methylpropanoyl)-3-(3-(3-(pentafluoro-sulfaneyl)-5-(trifluoromethyl)phenyl)-1H-1,2,4-triazol-1-yl)acrylohydrazide |
| XVIII | (Z)-N'-(2-fluoro-2-methylpropanoyl)-3-(3-(3-(pentafluoro-sulfaneyl)-5-(trifluoromethyl)phenyl)-1H-1,2,4-triazol-1-yl)acrylohydrazide |
| XIX | (Z)-1-hydroxy-N'-(3-(3-(3-(pentafluoro-sulfaneyl)-5-(trifluoromethyl)phenyl)-1H-1,2,4-triazol-1-yl)acryloyl)cyclopropane-1-carbohydrazide |
| XX | (Z)-N'-(3-(3-(3-(pentafluoro-sulfaneyl)-5-(trifluoromethyl)phenyl)-1H-1,2,4-triazol-1-yl)acryloyl)tetrahydrofuran-3-carbohydrazide |
| XXI | (Z)-N'-(3-(3-(3-(pentafluoro-sulfaneyl)-5-(trifluoromethyl)phenyl)-1H-1,2,4-triazol-1-yl)acryloyl)tetrahydrofuran-2-carbohydrazide |
| XXII | (Z)-3-methyl-N'-(3-(3-(3-(pentafluoro-sulfaneyl)-5-(trifluoromethyl)phenyl)-1H-1,2,4-triazol-1-yl)acryloyl)oxetane-3-carbohydrazide |
| XXIII | (Z)-1-methyl-N'-(3-(3-(3-(pentafluoro-sulfaneyl)-5-(trifluoromethyl)phenyl)-1H-1,2,4-triazol-1-yl)acryloyl)pyrrolidine-3-carbohydrazide |
| XXIV | (E)-2-(2-fluoropyrimidin-5-yl)-3-(3-(3-(pentafluoro-sulfaneyl)-5-(trifluoromethyl)phenyl)-1H-1,2,4-triazol-1-yl)acrylamide |
| XXV | (E)-2-(2-fluoropyridin-4-yl)-3-(3-(3-(pentafluoro-sulfaneyl)-5-(trifluoromethyl)phenyl)-1H-1,2,4-triazol-1-yl)acrylamide |
| XXVI | (E)-2-(5-cyanopyridin-3-yl)-3-(3-(3-(pentafluoro-sulfaneyl)-5-(trifluoromethyl)phenyl)-1H-1,2,4-triazol-1-yl)acrylamide |
| XXVII | (E)-3-(3-(3-(pentafluoro-sulfaneyl)-5-(trifluoromethyl)phenyl)-1H-1,2,4-triazol-1-yl)-2-(quinolin-3-yl)acrylamide | a stereoisomer, an N-oxide, a solvate, a metabolite, a pharmaceutically acceptable salt or a prodrug thereof.

Aspect 26. A pharmaceutical composition comprising a therapeutically effective amount of at least one compound according to any one of the proceeding aspects 1 to 25.

Aspect 27. The pharmaceutical composition of aspect 26, further comprising a pharmaceutically acceptable excipient, carrier, adjuvant, solvent, support or a combination any of the foregoing.

Aspect 28. The pharmaceutical composition of aspect 26, further comprising adjunctive therapies or therapeutically effective amounts of one or more other adjunctive active ingredients or a combination any of the foregoing, wherein the other adjunctive active ingredients are used for treating a neurological disorder or a neurological disease or a cancer.

Aspect 29. The pharmaceutical composition of aspect 28, wherein the therapeutically effective amount of at least one compound is for treating a disorder or disease associated with XPO1/CRM1 activity, comprising a neurological disorder or a neurological disease or a cancer.

Aspect 30. The pharmaceutical composition of aspect 28, wherein the therapeutically effective amount of at least one compound is for treating a cancer, and the adjunctive therapies comprise radiation, while the adjunctive active ingredients comprise a chemotherapeutic agent, a TK or RTK inhibitor, a BCL2 inhibitor, a FLT3 inhibitor, a EGFR inhibitor, a pro-apoptotic drug, an antibody-drug conjugate (ADC), an immune checkpoint inhibitor, CAR-T, a personalized cancer vaccine, and a chemokine/cytokine.

Aspect 31. The pharmaceutical composition of aspect 26, wherein the therapeutically effective amount of at least one compound is for treating a neurological disorder or a neurological disease.

Aspect 32. Use of the compound according to any one of aspects 1 to 25 or the pharmaceutical composition according to any one of aspects 26 to 31 in the manufacture of a medicament for treating or lessening a disorder or disease in a patient by modulating XPO1/CRM1 activity in said patient.

Aspect 33. The use of the compound or pharmaceutical composition according to aspect 32, wherein the disorder or disease is a neurological disorder or a neurological disease or a cancer.

Aspect 34. The compound according to any one of aspects 1 to 25 or the pharmaceutical composition according to any one of aspects 26 to 31 for use in treating or lessening a disorder or disease in a human patient by modulating XPO1/CRM1 activity in said patient.

Aspect 35. The compound or pharmaceutical composition for use according to aspect 34, wherein the disorder or disease is a neurological disorder or a neurological disease or a cancer.

Aspect 36. The compound or pharmaceutical composition for use according to aspect 34, wherein the disorder or disease is a neurological disorder or disease.

Aspect 37. The compound or pharmaceutical composition for use according to aspect 36, wherein the neurological disorder or disease is amyotrophic lateral sclerosis, epilepsy, traumatic brain injuries, Huntington's disease, Parkinson's disease, rheumatoid arthritis, systemic lupus erythematosus.

Aspect 38. The compound or pharmaceutical composition for use according to aspect 34, wherein the disorder or disease is a cancer.

Aspect 39. The compound or pharmaceutical composition for use according to aspect 38, wherein the cancer is lymphoma, liposarcoma, multiple myeloma, myelodysplastic syndrome, prostate cancer, colorectal cancer, endometrial cancer, pancreatic cancer, gastric cancer, diffuse large b-cell lymphoma, non-small cell lung cancer, ovarian carcinoma, breast cancer, acute myeloid leukemia, thymoma, esophageal cancer, glioblastoma, and other solid tumors.

Aspect 40. A method for treating or lessening a disorder or disease in a patient by modulating XPO1/CRM1 activity in said patient comprising administering to the patient a therapeutically effective amount of a compound according to any one of aspects 1 to 25 or a pharmaceutical composition according to any one of aspects 26 to 31.

Aspect 41. The method of aspect 40, wherein the disorder or disease is a neurological disorder or disease.

Aspect 42. The method of aspect 41, wherein the neurological disorder or disease is amyotrophic lateral sclerosis, epilepsy, traumatic brain injuries, Huntington's disease, Parkinson's disease, rheumatoid arthritis, systemic lupus erythematosus.

Aspect 43. The method of aspect 40, wherein the disorder or disease is a cancer.

Aspect 44. The method of aspect 43, wherein the cancer is lymphoma, liposarcoma, multiple myeloma, myelodysplastic syndrome, prostate cancer, colorectal cancer, endometrial cancer, pancreatic cancer, gastric cancer, diffuse large b-cell lymphoma, non-small cell lung cancer, ovarian carcinoma, breast cancer, acute myeloid leukemia, thymoma, esophageal cancer, glioblastoma, and other solid tumors.

EXAMPLES

It should be noted that embodiments of the present invention described in detail below are exemplary for explaining the present invention only, and not be construed as limiting the present invention. Examples without a specific technology or condition can be implemented according to technology or condition in the documentation of the art or according to the product instructions. The reagents or instruments without manufacturers are available through conventional purchase. Those having skill in the art will recognize that the starting materials may be various and additional steps employed to produce compounds encompassed by the present inventions, as demonstrated by the following examples.

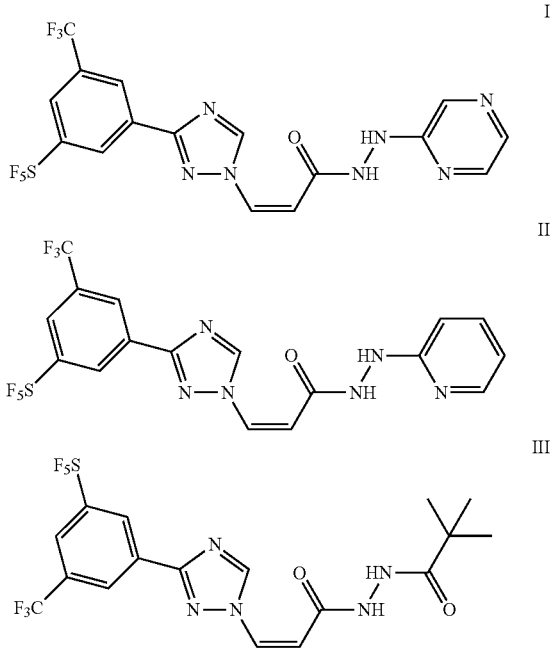

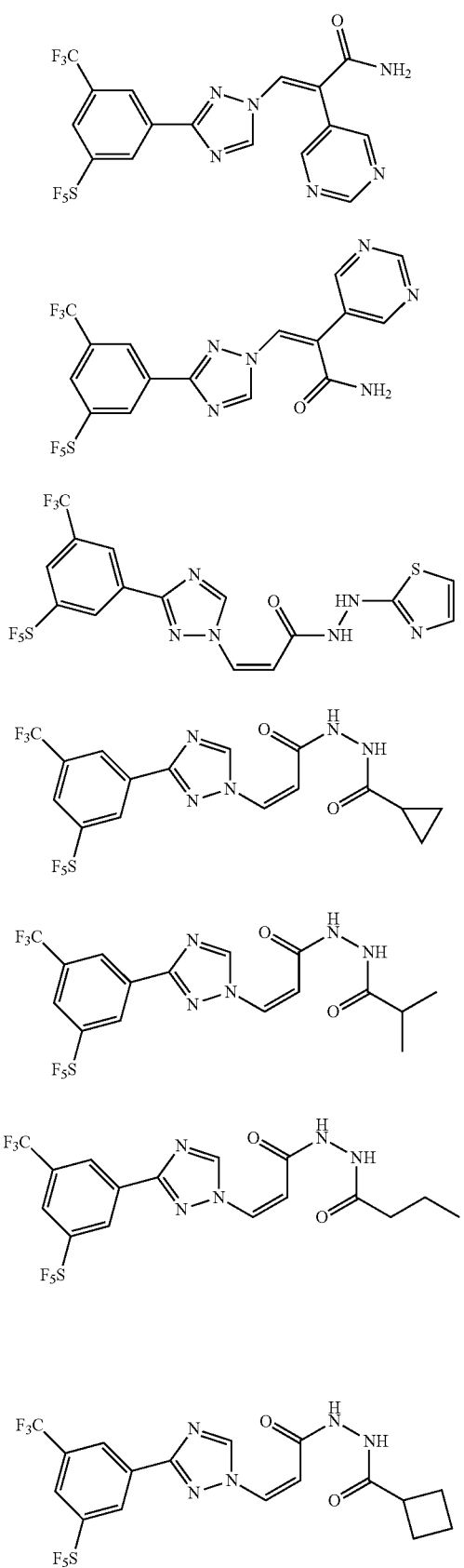
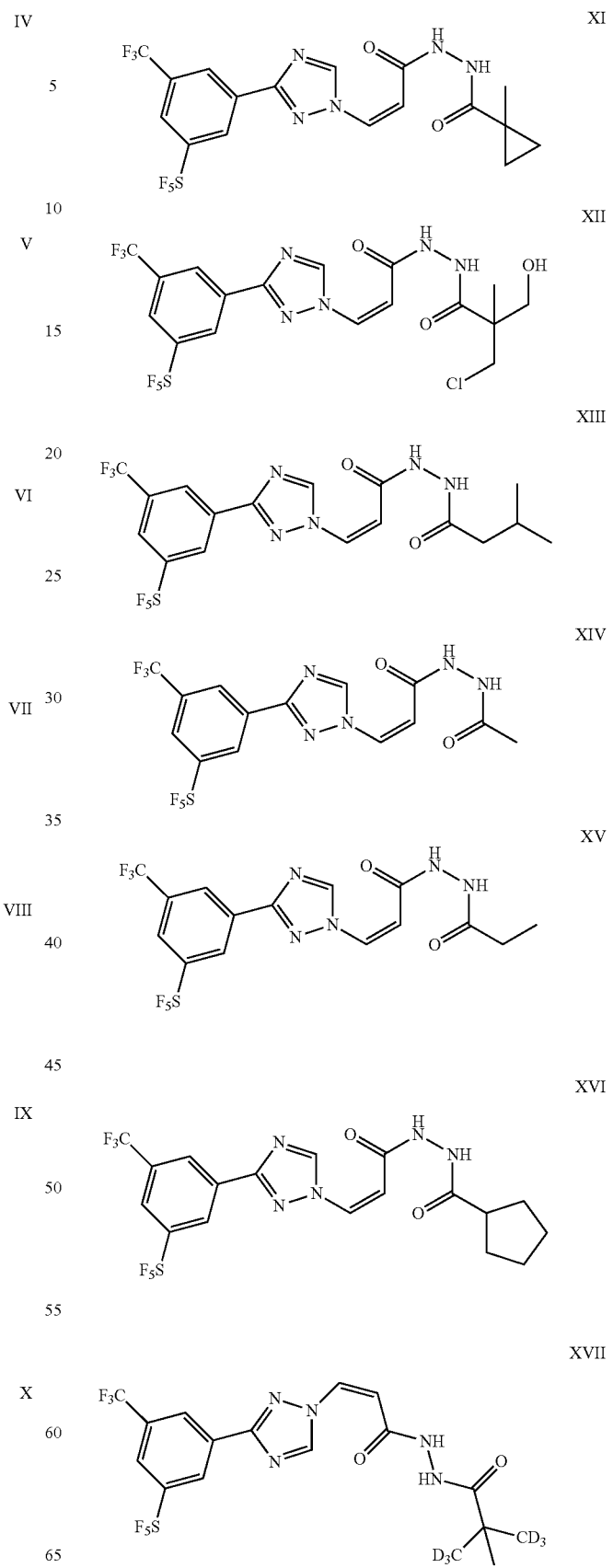

Example 1

(Z)-3-(3-(3-(Pentafluorosulfanyl)-5-(trifluoromethyl)phenyl)-1H-1,2,4-triazol-1-yl)-N'-(pyrazin-2-yl)acrylohydrazide (I)

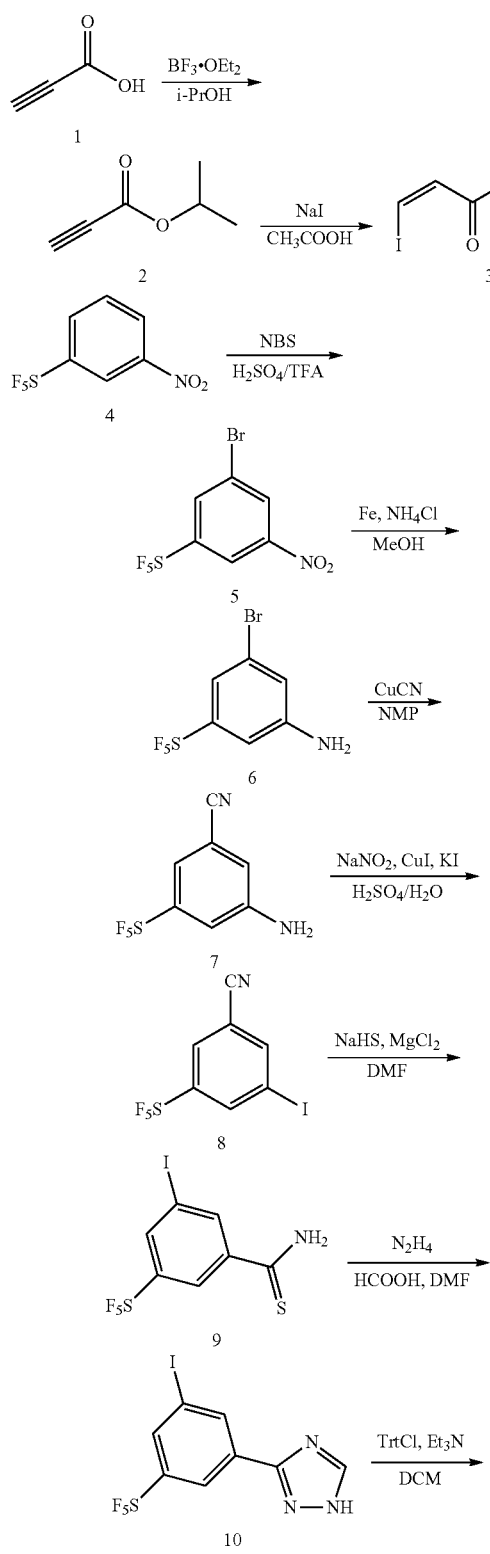

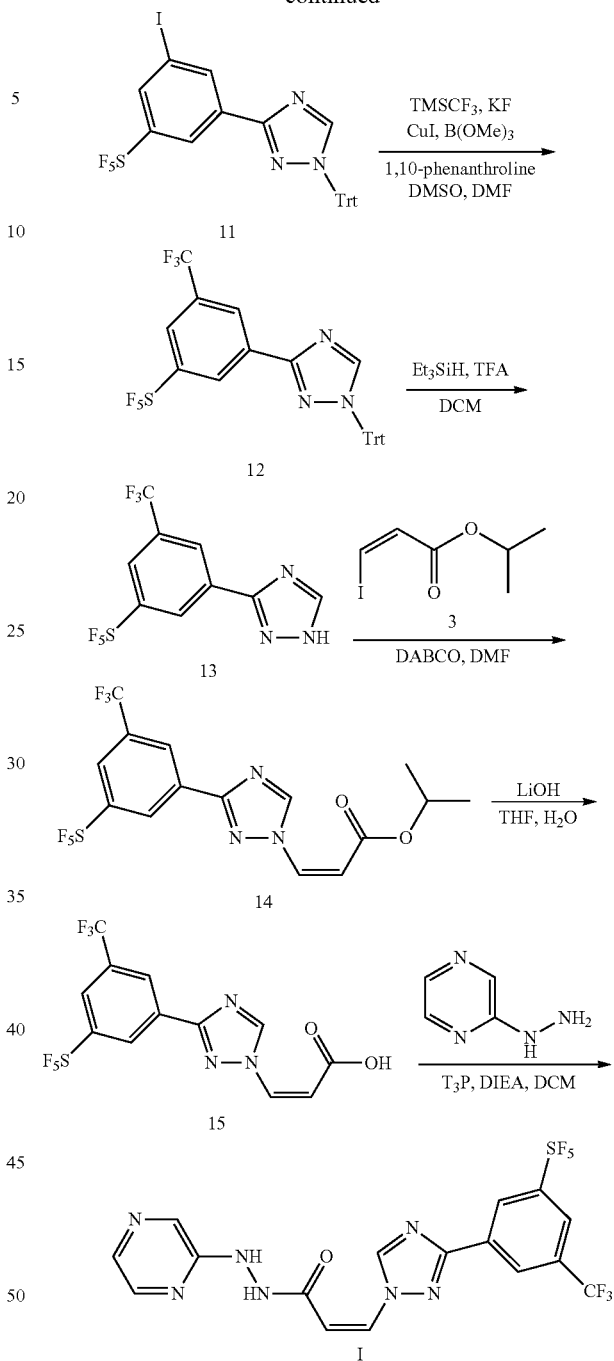

Step 1: Synthesis of Isopropyl Propiolate (2)

To a mixture of propiolic acid 1 (30 g, 0.43 moles) in isopropanol (100 mL) was added $BF_3$ etherate (122.1 g, 0.86 moles) at 25° C. After stirring for 10 minutes, the reaction mixture was heated to 90° C. and stirred for 2 h. The completion of the reaction was monitored by TLC. The reaction mixture was brought down to 25 to 30° C. and quenched with crushed ice followed by extracted with dichloromethane (2×150 mL). The organic layer was washed with water and then with brine solution. Organic layer was dried over Na$_2$SO$_4$ and concentrated under vacuum to give the isopropyl propiolate 2 (35.2 g, 73% yield).

Step 2: Synthesis of Isopropyl (Z)-3-Iodoacrylate (3)

Isopropyl propiolate 2 (35.2 g, 0.31 mmol) was added in acetic acid (200 mL) at 25° C., and the reaction mixture was stirred for 10 minutes. Sodium iodide (70.0 g, 0.47 mmol) was added (a dark brown color was observed) while stirring. The temperature was increased to 110° C. and the reaction was maintained at that temperature for 2 h. The completion of the reaction was monitored by TLC. The reaction mixture was cooled to room temperature, quenched with ice cold water (200 mL) and stirred for 30 minutes. Methyl tert-butyl ether (MTBE) (200 mL) was added to the reaction mixture and stirred for another 30 minutes. The organic layer was separated, and the aqueous layer was re-extracted with MTBE (200 mL). The combined organic layers were washed with NaHCO$_3$ (2×100 mL), NaHSO$_3$ (2×100 mL) and brine (100 mL), dried over Na$_2$SO$_4$ and concentrated under vacuum at 35° C. to afford (Z)-isopropyl 3-iodoacrylate 3 (48.5 g, 61% yield) as a light-yellow oil. $^1$H NMR (400 MHz, CDCl$_3$) δ 7.38 (d, J=8.0 Hz, 1H), 6.83 (d, J=8.0 Hz, 1H), 5.07-5.13 (m, 1H), 1.27 (d, J=8.0 Hz, 6H).

Step 3: Synthesis of (3-bromo-5-nitrophenyl)pentafluorosulfane (5)

To a 250 mL round-bottom flask was added compound 4 (9.25 g, 37.1 mmol), TFA (20 mL) and conc. H$_2$SO$_4$ (100 mL), then the mixture was stirred vigorously and NBS (9.92 g, 55.7 mmol) was added in portions over 30 min and the reaction was stirred at 25° C. for 12 h. The mixture was poured into ice water, extracted with EA (3×100 mL). The combined organic layer was washed with saturated NaHCO$_3$ (3×100 mL) and water (3×100 mL), dried Na$_2$SO$_4$ and concentrated under vacuum. The crude product was purified on silica gel column eluting with PE:EA=25:1 to obtain the titled compound 5 (12.04 g, 99% yield) as a light-yellow oil. $^1$H NMR (400 MHz, CDCl$_3$) δ 8.57 (s, 1H), 8.55 (s, 1H), 8.22 (s, 1H).

Step 4: Synthesis of 3-bromo-5-(pentafluorosulfanyl)aniline (6)

To a solution of compound 5 (5.9 g, 18.0 mmol) in MeOH (40 mL) and water (10 mL) was added and Fe (5.0 g, 90 mmol) and NH$_4$C$_1$ (4.8 g, 90 mmol) at 25° C. The mixture was stirred at 90° C. for 2 h, and then filtered, washed with MeOH (20 mL) and removed the solvent. To the residue was added EA (100 mL) and washed with water (3×50 mL). The organic phase was dried over Na$_2$SO$_4$ and concentrated under vacuum. The crude product was purified on silica gel column eluting with PE:EA=10:1 to obtain the titled compound 6 (5.1 g, 96% yield) as a light-yellow oil. $^1$H NMR (400 MHz, CDCl$_3$) δ 7.35 (s, 1 H), 7.20 (s, 1H), 6.99 (s, 1H).

Step 5: Synthesis of 3-amino-5-(pentafluorosulfanyl)benzonitrile (7)

To a 250 mL round-bottom flask was added compound 6 (8.68 g, 29.2 mmol) and NMP (100 mL), then CuCN (5.26 g, 58.5 mmol) was added and the reaction was stirred at 180° C. under N$_2$ atmosphere for 6 h. The mixture was cooled to 25° C. and filtered. To the filtrate was added EA (200 mL) and washed with water (3×200 mL). The organic layer was dried over Na$_2$SO$_4$ and concentrated under vacuum. The crude product was purified on silica gel column with eluting solvent PE:EA=10:1 to obtain the titled compound 7 (3.3 g, 46% yield) as a light yellow solid.

Step 6: Synthesis of 3-iodo-5-(pentafluorosulfanyl)benzonitrile (8)

Compound 7 (4.23 g, 17.3 mmol) was suspended in a mixture of conc. H$_2$SO$_4$ (8.7 mL) and water (17.3 mL) and cooled to 0° C. A solution of NaNO$_2$ (1.23 g, 17.9 mmol) in H$_2$O (3.5 mL) was added over 1 h and the resulting mixture was stirred further for 1 h at 0° C. Then CuI (173 mg, 0.87 mmol), KI (3.05 g, 18 mmol) in H$_2$O (3.5 mL) was added dropwise over 1 h, then the mixture was stirred at 25° C. for 10 h. To the mixture was added EA (100 mL) and washed with H$_2$O (3×50 mL). The organic layer was dried over Na$_2$SO$_4$ and concentrated under vacuum. The crude product was purified on silica gel column with eluting solvent PE:EA=5:1 to obtain the titled compound 8 (3.65 g, 59% yield) as a light yellow solid. $^1$H NMR (400 MHz, CDCl$_3$) δ 8.28 (s, 1H), 8.13 (s, 1H), 8.01 (s, 1H).

Step 7: Synthesis of 3-iodo-5-(pentafluorosulfanyl)benzothioamide (9)

To a solution of compound 8 (3.6 g, 10 mmol) in DMF (50 mL) was added NaHS (1.1 g, 20 mmol) and MgCl$_2$·6H$_2$O (2 g, 10 mmol), the mixture was stirred at 25° C. for 2 h. To the mixture was added EA (100 mL) and washed with H$_2$O (3×50 mL). The organic layer was dried over Na$_2$SO$_4$ and concentrated under vacuum to obtain a crude product 9 (3.8 g, 98% yield) which was used for next step without any purification. MS (ESI): [M+H$^+$]=389.9.

Step 8: Synthesis of 3-(3-iodo-5-(pentafluorosulfanyl)phenyl)-1H-1, 2, 4-triazole (10)

To a solution of compound 9 (3.32 g, 8.53 mmol) in DMF (15 mL) was added N$_2$H$_4$·H$_2$O (853 mg, 17.1 mmol), the mixture was stirred at 25° C. for 3 h. Then formic acid (10 mL) was added and the mixture was stirred at 90° C. for 3 h. The reaction was cooled to 25° C. and quenched with saturated NaHCO$_3$ (50 mL), extracted with EA (50 mL). The organic layer was washed with brine (50 mL), dried over Na$_2$SO$_4$ and concentrated under vacuum to obtain a crude product 10 (3.36 g, 99% yield) which was used for next step without further purification. nMS (ESI): [M+H$^+$]=397.9.

Step 9: Synthesis of 3-(3-iodo-5-(pentafluorosulfanyl)phenyl)-1-trityl-1H-1,2,4-triazole (11)

To a solution of compound 10 (3.37 g, 8.53 mmol) in DCM (50 mL) was added Et$_3$N (1.29 g, 12.8 mmol) and TrtCl (3.57 g, 12.8 mmol), the mixture was stirred at 25° C. for 2 h then washed with water (3×50 mL). The organic layer was dried and concentrated under vacuum. The crude product was purified on silica gel column with eluting solvent DCM:MeOH=50:1 to obtain the titled compound 11 (5.36 g, 98% yield) as a light yellow solid. $^1$H NMR (400 MHz, CDCl$_3$) δ 8.57 (s, 1H), 8.46 (s, 1H), 8.05 (s, 1H), 8.01 (s, 1H), 7.37-7.15 (m, 15H).

Step 10: Synthesis of 3-(3-(pentafluorosulfanyl)-5-(trifluoromethyl)phenyl)-1-trityl-1H-1, 2, 4-triazole (12)

To a 100 mL three-neck flask was charged with compound 11 (5.36 g, 8.4 mmol), KF (1.46 g, 25.2 mmol), CuI (320 mg, 1.7 mmol), 1,10-phenanthroline (306 mg, 1.7 mmol), then the crude material in flask was vacuum for three times under N₂ atmosphere. Then a mixture solution of DMSO (20 mL) and DMF (10 mL), TMSCF₃ (4.76 g, 33.6 mmol) and B(OMe)₃ (2.55 g, 25.2 mmol) was added to above reaction solution, then the reaction was stirred at 70° C. under N₂ atmosphere for 24 h. The mixture was cooled to 25° C. and filtered. To the filtrate was added EA (100 mL) and washed with H₂O (3×50 mL) and brine (3×50 mL). The organic layer was dried over Na₂SO₄ and concentrated under vacuum to obtain the titled compound 12 (4.88 g, 99% yield) as a black solid which was used for next step without any purification. ¹⁹F NMR (400 MHz, CDCl₃) δ 62.45 ppm, −62.79 ppm.

Step 11: Synthesis of 3-(3-(pentafluorosulfanyl)-5-(trifluoromethyl)phenyl)-1H-1,2,4-triazole (13)

To a solution of compound 12 (4.88 g, 8.4 mmol) in DCM (50 mL) was added TFA (1.67 g, 14.3 mmol) and Et₃SiH (1.95 g, 16.8 mmol), the mixture was stirred at 25° C. for 1 h then concentrated under vacuum to remove the organic solution. To the residue was added EA (100 mL) and washed with H₂O (3×50 mL). The organic layer was dried over Na₂SO₄ and concentrated under vacuum. The crude product was purified on silica gel column eluting with PE:EA=1:1 to obtain the titled compound 13 (2.1 g, 74% yield) as a light yellow solid. MS (ESI): [M+H⁺]=340.1.

Step 12: Synthesis of isopropyl (Z)-3-(3-(3-(pentafluorosulfanyl)-5-(trifluoromethyl)phenyl)-1H-1,2,4-triazol-1-yl)acrylate (14)

To a solution of compound 13 (2.1 g, 6.2 mmol) in DMF (15 mL) was added DABCO (1.39 g, 12.4 mmol) and compound 3 (2.08 g, 8.7 mmol), the mixture was stirred at 25° C. for 3 h then quenched with saturated NH₄Cl (50 mL), extracted with EA (100 mL). The organic layer was washed with brine (3×50 mL), dried over Na₂SO₄, filtered and concentrated under vacuum. The crude product was purified on silica gel column eluting with PE:EA=30:1 to obtain the titled compound 14 (2.09 g, 75% yield) as a white solid. MS (ESI): [M+H⁺]=452.1. ¹H NMR (400 MHz, CDCl₃) δ 8.64 (s, 1H), 8.51 (s, 1H), 8.34 (s, 1H), 8.11 (s, 1H), 7.96 (d, J=14.1 Hz, 1H), 7.69 (d, J=13.7 Hz, 1H), 5.15 (m, 1H), 1.32 (d, J=6.3 Hz, 6H).

Step 13: Synthesis of (Z)-3-(3-(3-(pentafluorosulfanyl)-5-(trifluoromethyl)phenyl)-1H-1,2,4-triazol-1-yl)acrylic acid (15)

To a solution of compound 14 (2.09 g, 4.63 mmol) in THF (20 mL) was added LiOH H₂O (3.34 g, 55.6 mmol, 1N in 56 mL H₂O), the mixture was stirred at 25° C. for 3 h and then acidified with 1 N HCl to pH=3, extracted with EA (3×100 mL). The organic layer was washed with saturated NaHCO₃ (50 mL), dried over Na₂SO₄ and concentrated under vacuum to obtain the titled compound 15 (1.89 g, 99% yield) as a white solid. MS (ESI): [M+H⁺]=410.0.

Step 14: Synthesis of (Z)-3-(3-(3-(pentafluorosulfanyl)-5-(trifluoromethyl)phenyl)-1H-1,2,4-triazol-1-yl)-N'-(pyrazin-2-yl)acrylohydrazide (I)

To a solution of compound 15 (1.01 g, 2.5 mmol), 16 (826 mg, 7.5 mmol), DIEA (1.29 g, 10 mmol) in EA/DCM (10 mL/10 mL, v/v) was added T₃P (6.36 g, 10 mmol, 50% in EA). The mixture was stirred at −40° C. for 3 h, then the organic solution was concentrated under vacuum. To the residue was added EA (100 ml) and washed with H₂O (3×50 mL). The organic phase was concentrated and purified by prep-TLC (DCM:MeOH:NH₃·H₂O=15:1:0.1) to obtain the titled compound I (594 mg, 48% yield) as a yellow solid. MS (ESI): [M+H⁺]=502.1. ¹H NMR (400 MHz, DMSO-d₆) δ 10.51 (s, 1H), 9.56 (s, 1H), 9.11 (s, 1H), 8.61 (s, 1H), 8.48 (s, 1H), 8.39 (s, 1H), 8.07 (s, 2H), 7.90 (s, 1H), 7.50 (d, J=10 Hz, 1H), 6.06 (d, J=10.4 Hz, 1H).

Example 2

(Z)-3-(3-(3-(Pentafluorosulfanyl)-5-(trifluoromethyl)phenyl)-1H-1,2,4-triazol-1-yl)-N'-(pyridin-2-yl)acrylohydrazide (II)

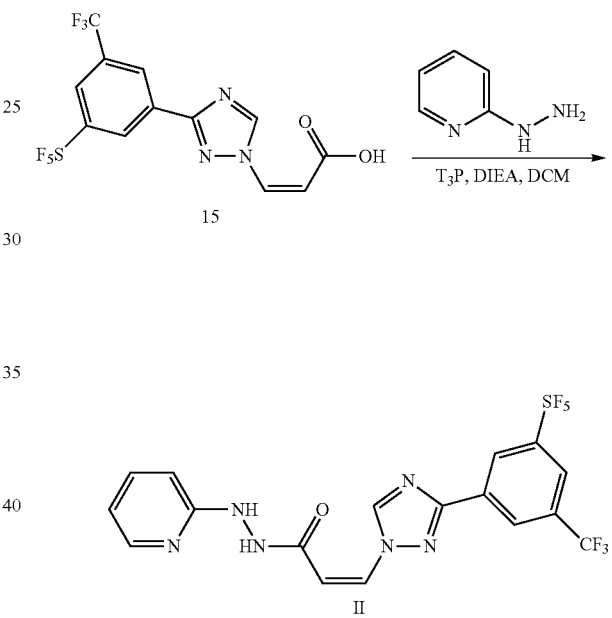

Step 1: (Z)-3-(3-(3-(Pentafluorosulfanyl)-5-(trifluoromethyl)phenyl)-1H-1,2,4-triazol-1-yl)-N'-(pyridin-2-yl)acrylohydrazide (II)

To a solution of compound 15 (40 mg, 0.1 mmol), 2-hydrazineylpyridine (32 mg, 0.3 mmol), DIEA (52 mg, 0.4 mmol) in EA:DCM (1 mL: 1 mL) was added T₃P (190 mg, 0.3 mmol, 50% in EA). The mixture was stirred at −40° C. for 3 h, then the organic solution was concentrated under vacuum. To the residue was added EA (50 mL) and washed with H₂O (3×50 mL). The organic phase was concentrated and purified by prep-TLC (DCM:MeOH:NH₃·H₂O=15:1: 0.1) to obtain the titled compound II (23 mg, 46% yield) as a yellow solid. After that, the product was formed with HCl/Dioxane solution to get a solid product. MS (ESI): [M+H⁺]=501.1. ¹H NMR (400 MHz, DMSO-d₆) δ 11.17 (s, 1H), 9.52 (s, 1H), 8.62 (s, 1H), 8.49 (s, 1H), 8.41 (s, 1H), 8.02 (m, 2H), 7.63 (d, J=10.4 Hz, 1H), 7.20 (m, 1H), 7.04 (m, 1H), 6.12 (d, J=10.5 Hz, 1H).

Example 3

(Z)-3-(3-(3-(Pentafluoro sulfanyl)-5-(trifluoromethyl)phenyl)-1H-1,2,4-triazol-1-yl)-N'-pivaloylacrylohydrazide (III)

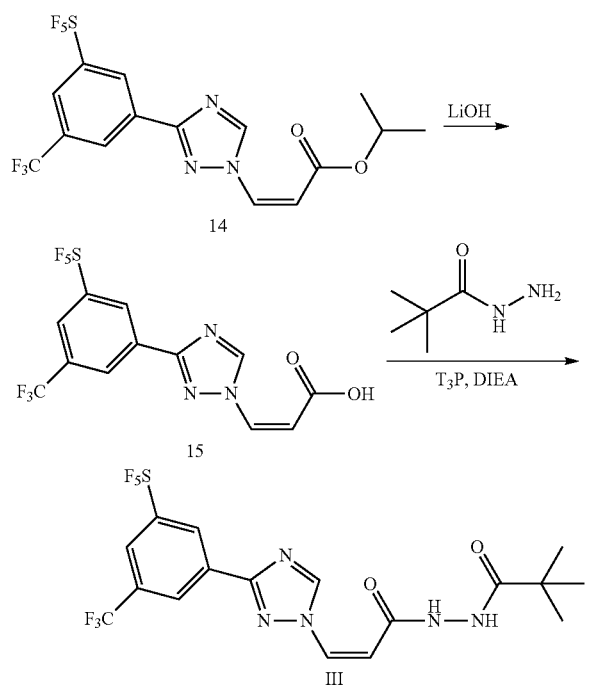

Step 1: (Z)-3-(3-(3-(Pentafluorosulfanyl)-5-(trifluoromethyl)phenyl)-1H-1,2,4-triazol-1-yl)acrylic acid (15)

To a stirred solution of compound 14 (150 mg, 0.33 mmol) in dry THF (15 mL) was added a solution of LiOH (2.6 mL, 2.64 mmol, 1 M) dropwise at 0° C. The reaction was stirred at 25° C. for 3 h. After that, the reaction mixture was quenched with HCl (1 M) until pH=2-3, extracted with EA (3×20 mL). The organic layer was washed with brine (40 mL), dried over $Na_2SO_4$ and concentrated to give compound 15 (125 mg, 92% yield) as a white solid. MS (ESI):[M+H]$^+$=409.9.

Step 2: (Z)-3-(3-(3-(Pentafluorosulfanyl)-5-(trifluoromethyl)phenyl)-1H-1,2,4-triazol-1-yl)-N'-pivaloylacrylohydrazide (III)

To a stirred solution of compound 15 (125 mg, 0.31 mmol) in DCM:EA (5 mL:5 mL, v/v) was cooled to −78° C. and added pivalohydrazide (54.0 mg, 0.46 mmol), DIEA (80.0 mg, 0.62 mmol) and $T_3P$ (395 mg, 0.62 mmol, 50 wt % in EA) at 0° C. The reaction was stirred at 25° C. for 3 h, and then quenched with saturated ammonium chloride (20 mL). The mixture was extracted with DCM and the organic layer washed with brine, dried over $Na_2SO_4$ and concentrated under vacuum to afford crude white solid. The solid was added to MeCN (5 mL) and stirred for 2 h at 25° C. and then filtrated, washed with MeCN (10 mL) to give the titled product III (110 mg, 69% yield) as a white solid. MS (ESI):[M+H]$^+$=506.9. $^1$H NMR (400 MHz, DMSO-$d_6$) δ 10.41 (s, 1H), 9.66 (d, J=8 Hz, 2H), 8.66 (s, 1H), 8.56 (s, 1H), 8.43 (s, 1H), 7.49 (d, J=10.8 Hz, 1H), 6.04 (d, J=10.4 Hz, 1H), 1.17 (s, 9H).

Example 4

(E)-3-(3-(3-(Pentafluorosulfaneyl)-5-(trifluoromethyl)phenyl)-1H-1,2,4-triazol-1-yl)-2-(pyrimidin-5-yl)acrylamide (IV)

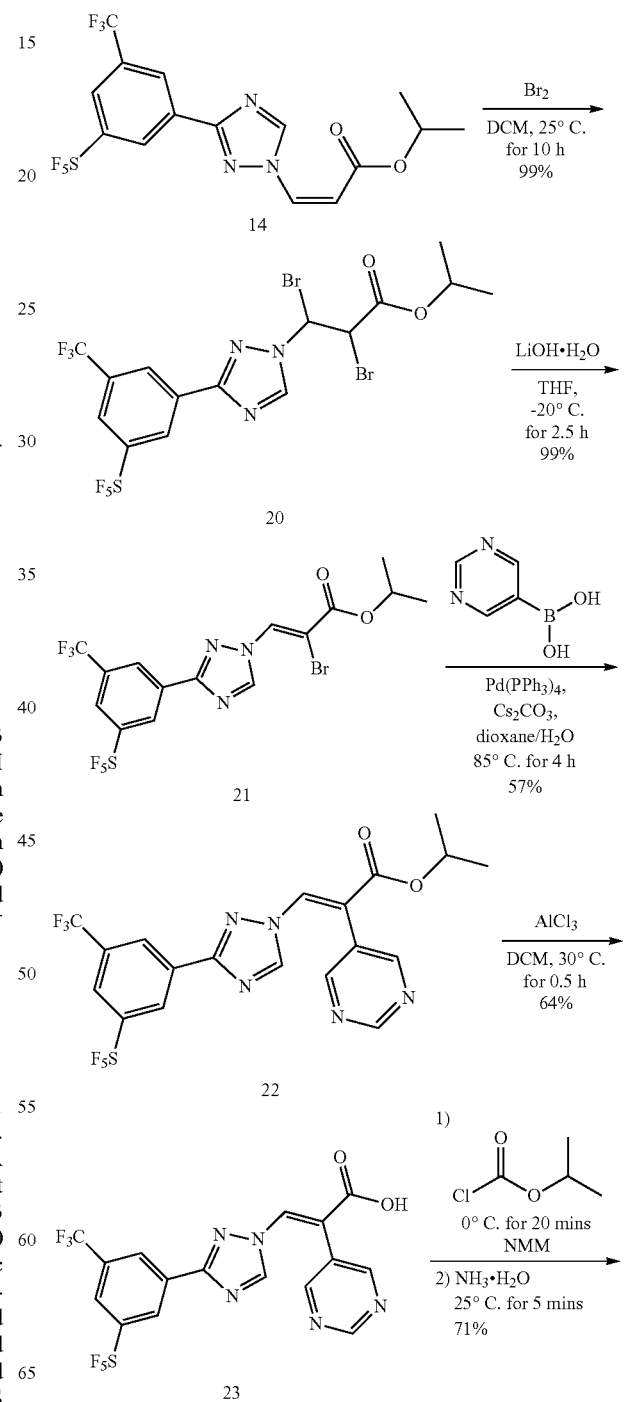

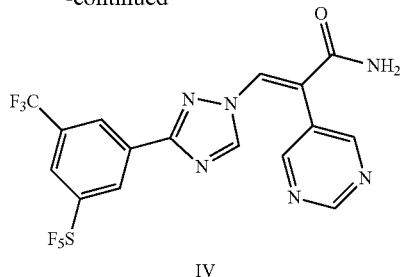

IV

Step 1: Synthesis of isopropyl 2,3-dibromo-3-(3-(3-(pentafluorosulfaneyl)-5-(trifluoromethyl)phenyl)-1H-1,2,4-triazol-1-yl)propanoate (20)

To a solution of compound 14 (9.0 g, 20 mmol) in DCM (60 mL) was added $Br_2$ (6.31 g, 40 mmol) at 0° C. then the mixture was stirred at 25° C. for 10 h. The mixture was washed with $H_2O$ (3×60 mL) and saturated $Na_2S_2O_3$ (60 mL). The organic solution was dried over $Na_2SO_4$, filtered and concentrated to obtain 12.2 g (99% yield) of compound 20 as a yellow solid. MS (ESI): $[M+H]^+=611.9$.

Step 2: Synthesis of isopropyl (Z)-2-bromo-3-(3-(3-(pentafluorosulfaneyl)-5-(trifluoromethyl)phenyl)-1H-1,2,4-triazol-1-yl)acrylate (21)

To a stirred solution of compound 20 (12.2 g, 20 mmol) in THF (120 mL) was added a solution of lithium hydroxide hydrate (13 mL, 40 mmol, 3 M in $H_2O$) dropwise at −20° C. The reaction was stirred at −20° C. for 2.5 h. After that, the reaction mixture was quenched with HCl (1M) until pH=4, and then extracted with EA (200 mL). The organic layer was washed with $H_2O$ (3×100 mL) and brine (3×100 mL), dried over $Na_2SO_4$, filtered and concentrated to give crude product 10.6 g (99% yield) of compound 21 as a yellow solid. MS (ESI): $[M+H]^+=529.9$. $^1H$ NMR (400 MHz, $CDCl_3$) δ 9.47 (s, 1H), 8.76 (s, 1H), 8.75 (s, 1H), 8.59 (s, 1H), 8.07 (s, 1H), 5.25-5.19 (m, 1H), 1.39 (d, J=8 Hz, 6H).

Step 3: Synthesis of isopropyl (E)-3-(3-(3-(pentafluorosulfaneyl)-5-(trifluoromethyl)phenyl)-1H-1,2,4-triazol-1-yl)-2-(pyrimidin-5-yl)acrylate (22)

To a solution of compound 21 (1.06 g, 2 mmol) and pyrimidin-5-ylboronic acid (397 mg, 3.2 mmol) in dioxane:$H_2O$ (10 mL:3 mL) was added $Pd(PPh_3)_4$ (231 mg, 0.2 mmol) and $Cs_2CO_3$ (1.3 g, 4 mmol) under nitrogen atmosphere at 25° C. The reaction mixture was stirred at 85° C. under a nitrogen atmosphere for 4 h, cooled to 25° C. and the organic solution was concentrated. To the residue was added EA (200 mL) and the residue was then washed with $H_2O$ (3×100 mL), and the organic solution was dried over $Na_2SO_4$, filtered and concentrated. The crude product was purified on a silica gel column (PE:EA=2:1) to obtain 603 mg (57% yield) of compound 22 as a white solid. MS (ESI): $[M+H]^+=530.1$. $^1H$ NMR (400 MHz, DMSO-$d_6$) δ 9.26 (s, 1H), 9.19 (s, 1H), 8.78 (s, 2H), 8.68 (s, 1H), 8.38 (s, 1H), 8.13 (s, 1H), 8.09 (s, 1H), 5.13-5.07 (m, 1H), 1.27 (d, J=8 Hz, 6H).

Step 4: Synthesis of (E)-3-(3-(3-(pentafluorosulfaneyl)-5-(trifluoromethyl)phenyl)-1H-1,2,4-triazol-1-yl)-2-(pyrimidin-5-yl)acrylic acid (23)

To a solution of compound 22 (1.16 g, 2.2 mmol) in DCM (100 mL) was added $AlCl_3$ (1.2 g, 8.8 mmol) at 0° C. Then the reaction mixture was stirred at 25° C. for 2.5 h and then warmed to 30° C. and stirred at this temperature for 0.5 h. The reaction was quenched with $H_2O$ (15 mL) and the organic solution was concentrated. To the residue was added EA (100 mL) which was then washed with $H_2O$ (3×100 mL) and HCl solution (30 mL, 1N). The organic solution was dried over $Na_2SO_4$, filtered and concentrated. The crude product was purified on a silica gel column (DCM:MeOH:AcOH=10:1:0.1, v/v) to obtain 684 mg (64% yield) of compound 23 as a white solid. MS (ESI): $[M+H]^+=487.9$.

Step 5: Synthesis of (E)-3-(3-(3-(pentafluorosulfaneyl)-5-(trifluoromethyl)phenyl)-1H-1,2,4-triazol-1-yl)-2-(pyrimidin-5-yl)acrylamide (IV)

To a stirred solution of compound 23 (684 mg, 1.4 mmol) in dry THF (30 mL) was added NMM (283 mg, 2.8 mmol) and isopropyl carbonochloridate (346 mg, 2.8 mmol) dropwise at 0° C. The reaction was stirred at 0° C. for 20 mins. After that, a solution of $NH_4OH$ (294 mg, 8.4 mmol) was added to the mixture at 0° C., and the mixture was stirred another 5 mins at 25° C., and then quenched with $H_2O$ (50 mL), and the organic solution was concentrated. To the residue was added EA (100 mL) and then washed with $H_2O$ (3×100 mL). The organic layer was dried over $Na_2SO_4$ and concentrated. The residue was purified on silica gel column by eluting with EA to obtain 480 mg (71% yield) of Compound IV as a white solid. MS (ESI): $[M+H]^+=486.9$. $^1H$ NMR (400 MHz, DMSO-$d_6$) δ 9.19 (s, 1H), 9.14 (s, 1H), 8.72 (s, 2H), 8.42 (s, 1H), 8.36 (s, 1H), 8.13 (s, 1H), 8.09 (s, 1H), 7.63 (s, 1H), 7.39 (s, 1H).

Example 5

(Z)-3-(3-(3-(Pentafluorosulfaneyl)-5-(trifluoromethyl)phenyl)-1H-1,2,4-triazol-1-yl)-2-(pyrimidin-5-yl)acrylamide (V)

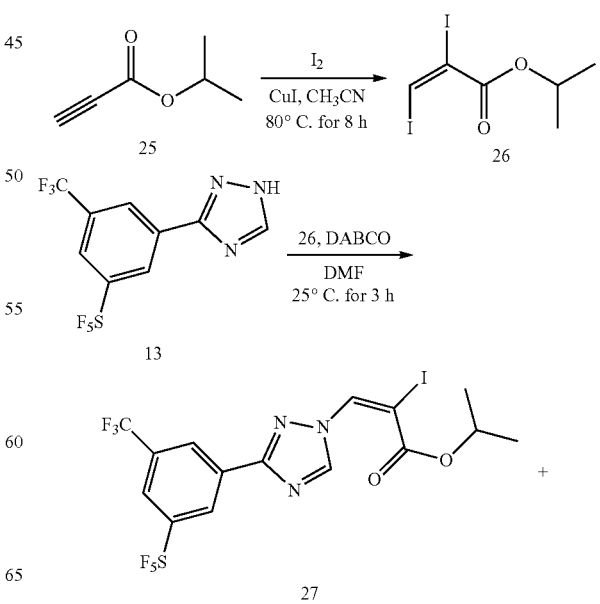

-continued

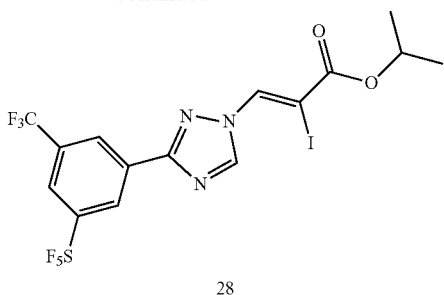

28

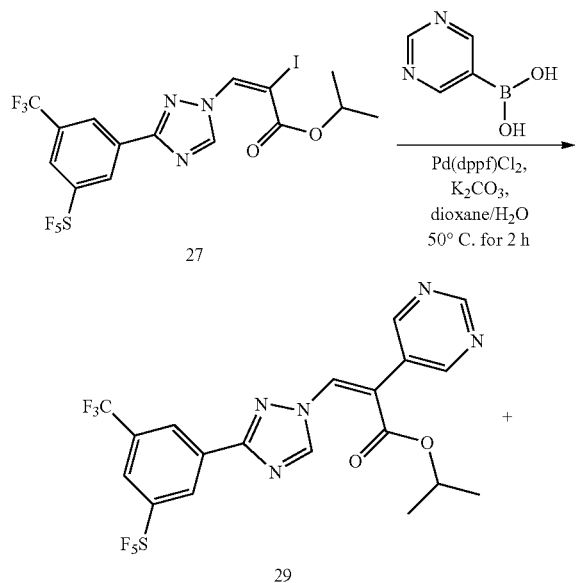

27

29

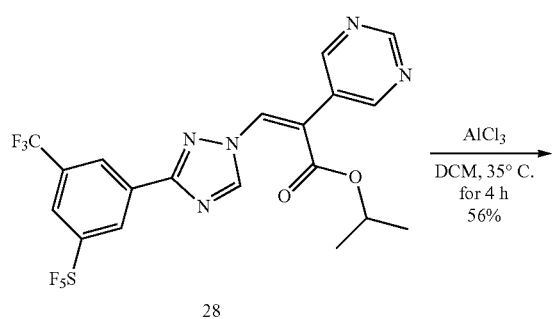

28

-continued

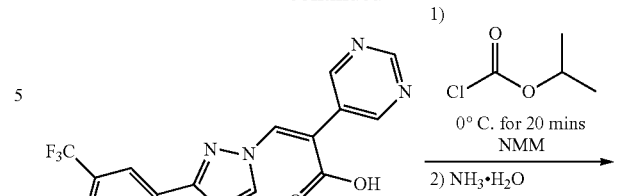

31

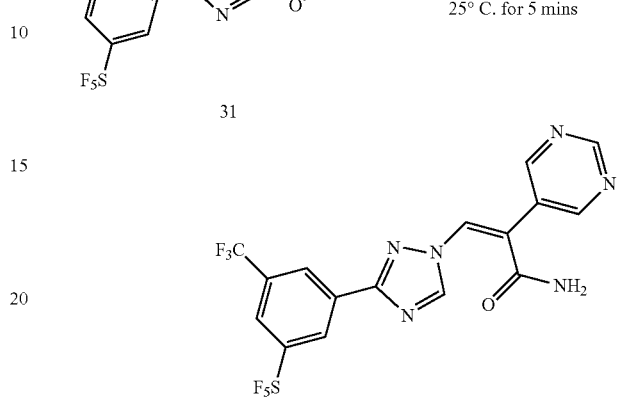

V

Step 1: Synthesis of isopropyl (E)-2,3-diiodoacrylate (26)

To a stirred solution of compound 25 (336 mg, 3 mmol) in CH$_3$CN (5 mL) was added CuI (29 mg, 0.15 mmol) and I$_2$ (1.14 g, 4.5 mmol) at 25° C. The reaction was stirred at 80° C. for 8 h. After that, MTBE (20 mL) was added to the mixture, and the mixture was washed with H$_2$O (3×20 mL) and saturated Na$_2$S$_2$O$_3$ solution (3×20 mL). The organic layer was dried over Na$_2$SO$_4$ and concentrated. The residue was purified on silica gel column by eluting with PE:EA (5:1) to obtain 453 mg (41% yield) of compound 26 as a light-yellow oil. $^1$H NMR (400 MHz, CDCl$_3$) δ 7.61 (s, 1H), 5.19-5.10 (m, 1H), 1.36 (d, J=6.4 Hz, 6H).

Step 2: Synthesis of isopropyl (E)-2-iodo-3-(3-(3-(pentafluorosulfaneyl)-5-(trifluoromethyl)phenyl)-1H-1,2,4-triazol-1-yl)acrylate (27) and isopropyl (Z)-2-iodo-3-(3-(3-(pentafluorosulfaneyl)-5-(trifluoromethyl)phenyl)-1H-1,2,4-triazol-1-yl)acrylate (28)

To a solution of compound 13 (780 mg, 2.3 mmol) in DMF (10 mL) was added DABCO (515 mg, 4.6 mmol) and compound 26 (1.68 g, 4.6 mmol) at 0° C., the mixture was stirred at 80° C. for 0.5 h, quenched with saturated NH$_4$Cl (50 mL), and extracted with EA (100 mL). The organic layer was washed with brine (3×50 mL), dried, filtered and concentrated. The crude product was purified on a silica gel column by eluting with PE:EA (5:1) to obtain the titled compound 27 (1.1 g, 83% yield) as a white solid; MS (ESI): [M+H]$^+$=577.9. $^1$H NMR (400 MHz, CDCl$_3$) δ 8.67 (s, 1H), 8.52 (s, 2H), 8.04 (s, 1H), 7.57 (s, 1H), 5.22-5.16 (m, 1H), 1.34 (d, J=8 Hz, 6H); and compound 28 (210 mg, 16% yield) as a white solid; MS (ESI): [M+H]$^+$=577.9; 1H NMR (400 MHz, CDCl$_3$) δ 9.52 (s, 1H), 8.81 (s, 1H), 8.75 (s, 1H), 8.59 (s, 1H), 8.07 (s, 1H), 5.23-5.17 (m, 1H), 1.38 (d, J=8 Hz, 6H).

Step 3: Synthesis of isopropyl (Z)-3-(3-(3-(pentafluorosulfaneyl)-5-(trifluoromethyl)phenyl)-1H-1,2,4-triazol-1-yl)-2-(pyrimidin-5-yl)acrylate (29) and isopropyl (E)-3-(3-(3-(pentafluorosulfaneyl)-5-(trifluoromethyl)phenyl)-1H-1,2,4-triazol-1-yl)-2-(pyrimidin-5-yl)acrylate (30)

To a solution of compound 27 (58 mg, 0.1 mmol) and pyrimidin-5-ylboronic acid (20 mg, 0.16 mmol) in dioxane:H$_2$O (3 mL:1 mL) was added Pd(dppf)Cl$_2$ (8 mg, 0.01 mmol) and K$_2$CO$_3$ (28 mg, 0.2 mmol) under a nitrogen atmosphere at 25° C. The reaction mixture was stirred at 50° under a nitrogen atmosphere for 2 h, cooled to 25° C., and the organic solution was concentrated. To the residue was added EA (50 mL) which was then washed with H$_2$O (3×50 mL). The organic solution was dried over Na$_2$SO$_4$, filtered and concentrated. The crude product was purified on a silica gel column (PE:EA=2:1) to obtain the titled compound 29 (24 mg, 46% yield) as a white solid' MS (ESI): [M+H]$^+$=530.1; 1H NMR (400 MHz, DMSO-d$_6$) δ 9.21 (s, 1H), 9.02 (s, 1H), 8.92 (s, 2H), 8.59 (s, 1H), 8.47 (s, 1H), 8.43 (s, 1H), 8.19 (s, 1H), 5.21-5.16 (m, 1H), 1.25 (d, J=8 Hz, 6H); and compound 30 (12 mg, 23% yield) as a white solid; MS (ESI): [M+H]$^+$=530.1; $^1$H NMR (400 MHz, DMSO-d$_6$) δ 9.26 (s, 1H), 9.19 (s, 1H), 8.78 (s, 2H), 8.68 (s, 1H), 8.38 (s, 1H), 8.13 (s, 1H), 8.09 (s, 1H), 5.13-5.07 (m, 1H), 1.27 (d, J=8 Hz, 6H).

Step 4: Synthesis of (Z)-3-(3-(3-(pentafluorosulfaneyl)-5-(trifluoromethyl)phenyl)-1H-1,2,4-triazol-1-yl)-2-(pyrimidin-5-yl)acrylic acid (31)

To a solution of compound 28 (20 mg, 2.2 mmol) in DCM (3 mL) was added AlCl$_3$ (21 mg, 0.16 mmol) at 0° C. Then the reaction mixture was stirred at 35° C. for 4 h. The reaction was quenched with H$_2$O (5 mL) and the organic solution was concentrated. To the residue was added EA (10 mL), which was then washed with H$_2$O (3×10 mL) and HCl solution (10 mL, 1N). The organic solution was dried over Na$_2$SO$_4$, filtered and concentrated. The crude product was purified on a silica gel column (DCM:MeOH:AcOH=10:1:0.1, v/v) to obtain 10 mg (56% yield) of compound 31 as a white solid. MS (ESI): [M+H]$^+$=487.9.

Step 5: Synthesis of (Z)-3-(3-(3-(pentafluorosulfaneyl)-5-(trifluoromethyl)phenyl)-1H-1,2,4-triazol-1-yl)-2-(pyrimidin-5-yl)acrylamide (V)

To a stirred solution of compound 31 (10 mg, 0.02 mmol) in dry THF (2 mL) was added NMM (4 mg, 0.04 mmol) and a solution of isopropyl carbonochloridate (5 mg, 0.04 mmol) in THF (1 mL) dropwise at 0° C. The reaction was stirred at 0° C. for 20 mins. After that, a solution of NH$_4$OH (2 mg, 0.04 mmol) was added to the mixture at 0° C., and the mixture was stirred another 5 mins at 0° C., quenched with H$_2$O (5 mL), and the organic solution was concentrated. To the residue was added EA (10 mL), which was then washed with H$_2$O (3×10 mL). The organic layer was dried over Na$_2$SO$_4$ and concentrated. The residue was purified on a silica gel column by eluting with EA to obtain 5 mg (50% yield) of Compound V as a white solid. MS (ESI): [M+H]$^+$=486.9. $^1$H NMR (400 MHz, DMSO-d$_6$) δ 9.22 (s, 1H), 8.96 (s, 3H), 8.66 (s, 1H), 8.52 (s, 1H), 8.44 (s, 1H), 8.10 (s, 1H), 8.00 (s, 1H), 7.93 (s, 1 H).

Example 6

(Z)-3-(3-(3-(pentafluoro sulfaneyl)-5-(trifluoromethyl)phenyl)-1H-1,2,4-triazol-1-yl)-N'-(thiazol-2-yl)acrylohydrazide (VI)

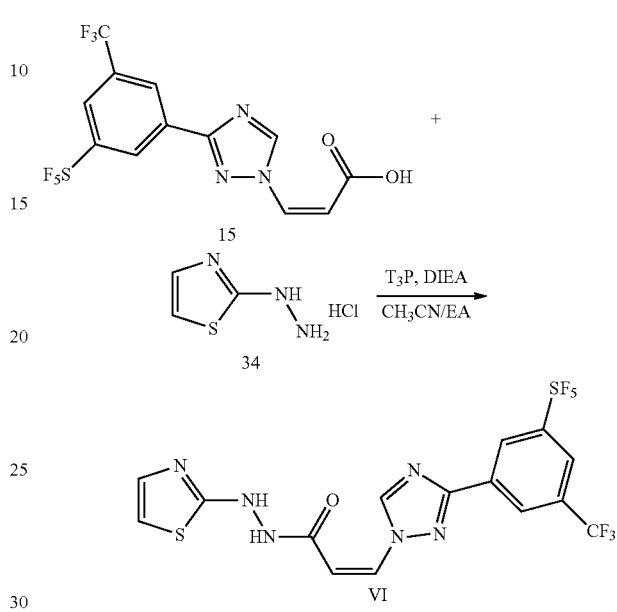

Step 1: Synthesis of (Z)-3-(3-(3-(pentafluorosulfaneyl)-5-(trifluoromethyl)phenyl)-1H-1,2,4-triazol-1-yl)-N'-(thiazol-2-yl)acrylohydrazide (VI)

To a solution of compound 15 (100 mg, 0.24 mmol), 2-hydrazineylthiazole hydrochloride (34) (45 mg, 0.29 mmol) in CH$_3$CN:EA (4 mL:2 mL) was added DIEA (62 mg, 0.48 mmol) and T$_3$P (228 mg, 0.36 mmol, 50% in EA) at 0° C. and then the mixture was stirred at 0° C. for 10 h. The mixture was concentrated. To the residue was added EA (50 mL) and the residue was washed with H$_2$O (3×50 mL). The organic solution was concentrated and purified by prep-TLC(EA) to obtain 8 mg (7% yield) of Compound VI as a gray solid. MS (ESI): [M+H]$^+$=506.9. $^1$H NMR (400 MHz, DMSO-d$_6$) δ 10.92 (s, 1 H), 9.58 (s, 1H), 8.65 (s, 1H), 8.53 (s, 1H), 8.43 (s, 1H), 7.57 (d, J=12 Hz, 1H), 7.22 (d, J=4 Hz, 1 H), 6.89 (d, J=4 Hz, 1H), 6.04 (d, J=8 Hz, 1H).

Example 7

(Z)-N'-(3-(3-(3-(Pentafluorosulfaneyl)-5-(trifluoromethyl)phenyl)-1H-1,2,4-triazol-1-yl)acryloyl)cyclopropanecarbohydrazide (VII)

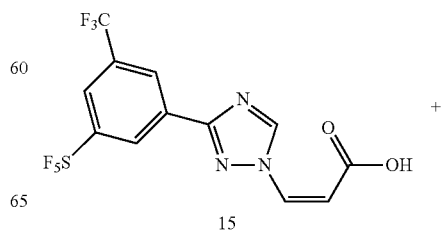

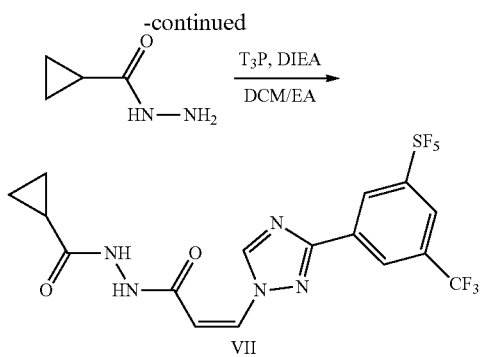

Step 1: Synthesis of (Z)-N'-(3-(3-(3-(pentafluorosulfaneyl)-5-(trifluoromethyl)phenyl)-1H-1,2,4-triazol-1-yl)acryloyl)cyclopropanecarbohydrazide (VII)

To a solution of compound 15 (50 mg, 0.12 mmol), cyclopropanecarbohydrazide (18 mg, 0.18 mmol) in DCM:EA (3 mL:3 mL) was added DIEA (62 mg, 0.48 mmol) and T$_3$P (305 mg, 0.48 mmol, 50% in EA) at 0° C. then the mixture was stirred at 0° C. for 1 h. The mixture was concentrated. To the residue was added EA (50 mL), which was washed with H$_2$O (3×50 mL). The organic solution was concentrated and purified by prep-TLC (EA) to obtain 40 mg (68% yield) of Compound VII as a white solid. MS (ESI): [M+H]$^+$=492.8. $^1$H NMR (400 MHz, DMSO-d$_6$) δ 10.54 (s, 1H), 10.31 (s, 1H), 9.63 (s, 1H), 8.67 (s, 1H), 8.56 (s, 1H), 8.42 (s, 1H), 7.49 (d, J=12 Hz, 1H), 6.02 (d, J=12 Hz, 1H), 1.71-1.67 (m, 1H), 0.79-0.74 (m, 4H).

Example 8

(Z)-N'-Isobutyryl-3-(3-(3-(pentafluoro sulfaneyl)-5-(trifluoromethyl)phenyl)-1H-1,2,4-triazol-1-yl)acrylohydrazide (VIII)

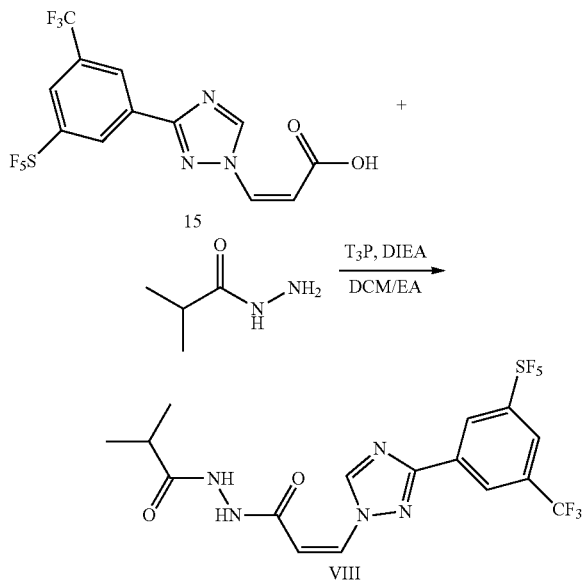

Step 1: (Z)-N'-Isobutyryl-3-(3-(3-(pentafluorosulfaneyl)-5-(trifluoromethyl)phenyl)-1H-1,2,4-triazol-1-yl)acrylohydrazide (VIII)

To a solution of compound 15 (50 mg, 0.12 mmol) and isobutyrohydrazide (18 mg, 0.18 mmol) in DCM:EA (3 mL:3 mL) was added DIEA (62 mg, 0.48 mmol) and T$_3$P (305 mg, 0.48 mmol, 50% in EA) at 0° C. and then the mixture was stirred at 0° C. for 1 h. The mixture was concentrated. To the residue was added EA (50 mL), which was washed with H$_2$O (3×50 mL). The organic solution was concentrated and purified by prep-TLC(EA) to obtain 40 mg (68% yield) of Compound VIII as a white solid. MS (ESI): [M+H]$^+$=494.8. $^1$H NMR (400 MHz, DMSO-d$_6$) δ 10.50 (s, 1H), 10.02 (s, 1H), 9.64 (s, 1H), 8.67 (s, 1H), 8.56 (s, 1H), 8.42 (s, 1H), 7.59 (d, J=12 Hz, 1H), 6.02 (d, J=12 Hz, 1H), 2.55-2.48 (m, 1H), 1.06 (d, J=8 Hz, 6H).

Example 9

(Z)-N'-(3-(3-(3-(Pentafluorosulfaneyl)-5-(trifluoromethyl)phenyl)-1H-1,2,4-triazol-1-yl)acryloyl)butyrohydrazide (IX)

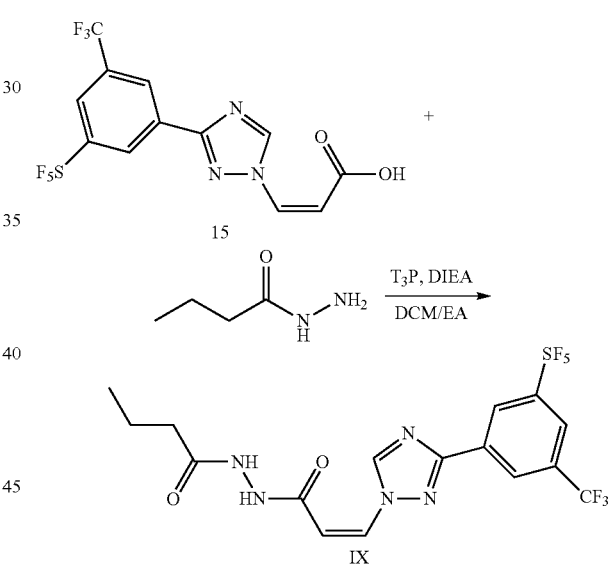

Step 1: (Z)-N'-(3-(3-(3-(Pentafluorosulfaneyl)-5-(trifluoromethyl)phenyl)-1H-1,2,4-triazol-1-yl)acryloyl)butyrohydrazide (IX)

To a solution of compound 15 (50 mg, 0.12 mmol) and butyrohydrazide (18 mg, 0.18 mmol) in DCM:EA (3 mL:3 mL) was added DIEA (62 mg, 0.48 mmol) and T$_3$P (305 mg, 0.48 mmol, 50% in EA) at 0° C. and then the mixture was stirred at 0° C. for 1 h. The mixture was concentrated. To the residue was added EA (50 mL), which was washed with H$_2$O (3×50 mL). The organic solution was concentrated and purified by prep-TLC(EA) to obtain 40 mg (68% yield) of Compound IX as a white solid. MS (ESI): [M+H]$^+$=494.8. $^1$H NMR (400 MHz, DMSO-d$_6$) δ 10.50 (s, 1H), 10.04 (s, 1H), 9.63 (s, 1H), 8.67 (s, 1H), 8.55 (s, 1H), 8.42 (s, 1H), 7.49 (d, J=12 Hz, 1H), 6.03 (d, J=12 Hz, 1H), 2.16 (t, J=8 Hz, 2H), 1.61-1.52 (m, 2H), 0.90 (t, J=8 Hz, 3H).

Example 10

(Z)-N'-(3-(3-(3-(Pentafluorosulfaneyl)-5-(trifluoromethyl)phenyl)-1H-1,2,4-triazol-1-yl)acryloyl)cyclobutanecarbohydrazide (X)

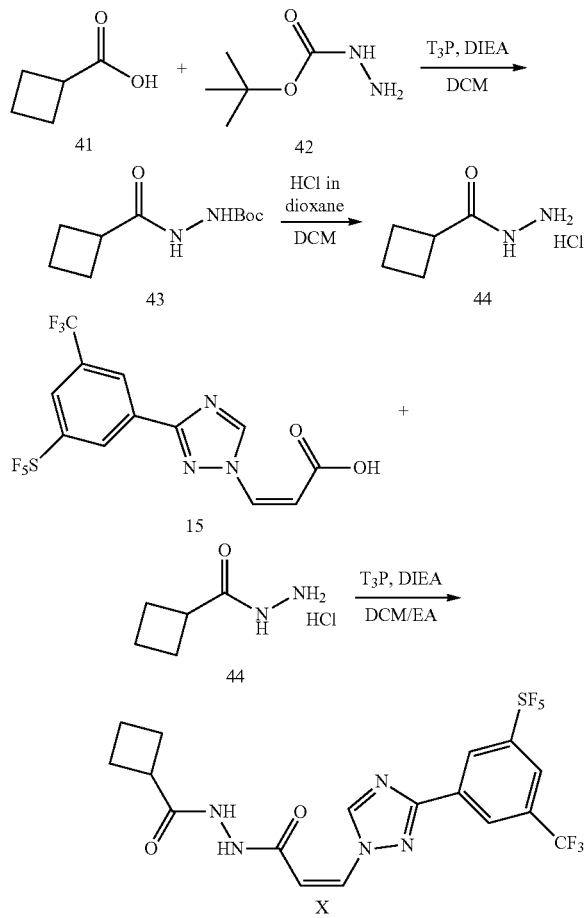

Step 1: Synthesis of tert-butyl 2-(cyclobutanecarbonyl)hydrazine-1-carboxylate (43)

To a solution of compound 41 (500 mg, 5 mmol) and compound 42 (726 mg, 5.5 mmol) in DCM (20 mL) was added DIEA (1.29 g, 10 mmol) and T$_3$P (6.36 g, 10 mmol, 50% in EA) at 0° C. and the mixture was stirred at 25° C. for 1 h. The mixture was washed with H$_2$O (3×20 mL). The organic solution was concentrated and dried in vacuo to obtain 1 g (93% yield) of compound 43 as a white solid. MS (ESI):[M+H]$^+$=215.4.

Step 2: Synthesis of Cyclobutanecarbohydrazide Hydrochloride (44)

To a solution of compound 43 (1 g, 4.7 mmol) in DCM (20 mL) was added an HCl solution in dioxane (10 mL, 4M) and the mixture was stirred at 25° C. for 30 mins. The mixture was concentrated and dried in vacuo to obtain 0.7 g (99% yield) of compound 44 as a white solid. MS (ESI): [M+H]$^+$=115.3.

Step 3: Synthesis of (Z)-N'-(3-(3-(3-(pentafluorosulfaneyl)-5-(trifluoromethyl)phenyl)-1H-1,2,4-triazol-1-yl)acryloyl)cyclobutanecarbohydrazide (X)

To a solution of compound 15 (50 mg, 0.12 mmol) and compound 44 (28 mg, 0.18 mmol) in DCM:EA (3 mL:3 mL) was added DIEA (62 mg, 0.48 mmol) and T$_3$P (305 mg, 0.48 mmol, 50% in EA) at 0° C. and then the mixture was stirred at 0° C. for 1 h. The mixture was concentrated. To the residue was added EA (50 mL), which was washed with H$_2$O (3×50 mL). The organic solution was concentrated and purified by prep-TLC (EA) to obtain 11 mg (18% yield) of Compound X as a white solid. MS (ESI): [M+H]$^+$=506.9. $^1$H NMR (400 MHz, DMSO-d$_6$) δ 10.49 (s, 1H), 9.93 (s, 1H), 9.64 (s, 1H), 8.67 (s, 1H), 8.56 (s, 1H), 8.42 (s, 1H), 7.49 (d, J=12 Hz, 1H), 6.02 (d, J=12 Hz, 1H), 3.18-3.10 (m, 1H), 2.23-1.90 (m, 6H).

Example 11

(Z)-1-Methyl-N'-(3-(3-(3-(pentafluorosulfaneyl)-5-(trifluoromethyl)phenyl)-1H-1,2,4-triazol-1-yl)acryloyl)cyclopropane-1-carbohydrazide (XI)

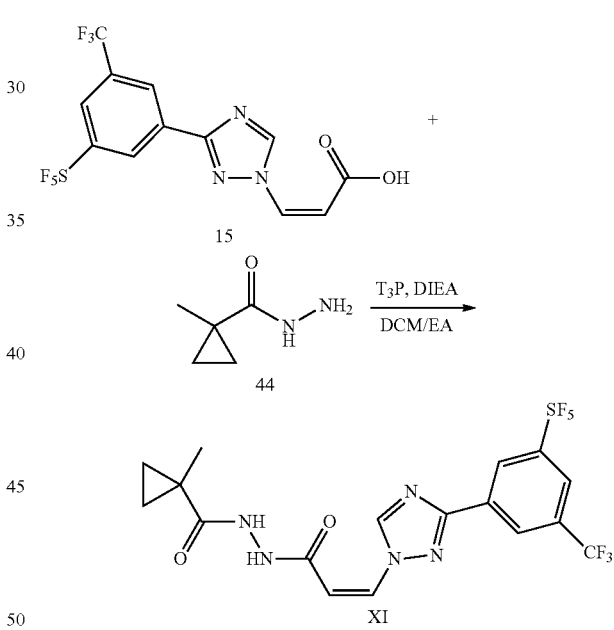

Step 1: (Z)-1-Methyl-N'-(3-(3-(3-(pentafluoro sulfaneyl)-5-(trifluoromethyl)phenyl)-1H-1,2,4-triazol-1-yl)acryloyl)cyclopropane-1-carbohydrazide (XI)

To a solution of compound 15 (40 mg, 0.1 mmol) and compound 44 (17 mg, 0.15 mmol) in DCM:EA (3 mL:3 mL) was added DIEA (52 mg, 0.4 mmol) and T$_3$P (254 mg, 0.4 mmol, 50% in EA) at 0° C. and then the mixture was stirred at 0° C. for 1 h. The mixture was concentrated. To the residue was added EA (50 mL), which was washed with H$_2$O (3×50 mL). The organic solution was concentrated and purified by prep-TLC (EA) to obtain 21 mg (41% yield) of Compound XI as a white solid. MS (ESI): [M++H]$^+$=506.9. $^1$H NMR (400 MHz, DMSO-d$_6$) δ 10.35 (s, 1H), 9.65 (s, 1H), 9.62 (s, 1H), 8.65 (s, 1H), 8.54 (s, 1H), 8.40 (s, 1H), 7.49 (d, J=8 Hz, 1H), 6.02 (d, J=8 Hz, 1H), 1.31 (s, 3H), 1.02 (s, 2H), 0.62 (s, 2H).

Example 12

(Z)-N'-(3-Chloro-2-(hydroxymethyl)-2-methylpropanoyl)-3-(3-(3-(pentafluorosulfaneyl)-5-(trifluoromethyl)phenyl)-1H-1,2,4-triazol-1-yl)acrylohydrazide (XII)

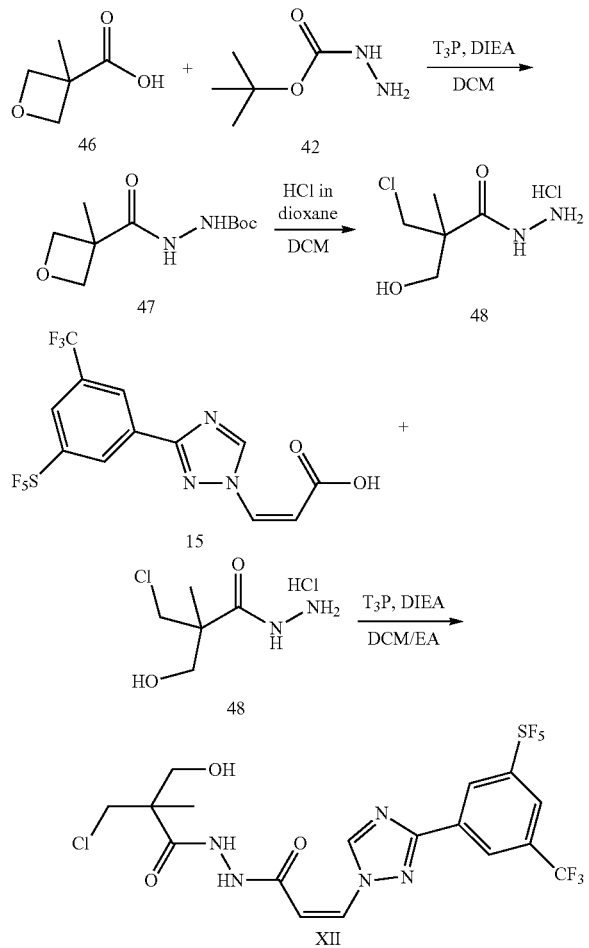

Step 1: Synthesis of tert-butyl 2-(3-methyloxetane-3-carbonyl)hydrazine-1-carboxylate (47)

To a solution of compound 46 (116 mg, 1 mmol) and compound 42 (145 mg, 1.1 mmol) in DCM (10 mL) was added DIEA (258 mg, 2 mmol) and T₃P (1.27 g, 2 mmol, 50% in EA) at 0° C. and then the mixture was stirred at 25° C. for 1 h. The mixture was washed with H₂O (3×15 mL). The organic solution was concentrated and dried in vacuo to obtain 230 mg (99% yield) of compound 47 as a white solid. MS (ESI): [M+H]⁺=231.4.

Step 2: Synthesis of 3-chloro-2-(hydroxymethyl)-2-methylpropanehydrazide hydrochloride (48)

To a solution of compound 47 (230 mg, 1 mmol) in DCM (10 mL) was added the HCl solution in dioxane (10 mL, 4M) and then the mixture was stirred at 25° C. for 30 mins. The mixture was concentrated and dried in vacuo to obtain 200 mg (99% yield) of compound 48 as a white solid. MS (ESI): [M+H]⁺=166.3.

Step 3: Synthesis of (Z)-N'-(3-chloro-2-(hydroxymethyl)-2-methylpropanoyl)-3-(3-(3-(pentafluorosulfaneyl)-5-(trifluoromethyl)phenyl)-1H-1,2,4-triazol-1-yl)acrylohydrazide (XII)

To a solution of compound 15 (59 mg, 0.14 mmol) and compound 48 (45 mg, 0.22 mmol) in DCM:EA (3 mL:3 mL) was added DIEA (72 mg, 0.56 mmol) and T₃P (356 mg, 0.56 mmol, 50% in EA) at 0° C. and then the mixture was stirred at 0° C. for 1 h. The mixture was concentrated. To the residue was added EA (50 mL), which was washed with H₂O (3×50 mL). The organic solution was concentrated and purified by prep-TLC(EA) to obtain 10 mg (13% yield) of Compound XII as a white solid. MS (ESI): [M+H]⁺=559.0. ¹H NMR (400 MHz, DMSO-d₆) δ 10.65 (s, 1H), 9.88 (s, 1H), 9.63 (s, 1H), 8.66 (s, 1H), 8.55 (s, 1H), 8.40 (s, 1H), 7.49 (d, J=12 Hz, 1H), 6.03 (d, J=12 Hz, 1H), 5.16 (s, 1H), 3.81 (s, 2H), 3.59 (s, 2H), 1.22 (s, 3H).

Example 13

General Synthesis of (Z)-3-methyl-N'-(3-(3-(3-(pentafluorosulfaneyl)-5-(trifluoromethyl)phenyl)-1H-1,2,4-Triazol-1-Yl)Acryloyl)Butanehydrazide (XIII)

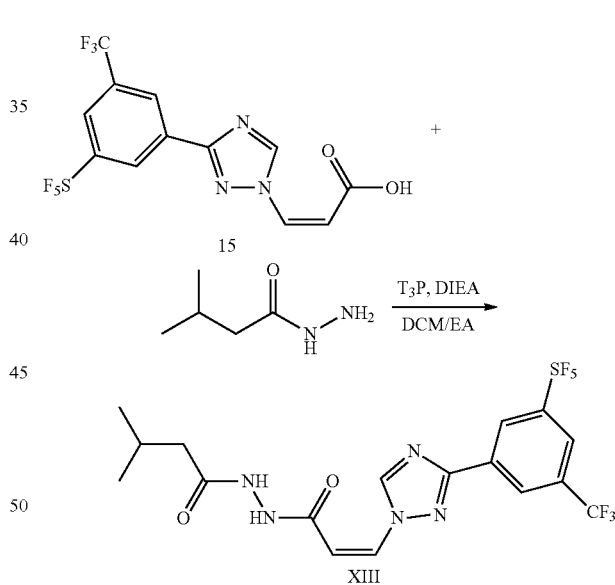

Step 1: Synthesis of (Z)-3-methyl-N'-(3-(3-(3-(pentafluorosulfaneyl)-5-(trifluoromethyl)phenyl)-1H-1,2,4-triazol-1-yl)acryloyl)butanehydrazide (XIII)

To a solution of compound 15 (50 mg, 0.12 mmol) and 3-methylbutanehydrazide (21 mg, 0.18 mmol) in DCM:EA (3 mL:3 mL) was added DIEA (62 mg, 0.48 mmol) and T₃P (305 mg, 0.48 mmol, 50% in EA) at 0° C. and then the mixture was stirred at 0° C. for 1 h. The mixture was concentrated. To the residue was added EA (50 mL), which was washed with H₂O (3×50 mL). The organic solution was concentrated and purified by prep-TLC(EA) to obtain 37 mg (61% yield) of Compound XIII as a white solid. MS (ESI): [M+H]$^+$=508.9. $^1$H NMR (400 MHz, DMSO-d$_6$) δ 10.50 (s, 1H), 10.02 (s, 1H), 9.63 (s, 1H), 8.67 (s, 1H), 8.55 (s, 1H), 8.42 (s, 1H), 7.49 (d, J=12 Hz, 1H), 6.03 (d, J=12 Hz, 1H), 2.07-1.95 (m, 3H), 0.93 (d, J=8 Hz, 6H).

Example 14

General Synthesis of (Z)-N'-acetyl-3-(3-(3-(pentafluorosulfaneyl)-5-(trifluoromethyl)phenyl)-1H-1,2,4-Triazol-1-Yl)Acrylohydrazide (XIV)

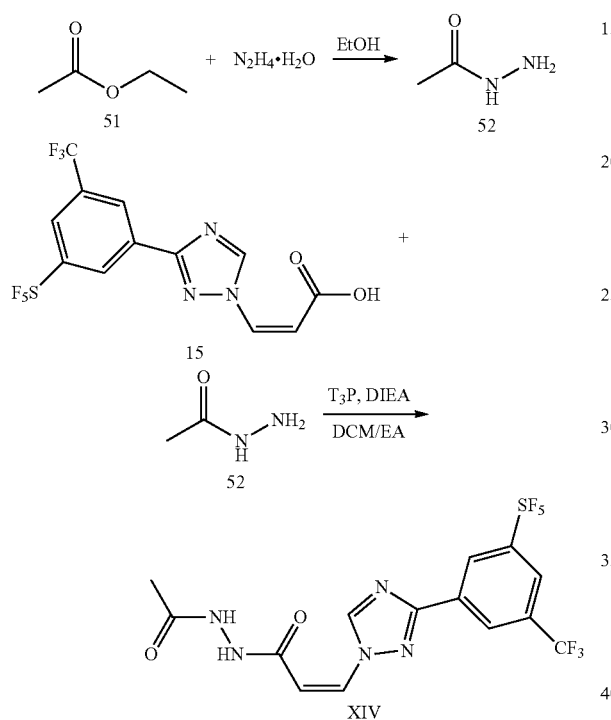

Step 1: Synthesis of Acetohydrazide (52)

To a solution of compound 51 (2.4 g, 27.3 mmol) in EtOH (5 mL) was added hydrazine hydrate (1.03 g, 20.6 mmol) and then the mixture was stirred at 80° C. for 12 h. The mixture was concentrated and dried over vacuo to obtain 1.3 g (86% yield) of compound 52 as a white solid.

Step 2: Synthesis of (Z)-N'-acetyl-3-(3-(3-(pentafluorosulfaneyl)-5-(trifluoromethyl)phenyl)-1H-1,2,4-triazol-1-yl)acrylohydrazide (XIV)

To a solution of compound 15 (50 mg, 0.12 mmol) and compound 52 (14 mg, 0.18 mmol) in DCM:EA (3 mL:3 mL) was added DIEA (62 mg, 0.48 mmol) and T$_3$P (305 mg, 0.48 mmol, 50% in EA) at 0° C. and then the mixture was stirred at 0° C. for 1 h. The mixture was concentrated. To the residue was added EA (50 mL), which was washed with H$_2$O (3×50 mL). The organic solution was concentrated and purified by prep-TLC(EA) to obtain 20 mg (36% yield) of Compound XIV as a white solid. MS (ESI): [M+H]$^+$=466.8. $^1$H NMR (400 MHz, DMSO-d$_6$) δ 10.51 (s, 1H), 10.09 (s, 1H), 9.62 (s, 1H), 8.66 (s, 1H), 8.55 (s, 1H), 8.42 (s, 1H), 7.49 (d, J=12 Hz, 1H), 6.03 (d, J=12 Hz, 1H), 1.91 (s, 3H).

Example 15

(Z)-3-(3-(3-(Pentafluorosulfaneyl)-5-(trifluoromethyl)phenyl)-1H-1,2,4-triazol-1-yl)-N'-propionylacrylohydrazide (XV)

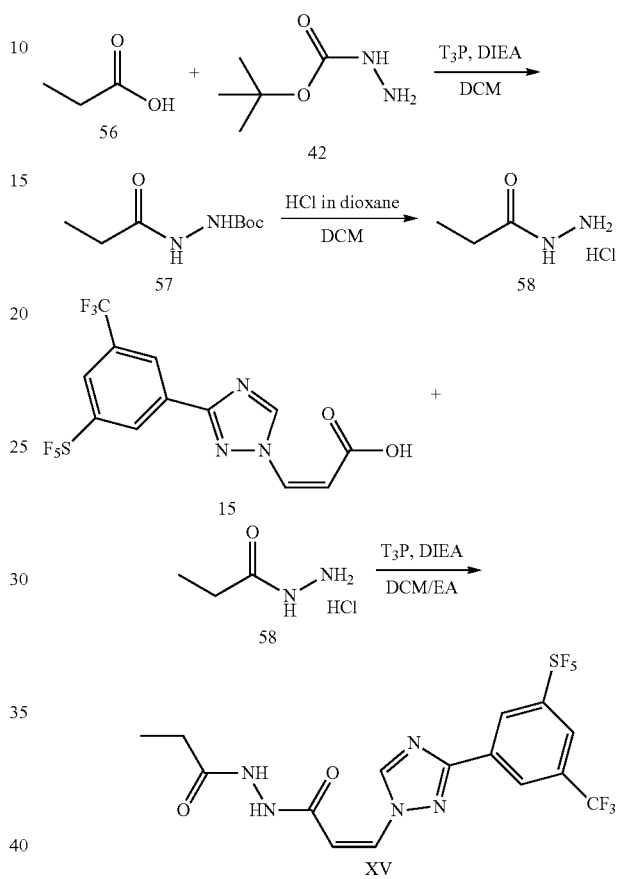

Step 1: Synthesis of tert-butyl 2-propionylhydrazine-1-carboxylate (57)

To a solution of compound 56 (74 mg, 1 mmol) and compound 42 (145 mg, 1.1 mmol) in DCM (10 mL) was added DIEA (258 mg, 2 mmol) and T$_3$P (1.27 g, 2 mmol, 50% in EA) at 25° C. and then the mixture was stirred at 25° C. for 1 h. The mixture was washed with H$_2$O (3×20 mL). The organic solution was concentrated and dried in vacuo to obtain 190 mg (99% yield) of compound 57 as a white solid. MS (ESI): [M+H]$^+$=192.3.

Step 2: Synthesis of Propionohydrazide Hydrochloride (58)

To a solution of compound 57 (190 mg, 1 mmol) in DCM (10 mL) was added an HCl solution in dioxane (10 mL, 4M) and then the mixture was stirred at 25° C. for 30 mins. The mixture was concentrated and dried over vacuo to obtain 120 mg (94% yield) of compound 58 as a white solid.

Step 3: Synthesis of (Z)-3-(3-(3-(pentafluorosulfaneyl)-5-(trifluoromethyl)phenyl)-1H-1,2,4-triazol-1-yl)-N'-propionylacrylohydrazide (XV).

To a solution of compound 15 (50 mg, 0.12 mmol) and compound 58 (23 mg, 0.18 mmol) in DCM:EA (3 mL:3 mL) was added DIEA (62 mg, 0.48 mmol) and $T_3P$ (305 mg, 0.48 mmol, 50% in EA) at 0° C. and then the mixture was stirred at 0° C. for 1 h. The mixture was concentrated. To the residue was added EA (50 mL), which was washed with $H_2O$ (3×50 mL). The organic solution was concentrated and purified by prep-TLC(EA) to obtain 24 mg (42% yield) of Compound XV as a white solid. MS (ESI): $[M+H]^+$=480.9. $^1H$ NMR (400 MHz, DMSO-$d_6$) δ 10.50 (s, 1H), 10.03 (s, 1H), 9.63 (s, 1H), 8.67 (s, 1H), 8.56 (s, 1H), 8.42 (s, 1H), 7.49 (d, J=12 Hz, 1H), 6.03 (d, J=12 Hz, 1H), 2.20 (q, J=8 Hz, 2H), 1.05 (t, J=8 Hz, 3H).

Example 16

(Z)-N'-(3-(3-(3-(Pentafluorosulfaneyl)-5-(trifluoromethyl)phenyl)-1H-1,2,4-triazol-1-yl)acryloyl)cyclopentanecarbohydrazide (XVI)

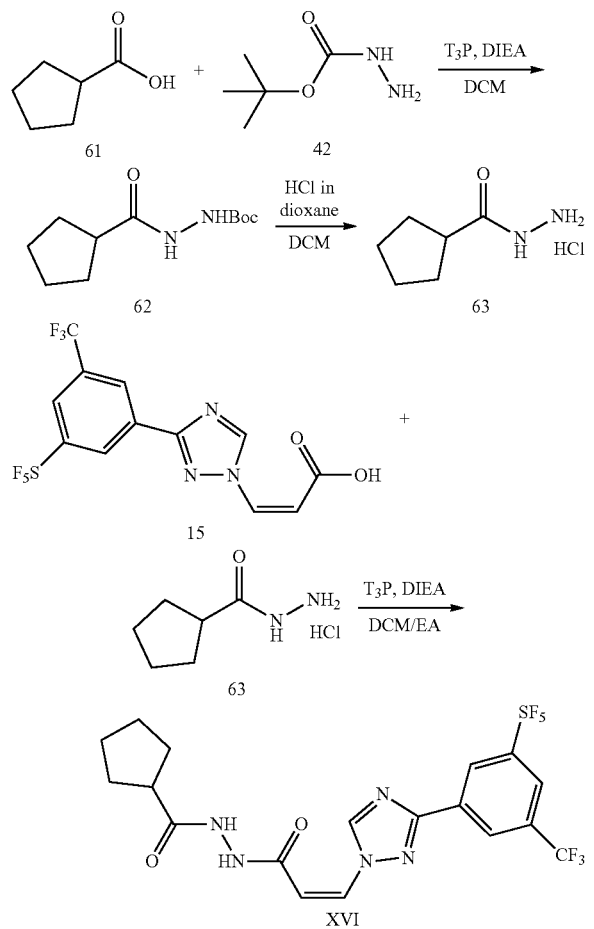

Step 1: Synthesis of Tert-Butyl 2-(Cyclopentanecarbonyl)Hydrazine-1-Carboxylate (62)

To a solution of compound 61 (114 mg, 1 mmol) and compound 42 (145 mg, 1.1 mmol) in DCM (10 mL) was added DIEA (258 mg, 2 mmol) and $T_3P$ (1.27 g, 2 mmol, 50% in EA) at 25° C. and then the mixture was stirred at 25° C. for 1 h. The mixture was washed with $H_2O$ (3×20 mL). The organic solution was concentrated and dried in vacuo to obtain 220 mg (96% yield) of compound 62 as a white solid. MS (ESI): $[M+H]^+$=229.3.

Step 2: Synthesis of Cyclopentanecarbohydrazide Hydrochloride (63)

To a solution of compound 62 (220 mg, 1 mmol) in DCM (10 mL) was added an HCl solution in dioxane (10 mL, 4M) and then the mixture was stirred at 25° C. for 30 mins. The mixture was concentrated and dried in vacuo to obtain 160 mg (97% yield) of compound 63 as a white solid. MS (ESI): $[M+H]^+$=129.3.

Step 3: Synthesis of (Z)-N'-(3-(3-(3-(pentafluoro sulfaneyl)-5-(trifluoromethyl)phenyl)-1H-1,2,4-triazol-1-yl)acryloyl)cyclopentanecarbohydrazide (XVI)

To a solution of compound 15 (50 mg, 0.12 mmol), and compound 63 (30 mg, 0.18 mmol) in DCM:EA (3 mL:3 mL) was added DIEA (62 mg, 0.48 mmol) and $T_3P$ (305 mg, 0.48 mmol, 50% in EA) at 0° C. and then the mixture was stirred at 0° C. for 1 h. The mixture was concentrated. To the residue was added EA (50 mL), which was washed with $H_2O$ (3×50 mL). The organic solution was concentrated and purified by prep-TLC(EA) to obtain 30 mg (48% yield) of Compound XVI as a white solid. MS (ESI): $[M+H]^+$=520.9. $^1H$ NMR (400 MHz, DMSO-$d_6$) δ 10.50 (s, 1H), 10.02 (s, 1H), 9.65 (s, 1H), 8.67 (s, 1H), 8.56 (s, 1H), 8.42 (s, 1H), 7.49 (d, J=12 Hz, 1H), 6.02 (d, J=12 Hz, 1H), 2.72-2.65 (m, 1H), 1.84-1.52 (m, 8H).

Example 17

(Z)-N'-(2-Methyl-2-(methyl-$d_3$)propanoyl-3,3,3-$d_3$)-3-(3-(3-(pentafluoro sulfaneyl)-5-(trifluoromethyl)phenyl)-1H-1,2,4-triazol-1-yl)acrylohydrazide (XVII)

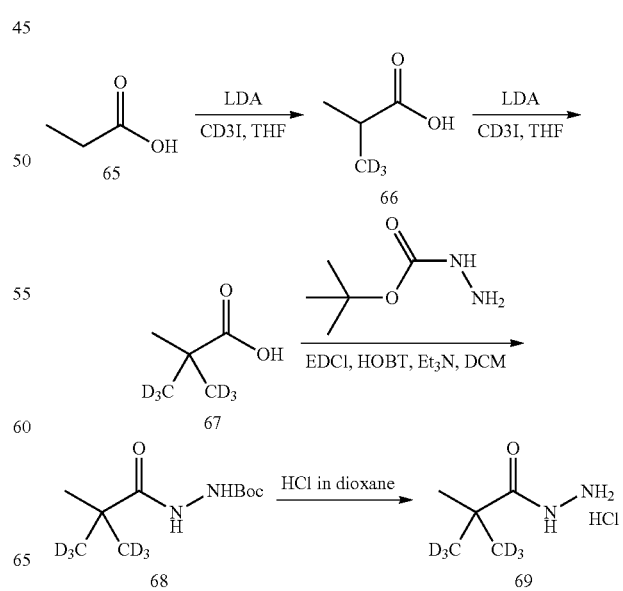

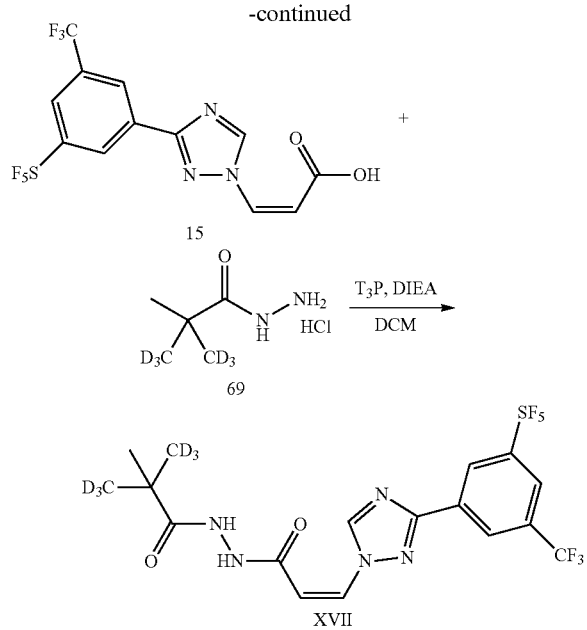

Step 1: Synthesis of 2-methylpropanoic-3,3,3-d₃ acid (66)

To a solution of LDA (50 mL, 74.3 mmol) in THF (150 mL) was added compound 65 (2.2 g, 29.7 mmol) at 0° C. under a nitrogen atmosphere and then the mixture was stirred at 80° C. for 2 h, cooled to 0° C., and then CD₃I (4.8 g, 32.7 mmol) was added dropwise and stirred at 80° C. for 10 h. To the mixture was added H₂O (50 mL), which was extracted with EA (50 mL). The inorganic layer was acidified with 1N HCl to pH=4 and then extracted with EA (50 mL). The organic solution was dried over Na₂SO₄, filtered, and concentrated to obtain 1.68 g (62% yield) of compound 66 as a light-yellow oil. ¹H NMR (400 MHz, CDCl₃) δ 2.57 (q, J=8 Hz, 1H), 1.19 (d, J=8 Hz, 3H).

Step 2: Synthesis of 2-methyl-2-(methyl-d₃)propanoic-3,3,3-d₃ acid (67)

To a solution of LDA (31 mL, 46.3 mmol) in THF (90 mL) was added compound 66 (1.68 g, 18.5 mmol) at 0° C. under a nitrogen atmosphere and then the mixture was stirred at 80° C. for 2 h, cooled to 0° C., and then CD₃I (3 g, 20.8 mmol) was added dropwise and stirred at 80° C. for 10 h. To the mixture was added H₂O₂O (50 mL) then extracted with EA (50 mL). The inorganic layer was acidified with 1N HCl to pH=4 and then extracted with EA (50 mL). The organic solution was dried over Na₂SO₄, filtered, and concentrated to obtain 1.17 g (59% yield) of compound 67 as a yellow oil. ¹H NMR (400 MHz, CDCl₃) δ 1.22 (s, 3H).

Step 3: Synthesis of tert-butyl 2-(2-methyl-2-(methyl-d₃)propanoyl-3,3,3-d₃)hydrazine-1-carboxylate (68)

To a solution of compound 67 (540 mg, 5 mmol), tert-butyl hydrazinecarboxylate (660 mg, 5 mmol), and Et₃N (1.01 g, 10 mmol) in DCM (50 mL) was added EDCl (1.05 g, 5.5 mmol) and HOBT (740 mg, 5.5 mmol) at 25° C. and then the mixture was stirred at 25° C. for 12 h. Then the mixture was washed with H₂O (3×50 mL). The organic solution was concentrated and purified on silica gel column by eluting with PE:EA (5:1 to 3:1) to obtain 412 mg (37% yield) of compound 68 as a white solid. MS (ESI): [M+H]⁺=223.5. ¹H NMR (400 MHz, CDCl₃) δ 7.37 (s, 1H), 6.48 (s, 1H), 1.47 (s, 9H), 1.24 (s, 3H).

Step 4: Synthesis of 2-methyl-2-(methyl-d₃)propanehydrazide-3,3,3-d₃ hydrochloride (69)

To a single-neck flask was added compound 68 (412 mg, 1.9 mmol) and HCl solution in dioxane (10 mL, 4M). The mixture was stirred at 25° C. for 1 h. The mixture was concentrated and dried in vacuo to obtain 300 mg (99% yield) of compound 69 as a white solid. MS (ESI): [M+H]⁺=123.3.

Step 5: Synthesis of (Z)-N'-(2-methyl-2-(methyl-d₃)propanoyl-3,3,3-d₃)-3-(3-(3-(pentafluorosulfaneyl)-5-(trifluoromethyl)phenyl)-1H-1,2,4-triazol-1-yl)acrylohydrazide (XVII)

To a solution of compound 15 (700 mg, 1.7 mmol) and compound 69 (300 mg, 1.88 mmol) in DCM (50 mL) was added DIEA (877 mg, 6.8 mmol) and T₃P (4.3 g, 6.8 mmol, 50% in EA) at −78° C., the mixture was stirred at −78° C. for 30 mins, and then warmed to 0° C. and stirred for 1 h. The mixture was concentrated at 35° C. in vacuo. To the residue was added EA (100 mL) and washed with H₂O (3×100 mL) and brine (3×100 mL). The organic solution was dried over Na₂SO₄, filtered and concentrated to obtain a crude product which was triturated with CH₃CN (15 mL) for 12 h, filtered. The filter cake was collected and triturated with DCM (15 mL) for 12 h and then filtered. The filter cake was washed with DCM (15 mL), collected and dried in vacuo for 5 h to obtain 670 mg (77% yield) of Compound XVII as a white solid. MS (ESI): [M+H]⁺=514.9. ¹H NMR (400 MHz, DMSO-d₆) δ 10.36 (s, 1H), 9.67 (s, 1H), 9.64 (s, 1H), 8.67 (s, 1H), 8.56 (s, 1H), 8.44 (s, 1H), 7.49 (d, J=12 Hz, 1H), 6.02 (d, J=12 Hz, 1H), 1.16 (s, 3H).

Example 18

Synthesis of (Z)-3-(3-(3,5-bi s (trifluoromethyl)phenyl)-1H-1,2,4-triazol-1-yl)-2-(pyrimidin-5-yl)acrylamide (XXIV)

Compound XXIV was synthesized adapting the procedure described in Example 4 except that compound 14 was replaced with the —CF₃ analog, isopropyl (Z)-3-(3-(3,5-bis (trifluoromethyl)phenyl)-1H-1,2,4-triazol-1-yl)acrylate.

Example 19

Inhibition of Cell Proliferation Assay

CellTiter-Glo® Luminescent Cell Viability assay (with Promega CellTiter 96® Luminescent CellTiter-Glo® kit) was used to study the proliferation inhibition by test compounds. Compounds were resuspended in DMSO to make a 25 mM stock suspension. Cells of cancer cell lines or normal tissues were seeded in 96-well plates at 1,500 to 5,000 cells/well overnight. Compounds were 2- or 3-fold diluted serially to obtain 10 concentrations. Then, the drugs were added to the cell wells by Bravo (Agilent) and incubated for 72 hours. The cells were lysed by adding CellTiter-Glo®

Reagent (per manufacturer's instructions) and subsequently, the luminescence was read using EnVision® (PerkinElmer). The percent of growth was calculated as follows. DMSO-treated cells were employed as vehicle control (High control, HC) and culture medium alone was employed as background (Low control, LC). % growth=100×(Lum sample−Lum LC)/(Lum HC−Lum LC). The $IC_{50}$ was calculated by concentration–response curve fitting using Graphpad Prism.

Hematological cancer cell lines tested included OCI-AML3, MV-4-11, KG-1, Kasumi-1, K562, THP-1; solid cancer cell lines tested included U87MG, U251, T98G, LN229, A172, H460, H2009, A549; normal cell lines tested included HCN2 and 3T3-L1. The results were shown in Table 1, where the test compounds showed growth inhibition on cancer cell lines of brain, lung, and blood. However, they were not toxic to in vitro cultured normal cells.

TABLE 1

Growth inhibition by test compounds in cancer and normal cell lines (IC50, nM).

| Cell lines | Compound I | Compound II | Compound III | Compound IV |
|---|---|---|---|---|
| U87MG | 591.5 | 630 | 1743.8 | 194 |
| T98G | NA | 1916 | 6253 | NA |
| LN-229 | NA | 805 | 1796 | NA |
| U251 | NA | 2338 | 3770 | NA |
| A549 | 1489 | NA | NA | 1865 |
| H460 | 294 | NA | NA | 306 |
| H2009 | 521 | NA | NA | 453 |
| MV411 | NA | NA | NA | 110 |
| KG1 | NA | NA | NA | 698 |
| Kasumi-1 | NA | NA | NA | 124 |
| OCI-AML3 | NA | NA | NA | 341 |
| K562 | NA | NA | NA | 1748 |
| THP-1 | NA | NA | NA | 838 |
| HCN2 | 25813.75 | 44748.65 | >50000 | NA |
| 3T3-L1 | >50000 | NA | NA | NA |

NA. Not available.

Example 20

REV-GFP Translocation Assay

Previous studies suggested that the nuclear accumulation of REV cargo is a marker of CRM1 inhibition. SINE (Selective Inhibitor of Nuclear Export) treatment induced a clear and rapid shift of REV from a cytoplasmic localization to the nucleus in a dose dependent manner. To evaluate XPO1 inhibition by test compounds, REV-GFP U2OS clones were generated by HD Biosciences Co. LTD in China, and cells were cultured with growth medium. Then cells were seeded into 96 well plates at 7,000 cells/well in 100 μL growth medium in 37° C., 5% $CO_2$ incubator overnight. The highest Leptomycin B (LMB) concentration was set to 50 nM and serially diluted as the positive control, while the highest concentrations of other compounds were set to 10 μM. The cells treated with various drugs or DMSO, were incubated at 37° C. and 5% $CO_2$ for 1 h. Then, cells were fixed with 4% formaldehyde for 15 min at room temperature.

The cells were washed and stained with 100 μL Hoechst 33342 working solution for 10 min at room temperature in dark, after which the cell fluorescence was imaged with the High-Content Imaging System, ImageXpress® (Molecular Devices) using the 20× objective. The filters were set for Hoechst (350/461 nm) and GFP/FITC (488/509 nm) (wavelength for excitation and emission maxima). The % effect of REV nuclear translocation was calculated with the following formula: % effect=$(I_{TEST}-I_{CTRL})/(I_{LMB}-I_{CTRL})\times 100$ $I_{TEST}$—signals from testing compounds; $I_{LMB}$—signals of 50 nM LMB group; $I_{CTRL}$—signals of vehicle control group.

Figure 2B:
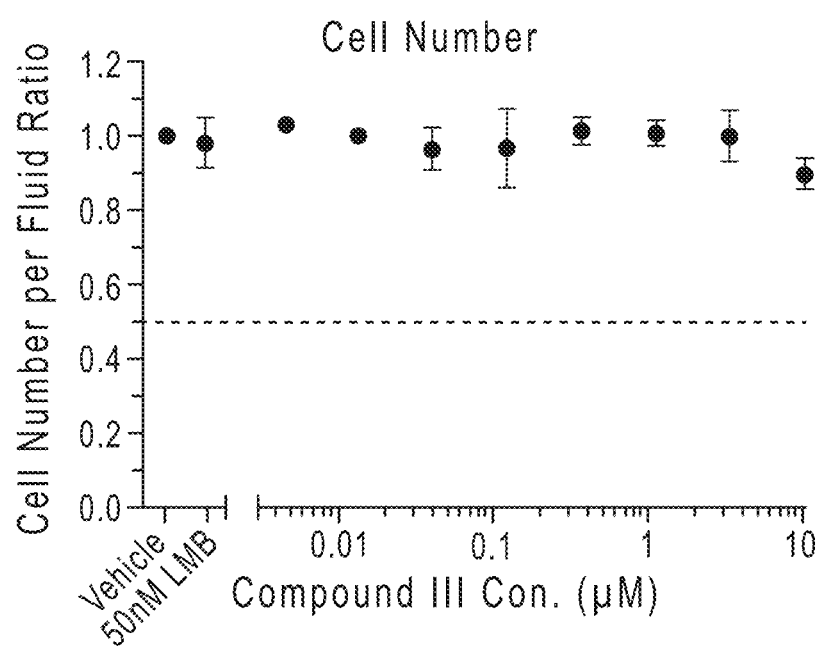

After treated with LMB and Compound III respectively for 1 h, there was dose-dependent for the nuclear redistribution of REV and there was no decrease in cell viability by Compound III at all concentrations tested. The data shows Compound III increases REV nuclear accumulation by inhibiting CRM1 with no effect on cell viability. The results are shown in FIGS. 1A-1C and 2A-2B. FIGS. 1A-1C show the effects of LMB on Rev redistribution in Rev-GFP-U2OS Cells. (1A. Representative images of dose response effects of LMB for 1 h, Green indicated Rev conjugated EGFP; 1B. Dose response curves in the Rev redistribution with LMB treatment. The Vehicle group was set to zero and the 50 nM LMB group was used to represent 100% effect. Values denoted mean±SEM (n=2). EC50=0.11 nM; 1C. Effect of LMB on cell number. The analyzed relative ratios of each group were normalized to Vehicle group. All values denoted are mean±SEM (n=2)). FIGS. 2A-2B show EC50 in REV cargo inhibition by Compound III, and it did not affect cell viability. Rev-GFP was used to evaluate other test compounds, as shown in Table 2.

TABLE 2

Quantitation of inhibition of XPO1 cargo REV nuclear export by test compounds in REV-EGFP U2OS cells.

| Compound | Rev-GFP/EC50 (nM) |
|---|---|
| Compound I | 12.0 |
| Compound II | 28.5 |
| Compound III | 211.4 |
| Compound IV | 14.8 |
| Compound VI | 25.2 |

Example 21

Compound Washout Assay

A compound washout assay was performed to demonstrate sustained, but reversible XPO1 inhibition.

In order to evaluate the duration of XPO1 inhibition by test compounds on XPO1 protein after washout, washout assay was performed using REV-GFP cells. The test compounds and positive control were added to the cell well, and the plate was incubated the at 37° C. and 5% $CO_2$ for 1 h. The drug-containing media were removed, the cells were washed, and the fresh media were added. The cells were imagined at the specified time points 0, 4, 24, 48, 72, and 96 hours to evaluate the inhibition of REV nuclear export. With 50 nM LMB, there was sustained retention of REV protein in the nucleus, up to 24 hours post washout, and the effect gradually decreased to 30% at 72 hours. However, LMB showed toxicity, as indicated by the decrease in cell number, compared to the control. Compound III at EC90 also inhibited nuclear export of REV. Starting at 4 hours post washout, the effect gradually diminished and lost at 24 hours. The cells were well tolerated with Compound III treatment and no decrease in the cell number was observed. In conclusion, compared to positive control LMB Compound III which also covalently bound to the XPO1 protein, showed significant and reversible effect on increasing Rev redistribution in nucleus without any side effect on cell growth in 24 h. The results are shown in FIGS. 3A-3C and 4A-4C. FIGS. 3A-3C show sustained XPO1 inhibition by LMB in washout study (3A. Representative images of LMB effect on Rev redistribution post washout. 3B. Summary of LMB effect on the Rev redistribution post washout. 3C. Effect of LMB on cell viability. The analyzed relative ratios of each group were normalized to each group at 0 h. All values denoted were mean±SEM (n=3).). FIGS. 4A-4C show Compound III's washout effects on Rev redistribution in Rev-EGFP-U2OS Cells. Compound III at EC90 and EC50 (400 nM and 120 nM) were evaluated in this washout REV-EGFP translocation study. Compound III at EC50 showed about 40% effect on nuclear retention of REV, following 1-hour treatment. This effect was gradually diminished to 20% at 4 hours post washout and completely lost at 24 hours. Whereas at 400 nM, Compound III showed sustained XPO1 inhibition at 4 hours and gradually diminished by 24 hours. No Significant effect on cell viability was observed. In conclusion, Compound III showed a time- and dose-dependent inhibition of XPO1 protein, and the effect was sustained for 4 hours and reversible. 4A. Representative images of Compound III effect on Rev redistribution post washout. 4B. Summary of Compound III effect on the Rev redistribution post washout. 4C. Effect of Compound III on cell viability.

Example 22

Pharmacokinetic (PK) Profile and Ratio of Brain to Plasma AUC

Blood was collected from mice (n=3, or 5) to contribute to the total of 10 time points (pre-dose, 5 min, 15 min, 30 min, 1 hour, 2 hours, 4 hours, 8 hours, 12 hours and 24 hours). At the designated time points, animals were anaesthetized under isoflurane, and approximately 110 μL of blood per time point was collected via retro-orbital puncture into pre-cooled $K_2EDTA$ tubes. Blood samples were put on wet ice and centrifuged (2000 g, 5 min at 4° C.) to obtain plasma within 30 minutes of sample collection. All samples were stored frozen at approximately −80° C. until analysis. Prior to analysis, samples were mixed with internal standard in acetonitrile, vortexed, centrifuged, and supernatant was injected for analysis. Concentration of compounds in plasma was determined using LC-MS-MS instrumentation (API 4000, Triple Quadrupole LC/MS/MS Mass Spectrometer). AUC values were calculated using Phoenix Win Nonlin 6.3 software package, PO-Noncompartmental model 200 (extravascular input). The results are shown in Table 3.

TABLE 3

| | | | PK parameters of represented compounds. | | | |
|---|---|---|---|---|---|---|
| I.V. | $T_{1/2}$ (h) | $C_0$ (ng/mL) | $AUC_{0-last}$ (ng · h/mL) | Vdss (L/kg) | Cl (mL/min/kg) | $MRT_{0-last}$ (h) |
| Compound I | 1.62 | 1009 | 1039 | 1.68 | 16.0 | 1.56 |
| Compound II | 3.82 | 558 | 1623 | 3.20 | 10.0 | 4.76 |
| P.O. | $T_{1/2}$ (h) | $T_{max}$ (h) | $C_{max}$ (ng/mL) | $AUG_{0-inf}$ (ng · h/mL) | $MRT_{0-last}$ (h) | $MRT_{0-inf}$ (h) |
| Compound I | 4.72 | 0.75 | 2553 | 10430 | 4.51 | 5.55 |
| Compound II | 4.72 | 2.0 | 1596 | 13905 | 6.90 | 7.84 |

Ratio of Brain to Plasma (B:P).

Figure 5:
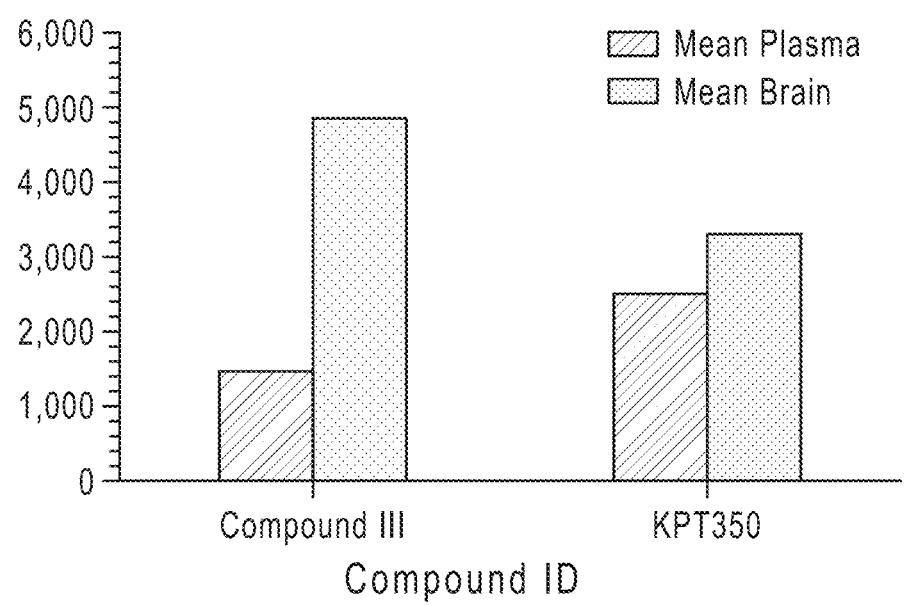
FIG. 5 shows the comparison of brain behavior of Compound III with KPT-350 in cassette PK of brain penetration.

A separate group of mice or rat (n=3, or 5) were dosed (PO at 10 mg/kg) and then sacrificed at the time of maximal plasma concentration ($T_{max}$ at 1-hour post-dose), at which time terminal plasma and brain tissue were collected. Following collection, brain tissue was rinsed with cold saline, dried on filter paper, weighed and snap-frozen by placing on dry ice. All samples were stored frozen at approximately −80° C. until analysis. At the time of analysis, brain tissue was homogenized (homogenizing solution PBS, pH 7.4), mixed with internal standard in acetonitrile, vortexed, centrifuged, and supernatant was injected for analysis. Concentration of compounds in plasma was determined using LC-MS-MS instrumentation (API 4000, Triple Quadrupole LC/MS/MS Mass Spectrometer). Plasma samples were treated with the identical method (except homogenization step) and the concentration of compound in each matrix was calculated based on generated standard curves. The result of the PK assay and the B:P ratio determination are shown in Table 4 and FIG. 5. FIG. 5 shows the comparison of THE brain behavior of Compound III with KPT350 in cassette PK of brain penetration

TABLE 4

| | The ratio of plasma to brain in rats at the dose of 10 mg/kg via PO administration. | |
|---|---|---|
| Time/h | Compound I Brain/Plasma Ratio (ng/g) | Compound II Brain/Plasma Ratio (ng/g) |
| 0.25 | 0.386 810:319 | 0.716 419:301 |
| 1 | 0.707 1887:1301 | 0.954 1274:1191 |
| 8 | 0.782 252:194 | 1.40 677:937 |

Example 23

Maximum Tolerance Dose (MTD) Study

Female BALB/c Nude mice (Supplied by Beijing Ani-Keeper Biotech Co., Ltd., 6-8 weeks old/18-22 g) were quarantined for 7 days before the study. The general health of the animals was evaluated by a veterinarian. Animals with abnormalities were excluded prior the study. General procedures for animal care and use were in accordance with the standard operating procedures (SOPs) of Pharmaron, Inc. The animals were dosed as summarized in table 5.

TABLE 5

Group and treatments.

| Group | Drug | Animals/group | Dose (mg/kg) | Vol (ml/kg) | Route | Regimen |
|---|---|---|---|---|---|---|
| 1 | Compound I | 5 | 25 | 10 | p.o. | qod × 3 (two weeks) |
| 2 | KPT-330 | 5 | 25 | 10 | p.o. | qod × 3 (two weeks) |

Figure 6:
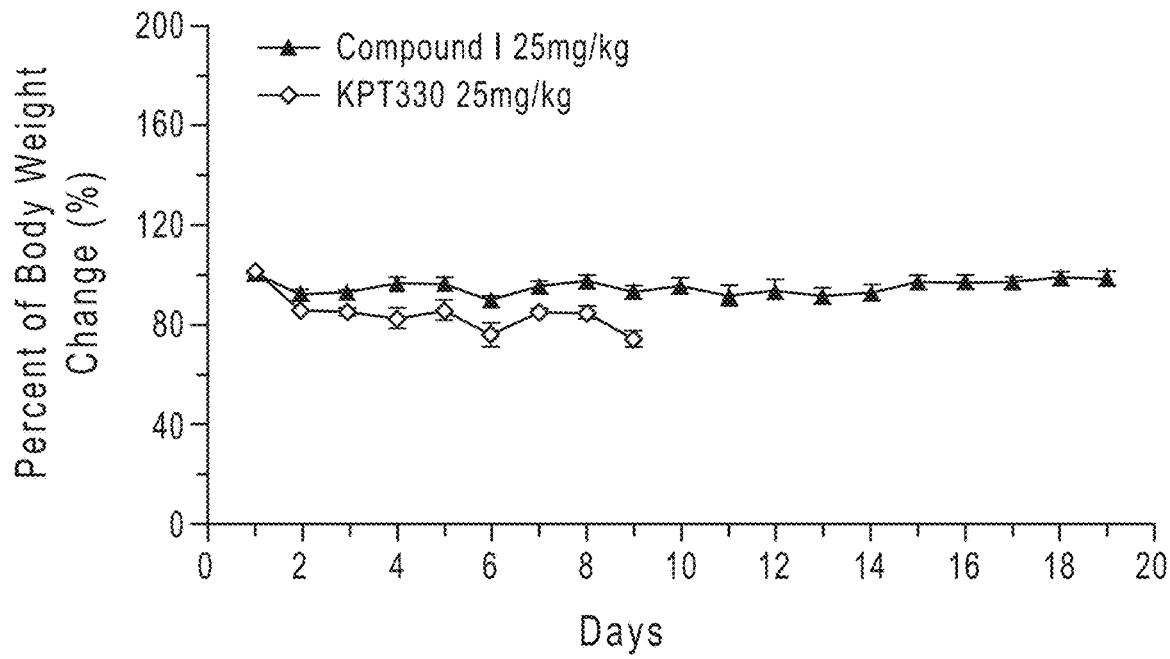
FIG. 6 shows the percent of body weight change of mice receiving Compound III in MTD study.

Body weights of all animals was measured daily. General behavior such as mobility, food and water consumption (by cage side checking only), eye/hair matting and any other abnormal effect were routinely monitored. Any mortality and/or abnormal clinical signs were recorded. Animals showing obvious signs of severe distress and/or pain were humanely sacrificed by carbon dioxide followed by cervical dislocation to ensure death. Animals were euthanized in case of following situations, obvious body weight loss>20% or animals could not get to adequate food or water. The results are shown in FIG. 6. FIG. 6 shows the percent of body weight change % of mice in MTh study. In the KPT-330 group, after one-week dosing, all mice were dead, or anaesthetized for the weight lost up to 20%; however, all mice in the Compound I group (25 mg/kg PO, 3 times a week on every other day for 2 weeks) survived. administration formulation: 10% NMP/10% Solutol/80% (0.5% Poloxamer 188+0.5% PVP).

Example 24

Evaluation of the Antitumor Effect of Compound III on U87MG-Luc Human Glioblastoma Orthotopic Model in BALB/c Nude Mice 23.1. Study Design.

Animals: Female BALB/c Nude mice (Supplied by Beijing AniKeeper Biotech Co., Ltd., 6-8 weeks old/18-22 g) were used. General procedures for animal care and using were in accordance with the standard operating procedures (SOPs) of Pharmaron, Inc.

Grouping and Treatments: Grouping and treatment were started on Day 7 post tumor cells inoculation. Mice were imaged to monitor the tumor growth, then mice were randomly assigned to respective groups using a computer-generated randomization procedure. All test articles were administered orally 20 mg/kg with 3 times/week, for 4 weeks post tumor implantations (n=12 per group).

23.2. Experimental Method and Measurement Parameters.

Cell Culture: The Human glioblastoma U87-luc tumor cell line was maintained in vitro as monolayer culture and used for tumor inoculation Tumor Inoculation and Randomization: $2.5 \times 10^5$ luciferase-expressing U87MG-luc tumor cells suspended in 2 μL MEM medium were injected into the right forebrain by positioning the needle at AP: 2.0 mm, ML: 0.5-1.0 mm, DV: 3.0 mm from bregma. The injection was slowly proceeding over a one-minute period. Upon completing injection, the needle was retained for another minute. Measurement Parameters: Tumor growth (monitored by image analysis), body weight and survival days were recorded.

Termination Criterion: Individual animal was humanely sacrificed by carbon dioxide when body weight loss >20% and animals could not get to adequate food or water.

Statistical Analysis: Data was recorded as means±standard error of the mean for all measurement parameters as study designed. All statistical tests were conducted by SPSS 17.0 statistical software, and the level of significance is set at $p<0.05$.

23.3. Results.

Overall, Compound III at 20 mg/kg exhibited pronounced antitumor activity with 99% reduction in bioluminescence signal compared with the vehicle control group (p values<0.05) at the end of the treatment period. The medium survival time (MST) of animals in vehicle group was 39.5 days, as compared to 47 days in compound III-treated group with a p value<0.0007.

Regarding the safety profile, Compound III at 20 mg/kg was well tolerated by most animals, although individual animal had bodyweight loss less than 10%, which required skipped doses. No other gross clinical abnormalities were observed during the treatment period. In conclusion, Compound III, given orally at 20 mg/kg, 3 times per week, for 4 weeks, was able to significantly prolong the survival of GBM tumor-bearing mice. Taken together, compound III demonstrated BBB-penetrating ability by inhibiting GBM tumor growth and prolonging the survival of animals in the group with U87MG-luc orthotopic tumor.

Figure 7:
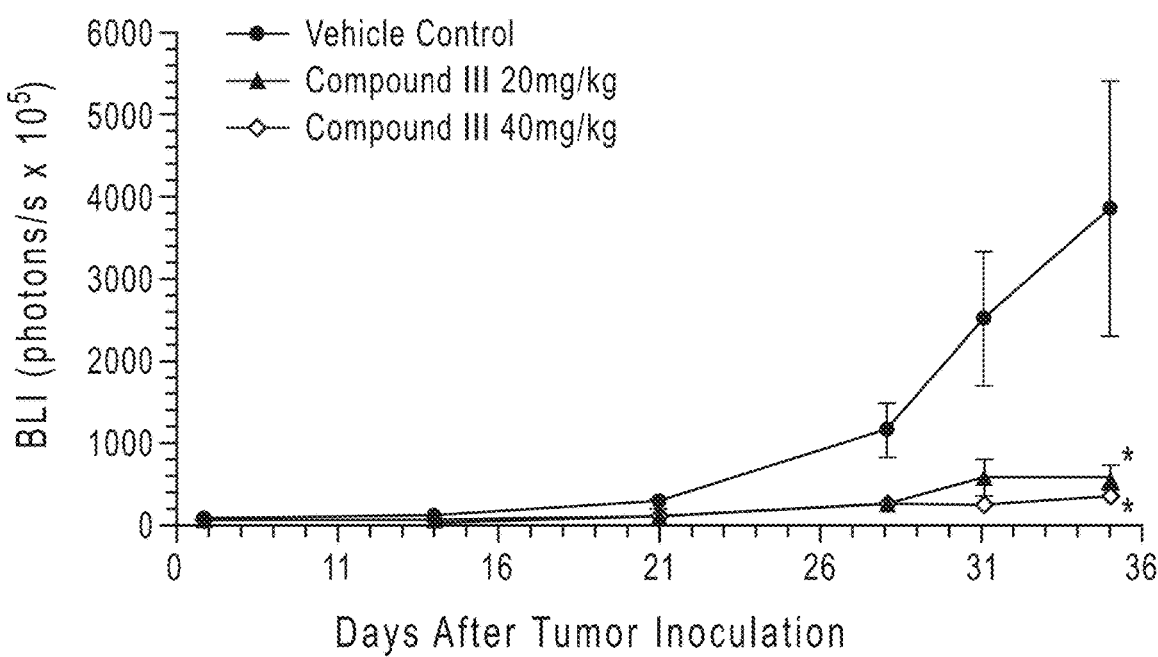
FIG. 7 shows tumor growth inhibition by Compound III in glioblastoma U87-Luc orthotopic xenograft model.
Figure 8:
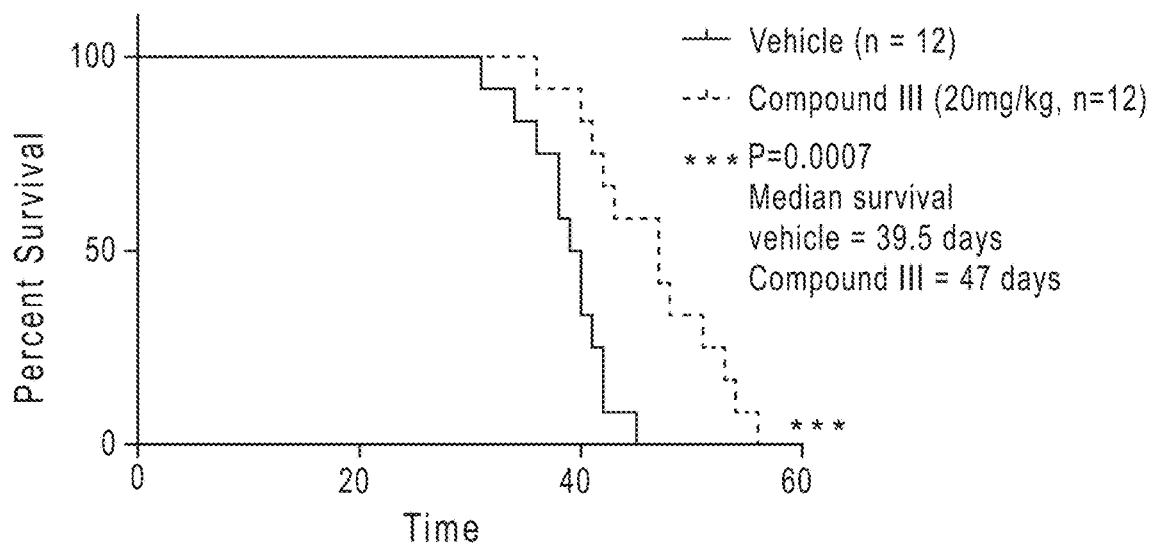
FIG. 8 shows the survival curve of vehicle vs Compound III-treated groups of tumor-bearing mice following 4 weeks of Compound III (20 mg/kg, tiw) treatment.
Figure 9:
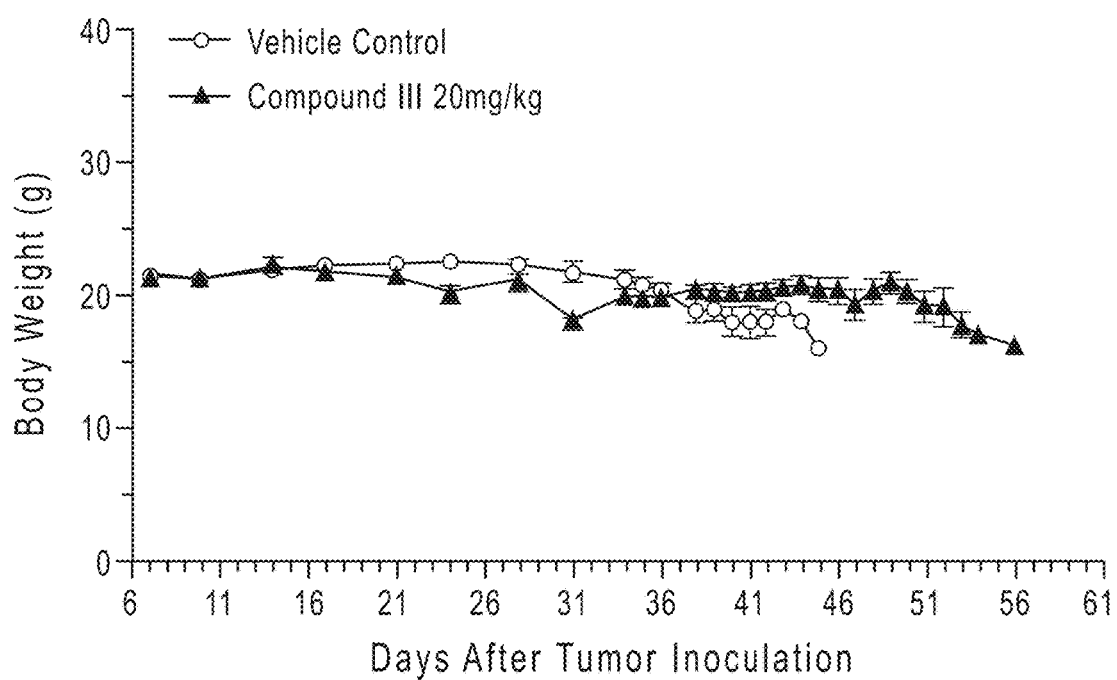
FIG. 9 shows body weight changes during and following treatment (Day 7-Day 65).

The results are shown in FIGS. 7~9. FIG. 7 shows tumor growth inhibition by compound III in U87MG-Luc orthotopic model (logarithmic scale on Y-axis, *p<0.05). FIG. 8 shows the survival curve of vehicle vs compound III-treated group following 4 weeks of treatment at 20 mg/kg, tiw. FIG. 9 shows body weight changes during and following treatment (Day 7-Day 65).

Example 25

Evaluation of PD Effects of Compound III in U87MG-Luc Orthotopic Mouse Model by IHC Based on the bioluminescent signal of tumor, mice were randomly assigned to respective groups using a computer-generated randomization procedure, which included vehicle and compound III-treated groups, respectively, with 5 animals per group. Compound III (20 mg/kg) was given orally 3 times a week (on Day 1, 3, 5) for 2 weeks. Animals for IHC study were euthanized at 6 hours after the last dose and perfused with normal saline followed by fixation with 4% paraformaldehyde. Entire brains containing tumors were collected and kept in fixative for 24 hours before proceeding for paraffin block.

The data of IHC Quantification is shown in FIG. 9. Compared with Vehicle Control group (*p<0.05; **p<0.01), orally administrated Compound III or positive control (KPT-330) on three times a week for 2 weeks significantly decreased the expression of CRM1 and Ki67 in tumors, indicating that Compound III exhibited antitumor effects by inhibiting the expression of CRM1. Compound III inhibited tumor proliferation, as indicated by the decreased Ki67 level in tumors.

Figure 10A:
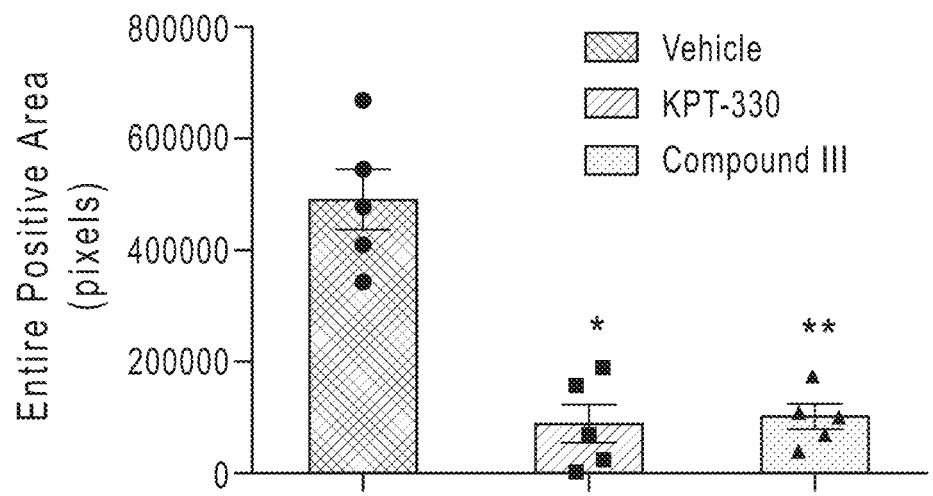
FIGS. 10A-10B illustrate the decrease in Ki67 and CRM1 by XPO1 Compound III in PD study of U87-luc orthotopic xenograft model.
Figure 10B:
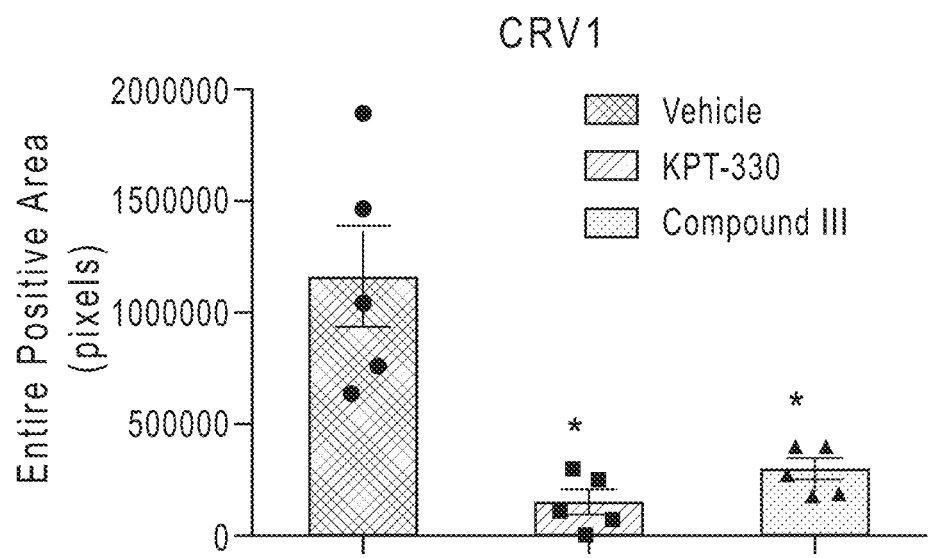

The results are shown in FIGS. 10A and 10B. FIGS. 10A and 10B illustrate the decrease in Ki67 and CRM1 by XPO1 Compound III.

Example 26

Inhibition Activity in Cell Lines

The inhibition activity of test compounds was determined in A-172, U87MG and 3T$_3$-L1 cell lines.

A CellTiter-Glo® luminescent cell viability assay was performed s described in Example 1.

The results are provided in Table 6.

TABLE 6

Inhibition activity.

| Compound | Cell Line | | |
|---|---|---|---|
| | A-172 IC50 (nM) | U87MG IC50 (nM) | 3T3-L1 IC50 (nM) |
| KPT-330 | 224 | 129 | >50000 |
| Compound I | 407 | 226 | >50000 |
| Compound XXIV | 315 | 145 | 41149 |

Example 27

Apoptosis Activity in U87MG Cells

A Capase-Glo® 317 assay was used to determine the apoptosis activity of test compounds in U87MG cells.

Compounds were dissolved in 25 mM DMSO stock solution and serially diluted. DMSO was used as the vehicle control (high control, HC) and culture medium was used as the background (low control LC). The test compounds were applied to plates and spun at 25° C. at 1,000 RPM for 1 min and shaken on a plate shaker for 2 min. Samples (80 nL) of the compounds from the plates were transferred to 384-well cell culture plates using a liquid handler.

Cells were harvested and the cell numbers counted. 40 μL of the cell suspension with the adjusted density was added to 384-well cell culture pates. The final cell density is 1,000 cells/well. Cell culture medium only was used in the low control (LC) samples. The plates were covered with a lid and placed in a 5% $CO_2$ incur at 37° C. for 72 hours.

After incubating for 72 hours, the plates were removed from the incubator and equilibrated at 25° C. for 15 minutes. CellTiter Glo® regen was incubated at 37° C. before the experiments. 40 μL of Capase-Glo® 3/7 was added into each well to be detected at a 1:1 ratio to culture medium. The plates were then placed at 25° C. for 30 min and read using an EnSpire® Plate Reader.

The % activity remaining was determined using the following formula: % Remaining Activity=300×(Lumsample−LumLC)/(LumHC−LUM LC), where HC is obtained from cells treated with 0.1% DMSO only, LC is obtained from culture medium only.

The results are presented in Table 7.

TABLE 7

Apoptosis activity in U87MG cells.

| | U87MG | |
|---|---|---|
| Compound | EC50 (nM) | % Emax |
| KPT-330 | 12620 | 398 |
| Compound I | 16027 | 325 |
| Compound XXIV | 1211 | 233 |

Example 28

Cytotoxicity in Cell Lines

The cytotoxicity of test compounds in brain (HCN2), colon cancer (HCT116) and normal colon cell (C8-B4) lines was determined using the cell proliferation assay as described in Example 19.

The results are presented in Table 8.

TABLE 8

Cytotoxicity in cell lines.

| | Cell Line | | | | | |
|---|---|---|---|---|---|---|
| | HCT116 | | HCN2 | | C8-B4 | |
| Compound | IC50 (nM) | Max % inh | IC50 (nM) | Max % inh | IC50 (nM) | Max % inh |
| KPT-330 | 2130 | 98 | 30675 | 99 | 1274 | 100 |
| Compound I | 5960 | 88 | >50000 | 22 | 4301 | 91 |
| Compound XXIV | 2216 | 99 | 15274 | 99 | 689 | 100 |

The cytotoxicity of test compounds was also determined in glioblastoma (U87MG)), brain (HCN2) and 3T3 cell lines was determined using the cell proliferation assay as described in Example 19.

Figure 11:
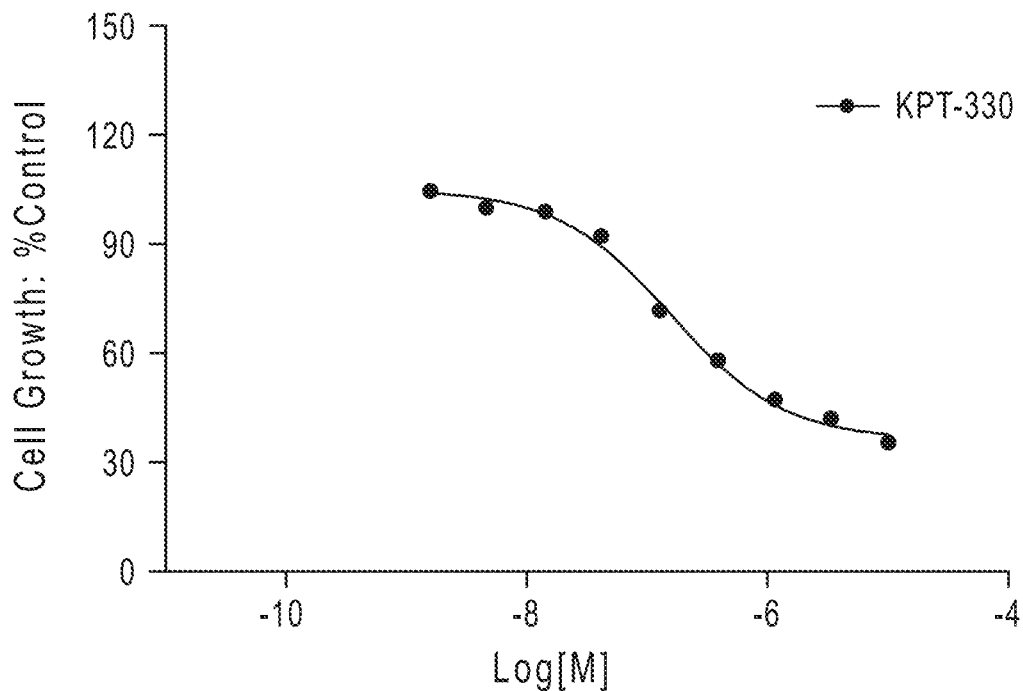
FIG. 11 shows the percent cell growth relative to control following incubation with KPT-330 in a cell proliferation assay.
Figure 12:
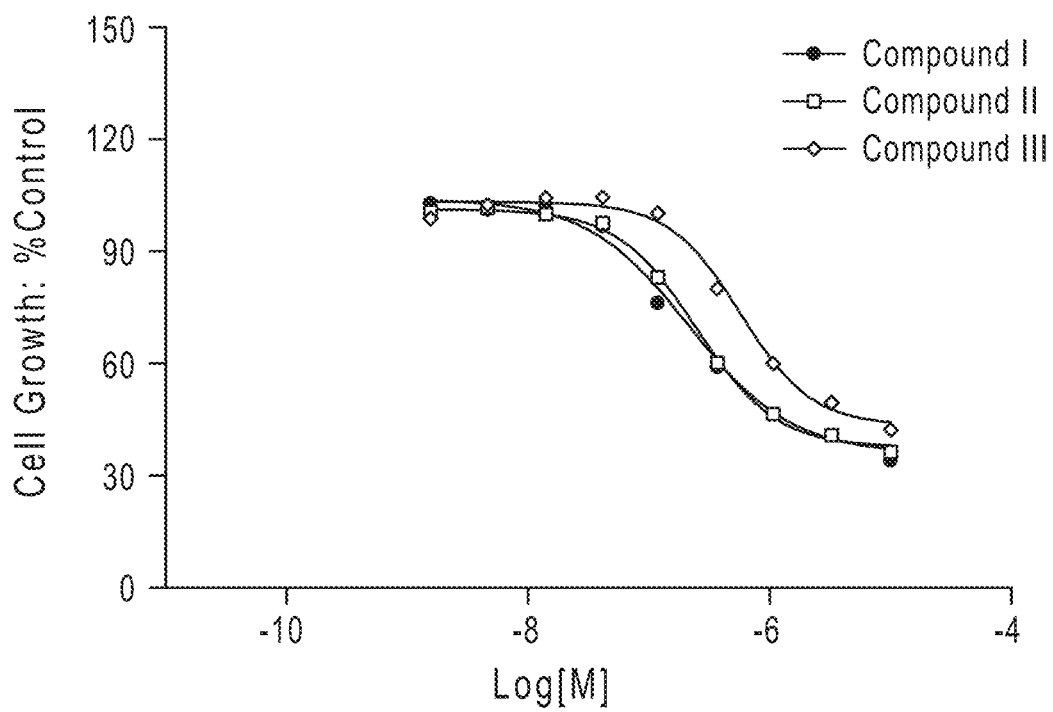
FIG. 12 shows the percent cell growth relative to control following incubation with certain compounds provided by the present disclosure in a cell proliferation assay.

The results are presented in Table 9 and in FIGS. 11 and 12.

TABLE 9

Inhibition activity in cell lines.

| | Cell Line | | |
|---|---|---|---|
| Compound | U87MG IC50 (nM) | HCN2 IC50 (nM) | 3T3 IC50 (nM) |
| KPT-330 | 520 | 710 | 34162 >50000 |
| Compound I | 384 | 798 | 25812 >50000 |
| Compound II | 537 | 723 | 44749 ND |
| Compound III | 1123 | 2364 | >50000 ND |

FIGS. 11 and 12 show the percent cell growth relative to control following incubation with the compounds in the cell proliferation assay.

Example 29

Inhibition in Rev-GFP Translocation Assay

The inhibitory activity of test compounds was determined using the Rev-GFP translocation assay described in Example 20.

The results are presented in Table 10.

TABLE 10

Inhibition in Rev-GFP translocation assay.

| Compound | Rev-GFP/IC50 (nM) |
|---|---|
| Compound I | 16.3/7.7 |
| Compound III | 298.0/124.8 |
| Compound II | 35.2/21.8 |
| KPT-330 | 6.8/3.8 |
| Compound VI | 25.2 |
| Compound IV | 14.8 |

FIGS. 13A-13C show the EC50 of XPO1 inhibition by Compound I and Compound III in the REV-GFP U2OS assay;

Example 30

Cytotoxicity in Cell Lines

The cytotoxicity of test compounds in T98G, LN-229, and U251 cell lines was determined using the cell proliferation assay as described in Example 19.

Figure 14:
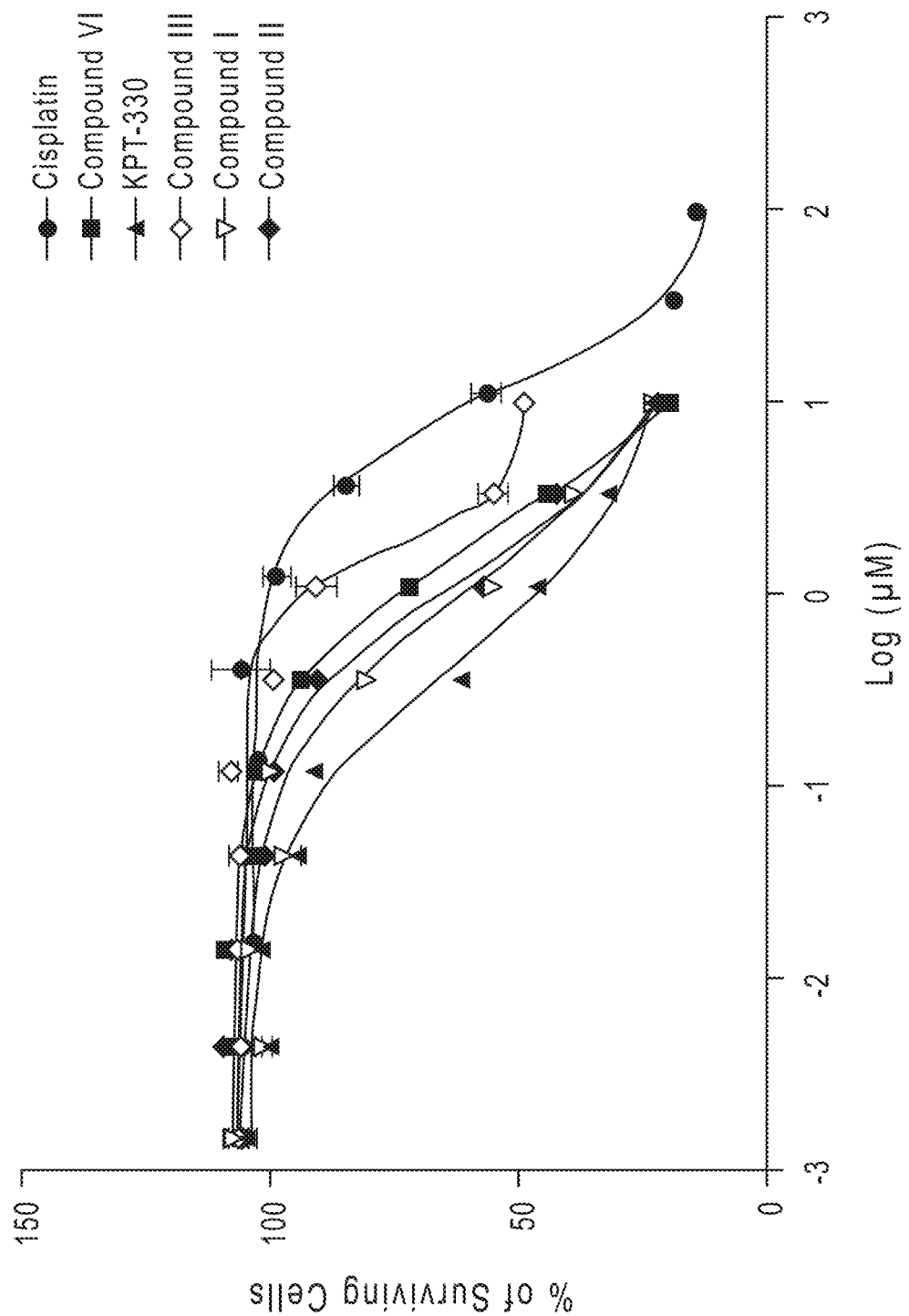
FIGS. 14-16 show the inhibition of cell growth in T98G, LN-229, and U251 cells, respectively, following incubation with various compounds.
Figure 15:
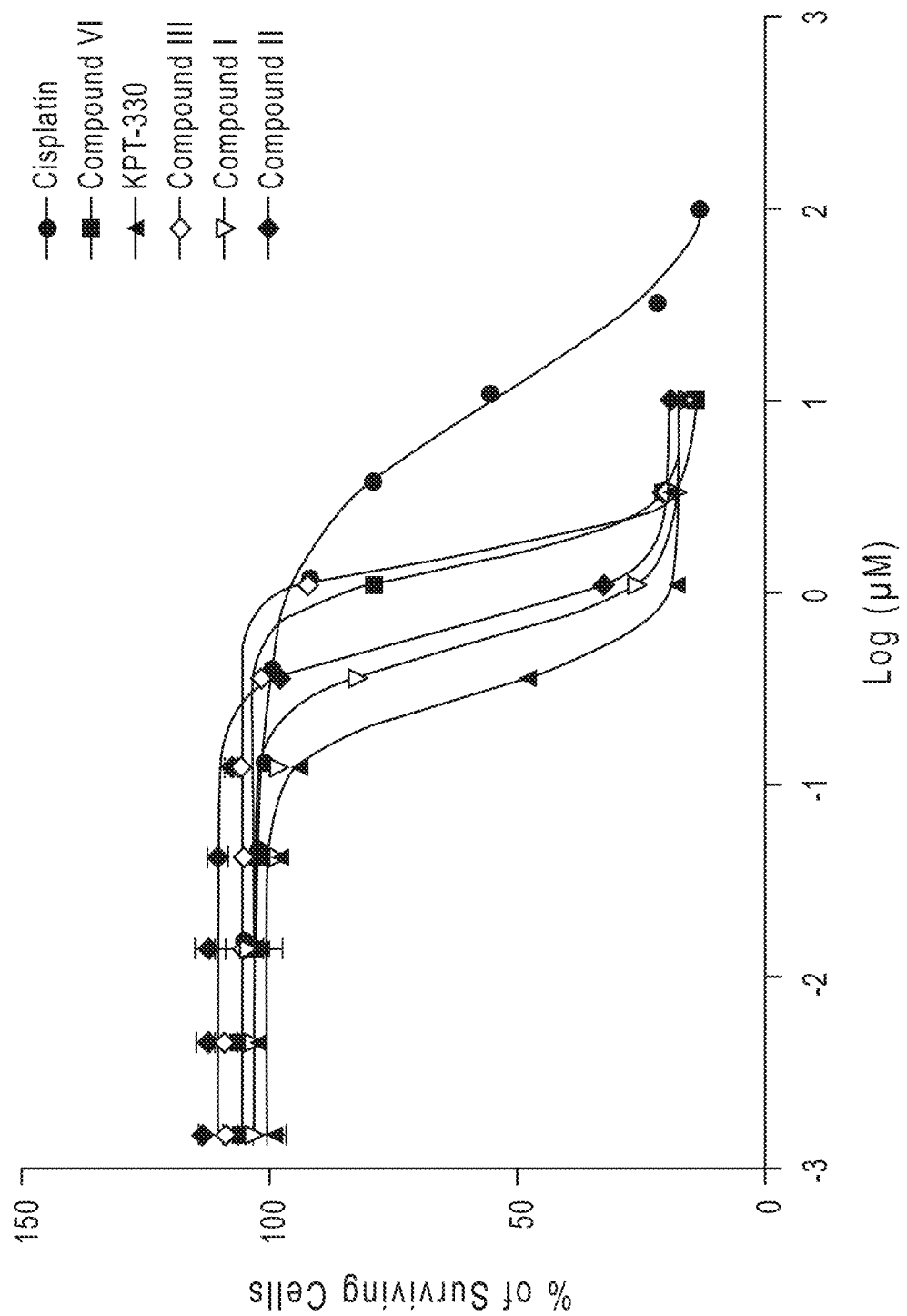
Figure 16:
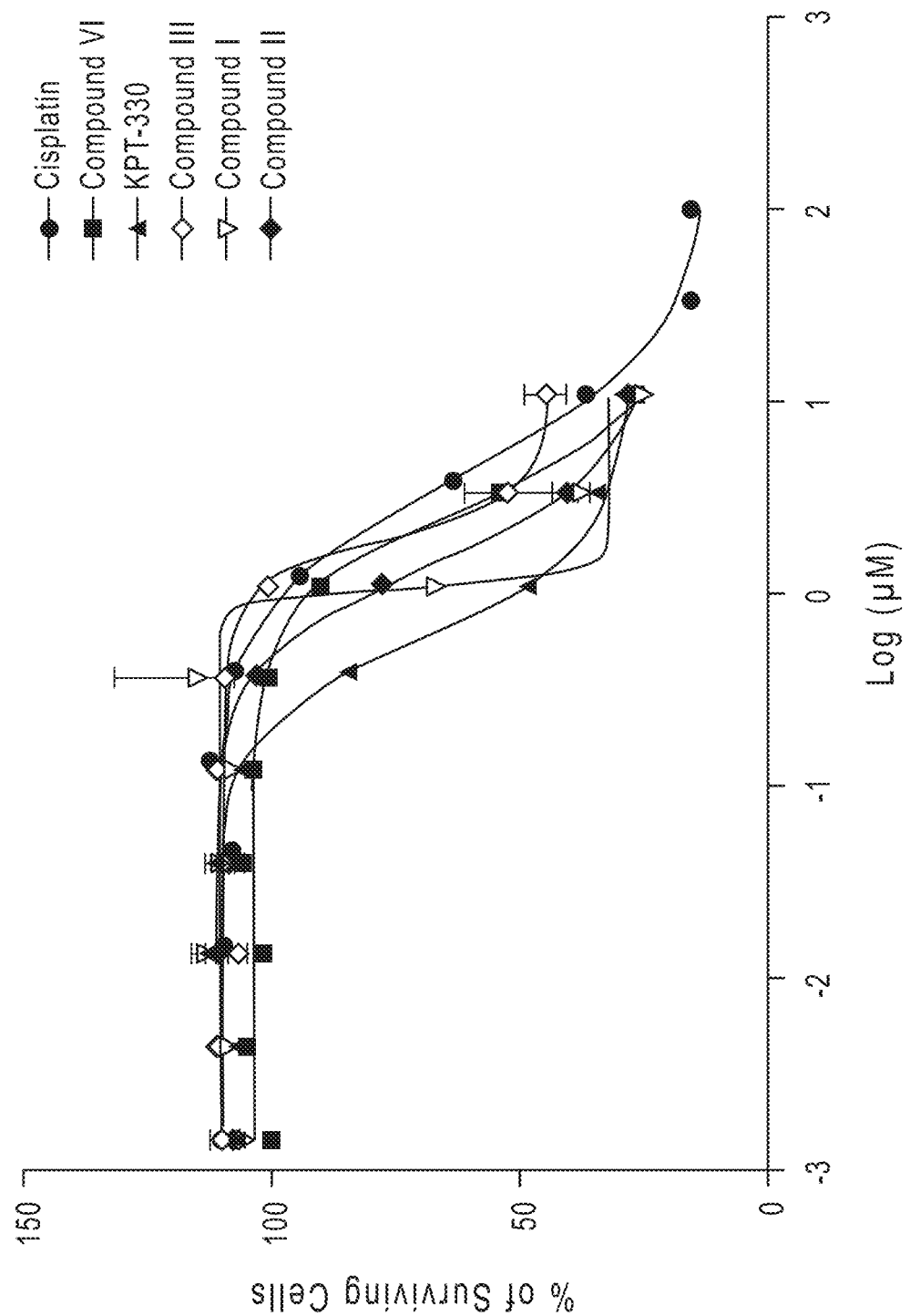

The results are presented in Table 11 and in FIGS. 14-16.

TABLE 11

Inhibition activity in cell lines.

| | Absolute IC50 (μM) | | |
|---|---|---|---|
| Compound | T98G | LN-229 | U251 |
| Cisplatin | 12.3 | 13.0 | 6.0 |
| KPT-330 | 0.8 | 0.3 | 1.0 |
| Compound I | 1.7 | 0.6 | 1.2 |
| Compound II | 1.9 | 0.8 | 2.3 |
| Compound III | 6.2 | 1.8 | 3.8 |
| Compound VI | 2.6 | 1.7 | 3.8 |

FIGS. 14-16 show the inhibition of cell growth in T98G, LN-229, and U251 cells, respectively, following incubation with various compounds.

Example 31

Cytotoxicity of Compound III and Analogs in U87MG Cells

The cytotoxicity of test Compound III and several analogs in U87MG cells was determined using the cell proliferation assay as described in Example 19.

The results are presented in Table 12.

TABLE 12

Inhibition activity in cell lines.

| Compound | Absolute IC50 (μM) | Relative IC50 (μM) | Top | Bottom | Hill Slope | Max % Inhibition |
|---|---|---|---|---|---|---|
| Compound VII | NA | 0.1 | 45.9 | −6.4 | 1.2 | 49.0 |
| Compound VIII | NA | 0.1 | 38.8 | −10.6 | 1.8 | 44.0 |
| Compound IX | NA | 0.1 | 43.6 | −4.6 | 1.6 | 48.3 |
| Compound X | 9.4 | 0.2 | 59.4 | −15.9 | 0.5 | 58.3 |
| Compound XI | NA | 0.2 | 44.6 | −7.6 | 1.8 | 48.5 |
| Compound XII | 18.5 | 0.6 | 50.9 | −5.5 | 1.2 | 53.9 |
| Compound III | NA | 0.2 | 40.2 | −4.2 | 3.2 | 46.3 |
| KPT-350 | 10.0 | 0.3 | 53.0 | −13.2 | 0.8 | 49.4 |

Example 32

Pharmacokinetic Profile

The pharmacokinetic profile of test compounds in mice or rats was determined from several test compounds was determined using the methods described in Example 22.

The results are presented in Table 13.

TABLE 13

Pharmacokinetic profile summary for test compounds in mice or rats.

| | KPT-330 | Compound III | Compound I | Compound II | Compound IV |
|---|---|---|---|---|---|
| Rev-GFP assay/μM | 0.005 | 0.210 | 0.012 | 0.035 | 0.015 |
| $T_{1/2}$/(h) | 1.7 | 5.2 | 4.7 | 6.9 | 2.9 |
| $C_{max}$/(ng/mL) plasma/brain | — | 1247/1191 (3 mpk) | 1887/1301 (10 mpk) | 1044/1772 (5 mpk/mice) | 276/68.5 (5 mpk) |
| Cmax (ng/ml) plasma/10 mpk | 2517 | 1596 | 2553 | 796 | 312 |
| AUC/10 mpk | 8416 | 13905 | 10015 | 4149 | 1057 |
| B/P ratio ($C_{max}$ time) 10 mpk | 0.64 | 0.95 (1 h) | 0.71 | 1.58 (5 mpk/mice/ AUC Ratio) | 0.29 (5 mpk/ AUC Ratio) |

TABLE 13-continued

Pharmacokinetic profile summary for test compounds in mice or rats.

|  | KPT-330 | Compound III | Compound I | Compound II | Compound IV |
|---|---|---|---|---|---|
| cLogP | 2.68 | 3.83 | — | — | — |
| Bioavailability | — | 82% | 98% | — | 27% |
| Salt form | HCl | no | yes | no | no |
| MTD | 15 | <25 mpk (SEB-β-CD20%/1%tween80/79%water) | — | — | — |

It should be noted that there are alternative ways of implementing the embodiments disclosed herein. Accordingly, the present embodiments are to be considered as illustrative and not restrictive. Furthermore, the claims are not to be limited to the details given herein and are entitled their full scope and equivalents thereof.

What is claimed is:

1. A compound having the structure of Formula (I') or Formula (II'):

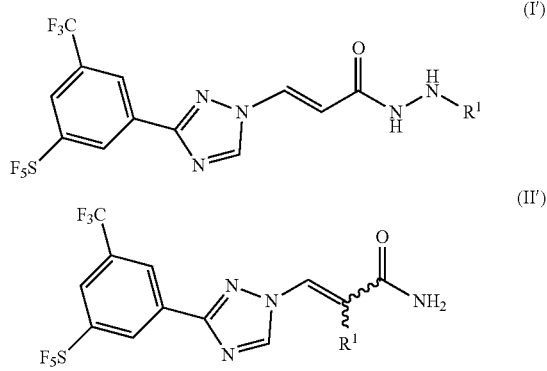

or a pharmaceutically acceptable salt, wherein, $R^1$ is selected from —C(=O)—$R^2$, a 3- to 6-membered heterocycloalkyl, and a 5- to 10-membered heteroaryl, optionally substituted with one or more substituents selected from deuterium, —OH, —SH, —NO$_2$, halogen, amino, cyano, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, and $C_{1-12}$ alkylsulfanyl; and $R^2$ is selected from $C_{1-6}$ alkyl, $C_{3-6}$ cycloalkyl, and a 3- to 6-membered heterocycloalkyl, optionally substituted with one or more substituents selected from halogen, amino, cyano, $C_{1-12}$ alkyl, $C_{2-12}$ alkenyl, $C_{2-12}$ alkynyl, $C_{1-12}$ alkoxy, $C_{1-12}$ haloalkyl, $C_{1-12}$ haloalkoxy, and $C_{1-12}$ alkylsulfanyl.

2. The compound of claim 1, wherein the compound has the structure of Formula (I').

3. The compound of claim 1, wherein the compound has the structure of Formula (II').

4. The compound of claim 1, wherein $R^1$ is —C(=O)—$R^2$.

5. The compound of claim 4, wherein $R^2$ is selected from methyl, ethyl, n-propyl, isopropyl, cyclopropyl, n-butyl, t-butyl, cyclobutyl, isobutyl, 4-methyl-2-pentyl, 2,2-dimethyl-1-butyl, 3,3-dimethyl-1-butyl, 2-ethyl-1-butyl, cyclopentenyl, and tetrahydrofuran,

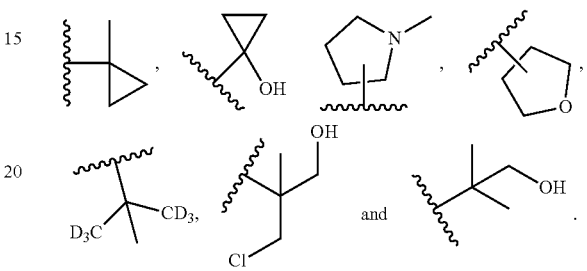

6. The compound of claim 4, wherein $R^2$ is selected from 2-methyloxiranyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, n-pentyl, isopentyl, neopentyl, 2,2-dimethylbutanyl, and

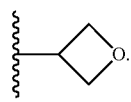

7. The compound of claim 1, wherein $R^1$ is selected from unsubstituted or substituted

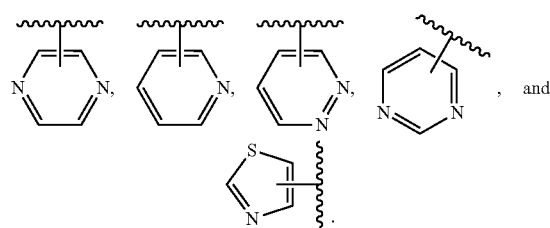

8. The compound of claim 1, wherein $R^1$ is selected from unsubstituted or substituted furyl, pyrrolyl, imdazolyl, triazolyl, tetrazolyl, oxazolyl, oxadiazolyl, 1,3,5-triazinyl, thiazolyl, and thienyl.

9. The compound of claim 1, wherein $R^1$ is selected from unsubstituted or substituted

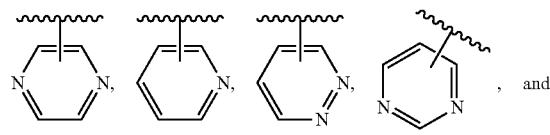

-continued

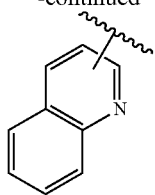

10. The compound of claim 1, wherein $R^1$ is selected from unsubstituted or substituted phenyl, naphthyl, furyl, benzofuryl, pyrrolyl, imdazolyl, benzimdazolyl, triazolyl, tetrazolyl, oxazolyl, oxadiazolyl, 1,3,5-triazinyl, thiazolyl, thienyl, benzothienyl, indolyl, purinyl, quinolyl, isoquinolyl and phenoxathiinyl.

11. A pharmaceutical composition comprising:
  the compound of claim 1; and
  a pharmaceutically acceptable excipient, carrier, adjuvant, vehicle, or combination of any of the foregoing.

12. The pharmaceutical composition of claim 11, wherein the pharmaceutical composition is an oral formulation.

13. A method of treating cancer in a patient comprising administering to a patient in need of such treatment a therapeutically effective amount of the compound of claim 1 or a pharmaceutically acceptable salt thereof, wherein the cancer is glioblastoma.

14. A method of treating cancer in a patient comprising administering to a patient in need of such treatment a therapeutically effective amount of the pharmaceutical composition of claim 11, wherein the cancer is glioblastoma.

\* \* \* \* \*